(12) United States Patent
Rummery et al.

(10) Patent No.: US 9,616,190 B2
(45) Date of Patent: Apr. 11, 2017

(54) PAP SYSTEM

(75) Inventors: Gerard Michael Rummery, Woodford (AU); Benjamin John Hunter, Turramurra (AU); Robert Edward Henry, Baulkham Hills (AU); Jose Ignacio Romagnoli, Redfern (AU); James William Charles Vandyke, Glebe (AU); David Anthony Pidcock, Castle Hill (AU); Rupert Christian Scheiner, Davidson (AU); Stuart Norris Plascott, Macquarie Park (AU); Stewart Joseph Wagner, Bowen Mountain (AU); Jamie Graeme Wehbeh, Mosman (AU)

(73) Assignee: ResMed Limited, Bella Vista (AU)

( * ) Notice: Subject to any disclaimer, the term of this patent is extended or adjusted under 35 U.S.C. 154(b) by 400 days.

(21) Appl. No.: 13/819,128

(22) PCT Filed: Aug. 26, 2011

(86) PCT No.: PCT/AU2011/001107
§ 371 (c)(1),
(2), (4) Date: Feb. 26, 2013

(87) PCT Pub. No.: WO2012/024740
PCT Pub. Date: Mar. 1, 2012

(65) Prior Publication Data
US 2013/0152918 A1 Jun. 20, 2013

Related U.S. Application Data

(60) Provisional application No. 61/344,588, filed on Aug. 27, 2010, provisional application No. 61/457,317, filed on Feb. 25, 2011.

(51) Int. Cl.
*A61M 16/06* (2006.01)
*A61M 16/08* (2006.01)
*A61M 16/00* (2006.01)

(52) U.S. Cl.
CPC ........ *A61M 16/0683* (2013.01); *A61M 16/00* (2013.01); *A61M 16/0066* (2013.01);
(Continued)

(58) Field of Classification Search
CPC ............. A61M 16/00; A61M 16/0057; A61M 16/0066; A61M 16/06; A61M 16/0605;
(Continued)

(56) References Cited

U.S. PATENT DOCUMENTS 4,516,573 A * 5/1985 Gedeon ............. A61M 16/1045
128/201.13
5,556,370 A * 9/1996 Maynard ............. A61B 1/0058
600/142
(Continued)

FOREIGN PATENT DOCUMENTS

CN 1681552 10/2005
CN 101380497 3/2009
(Continued)

OTHER PUBLICATIONS

International Search Report for PCT/AU2011/001107, mailed Nov. 25, 2011.
(Continued)

*Primary Examiner* — Tan-Uyen (Jackie) T Ho
*Assistant Examiner* — Joseph D Boecker
(74) *Attorney, Agent, or Firm* — Nixon & Vanderhye P.C.

(57) ABSTRACT

A PAP system adapted for treatment of respiratory disease or sleep disordered breathing includes headgear adapted to engage a patient's head, a patient interface adapted to be secured to and sealed against a portion of a patient's face, in
(Continued)

use, by the headgear, a flow generator adapted to be connected to the patient interface, and wherein the flow generator is adapted to be secured by a portion of the headgear to the patient's head, and an outlet tube to interconnect the flow generator and the patient interface. The patient interface includes a frame and a sealing arrangement supported by the frame. The sealing arrangement includes a seal portion, a body portion, and an inlet tube in communication with the outlet tube. The frame and the outlet tube are constructed of a relatively rigid material.

39 Claims, 57 Drawing Sheets

(52) U.S. Cl.
CPC .... *A61M 16/0644* (2014.02); *A61M 16/0875* (2013.01); *A61M 2209/088* (2013.01); *A61M 2210/06* (2013.01)

(58) Field of Classification Search
CPC .......... A61M 16/0627; A61M 16/0633; A61M 16/0644; A61M 16/0683; A61M 16/0694; A61M 16/08; A61M 16/0816; A61M 16/0825; A61M 16/0875; A61M 2016/0661; A61M 39/10; A61M 39/1011; A61M 39/12; A61M 2039/1027; A61M 2205/3334; A61M 2209/088; A61M 2210/06
USPC ............ 128/200.28, 201.22, 201.23, 202.27, 128/204.11, 204.18, 205.22, 205.25, 128/206.12, 206.21, 206.24, 128/206.26–206.28, 207.11
See application file for complete search history.

(56) References Cited

U.S. PATENT DOCUMENTS

| | | | |
|---|---|---|---|
| 6,374,826 B1 | 4/2002 | Gunaratnam et al. | |
| 6,427,694 B1* | 8/2002 | Hecker | A61M 16/06 128/201.22 |
| D466,607 S * | 12/2002 | Cise | D24/110 |
| 6,524,180 B1* | 2/2003 | Simms | B08B 15/002 285/184 |
| 6,662,802 B2* | 12/2003 | Smith | A61M 16/08 128/200.24 |
| 6,668,825 B2* | 12/2003 | Cardon | A61M 16/0084 128/202.27 |
| 6,925,655 B1* | 8/2005 | Maki | A42B 3/28 128/201.24 |
| 7,534,005 B1* | 5/2009 | Buckman | A61F 9/068 2/8.2 |
| 7,726,309 B2 | 6/2010 | Ho et al. | |
| 8,460,417 B2* | 6/2013 | Reid | B08B 15/04 55/356 |
| 2002/0148472 A1* | 10/2002 | Barnett | A61M 16/06 128/206.24 |
| 2006/0096596 A1 | 5/2006 | Occhialini et al. | |
| 2006/0213516 A1 | 9/2006 | Hoffman | |
| 2006/0237013 A1 | 10/2006 | Kwok | |
| 2006/0237017 A1* | 10/2006 | Davidson | A61M 16/06 128/205.25 |
| 2006/0283461 A1* | 12/2006 | Lubke | A61M 16/06 128/207.11 |
| 2007/0049800 A1* | 3/2007 | Boulais | A61B 1/00103 600/142 |
| 2007/0209663 A1* | 9/2007 | Marque | A61M 16/0683 128/207.11 |
| 2007/0240721 A1* | 10/2007 | Ho | A61M 16/06 128/207.13 |
| 2007/0277827 A1 | 12/2007 | Bordewick et al. | |
| 2007/0277828 A1* | 12/2007 | Ho | A61M 16/08 128/206.21 |
| 2008/0149105 A1* | 6/2008 | Matula | A61M 16/06 128/206.29 |
| 2008/0178879 A1 | 7/2008 | Roberts et al. | |
| 2008/0276937 A1 | 11/2008 | Davidson et al. | |
| 2008/0314388 A1* | 12/2008 | Brambilla | A61M 16/06 128/205.25 |
| 2009/0044808 A1* | 2/2009 | Guney | A61M 16/0666 128/206.24 |
| 2009/0050156 A1 | 2/2009 | Ng et al. | |
| 2009/0065005 A1* | 3/2009 | Ades | A61M 16/06 128/205.25 |
| 2009/0194101 A1 | 8/2009 | Kenyon et al. | |
| 2009/0320842 A1 | 12/2009 | Doherty et al. | |
| 2010/0170513 A1 | 7/2010 | Bowditch et al. | |
| 2011/0220113 A1* | 9/2011 | Newman | A61M 16/0683 128/206.24 |
| 2012/0152255 A1* | 6/2012 | Barlow | A61M 16/0066 128/205.25 |
| 2012/0167879 A1* | 7/2012 | Bowman | A61M 16/0066 128/201.22 |
| 2012/0174922 A1* | 7/2012 | Virr | A61M 16/0066 128/203.12 |
| 2012/0216819 A1* | 8/2012 | Raje | A61M 16/06 128/848 |

FOREIGN PATENT DOCUMENTS

| | | |
|---|---|---|
| CN | 101410149 | 4/2009 |
| CN | 101460211 | 6/2009 |
| CN | 101466429 | 6/2009 |
| CN | 1623610 | 6/2015 |
| EP | 2 005 986 | 12/2008 |
| WO | WO 2006/138416 | 12/2006 |
| WO | WO 2007/117716 | 10/2007 |
| WO | WO 2008028247 A1 * | 3/2008 ............ A61M 16/06 |
| WO | PCT/AU2009/001102 | 8/2009 |
| WO | PCT/AU2010/001031 | 8/2010 |
| WO | PCT/AU2010/001106 | 8/2010 |
| WO | WO 2010/135785 | 12/2010 |

OTHER PUBLICATIONS

Product Brochure for BreatheX—"Sleep Around—Sleep Sound," 2006, 2 pages.
Chinese Office Action issued in a corresponding Appln. No. 201180041806.X dated Nov. 3, 2014 with English language translation thereof.
Second Office Action issued in corresponding Chinese Application No. 201180041806.X dated May 20, 2015, with English Translation thereof.

* cited by examiner

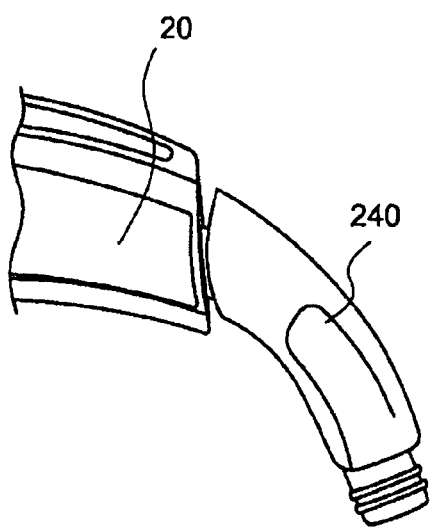
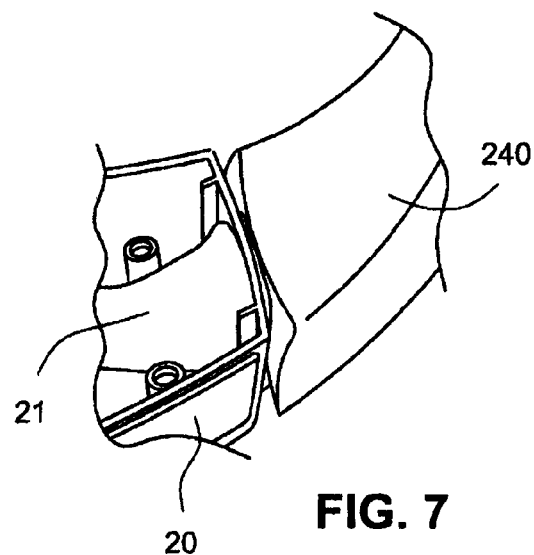
FIG. 6         FIG. 7
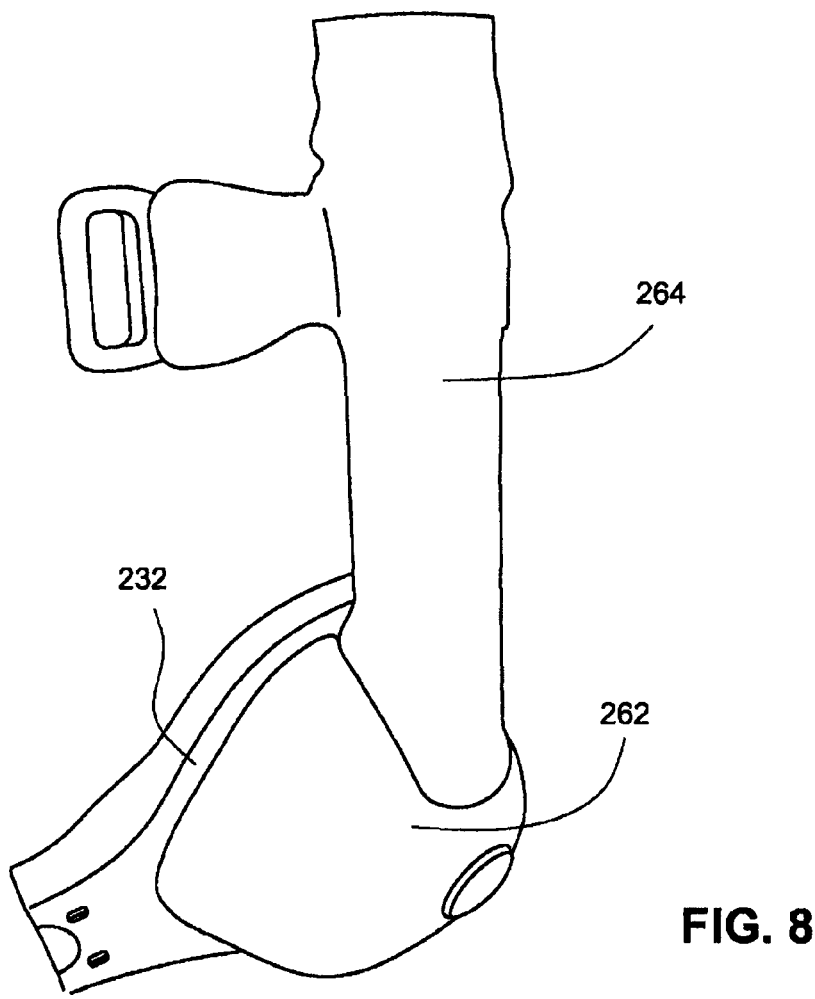
FIG. 8

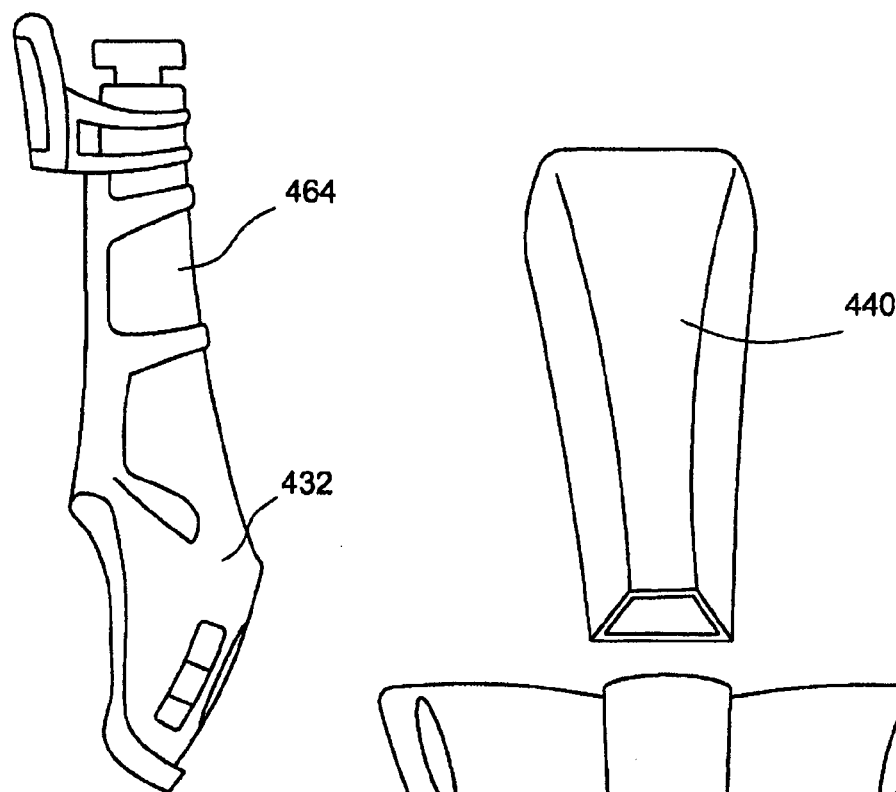
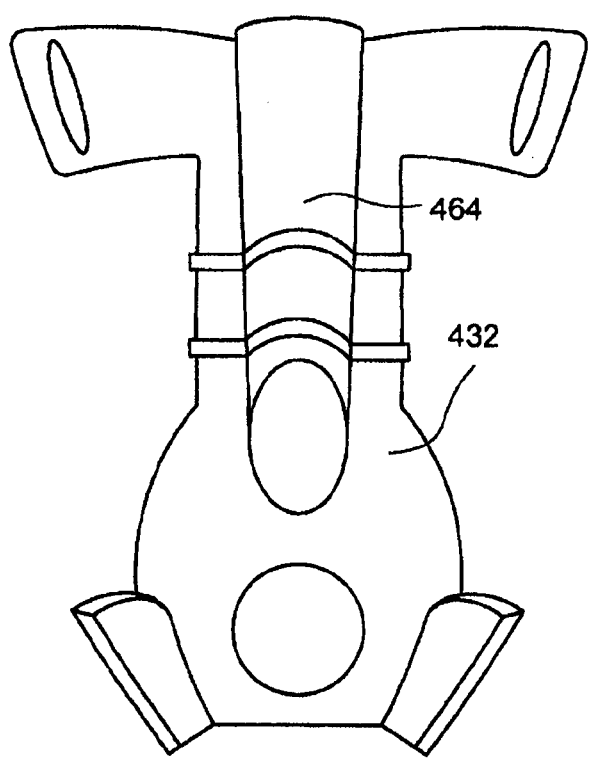
FIG. 13
FIG. 14
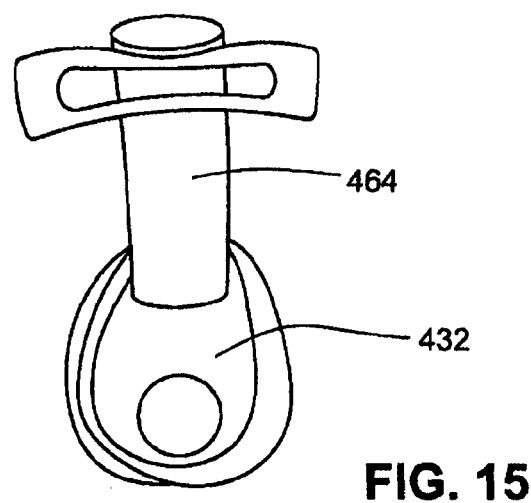
FIG. 15

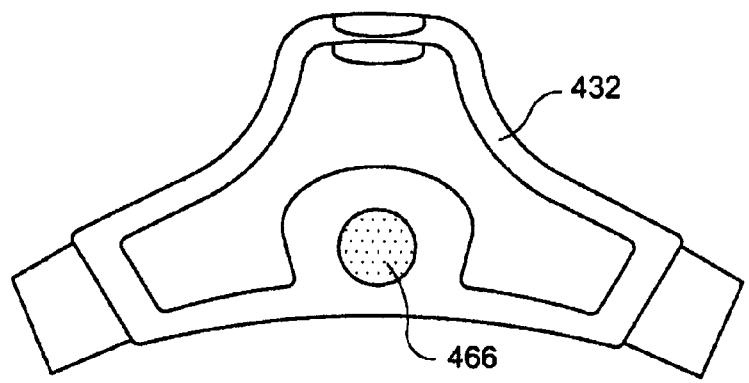
FIG. 23
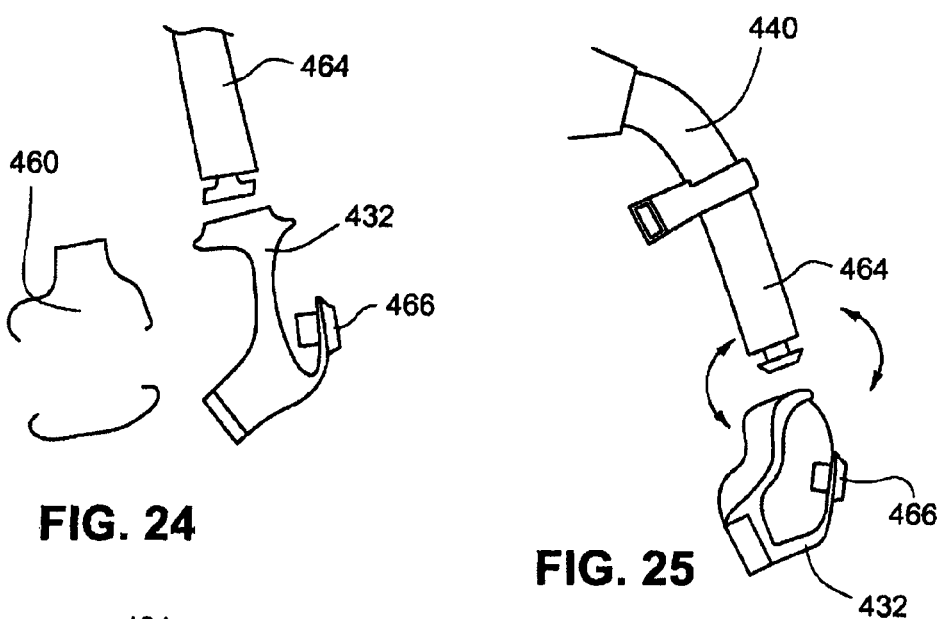
FIG. 24
FIG. 25
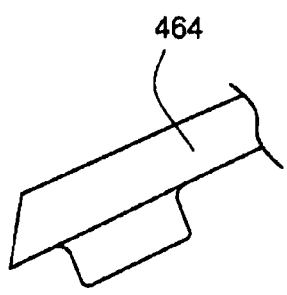
FIG. 26
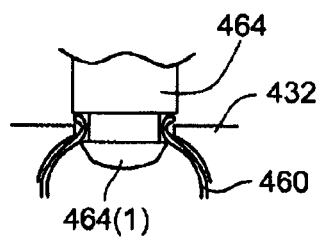
FIG. 27
FIG. 28

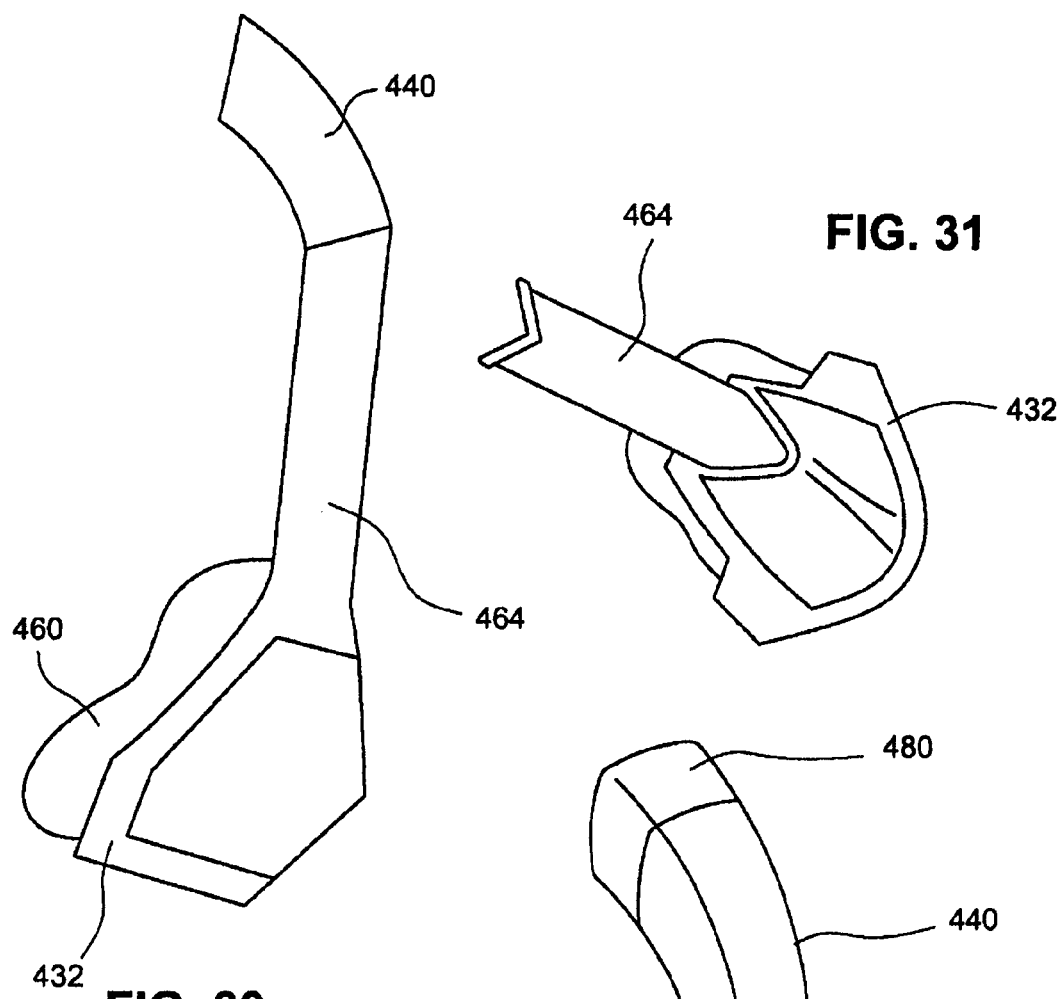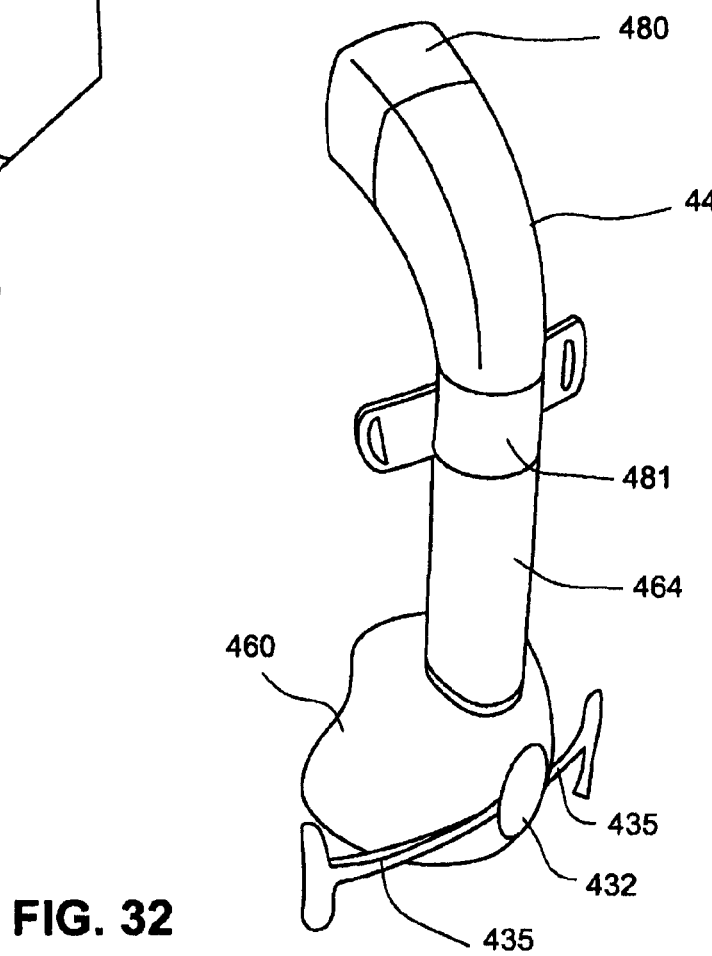

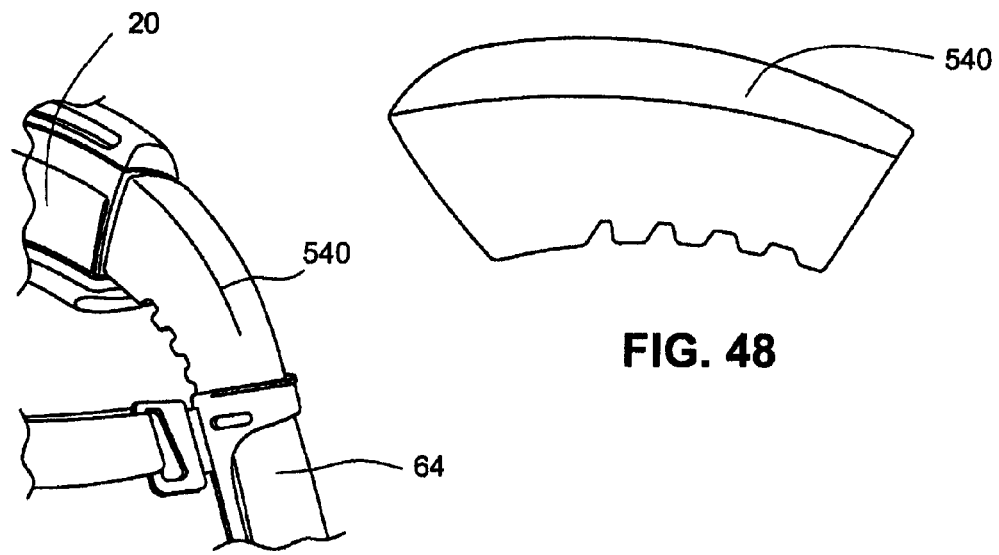
FIG. 47
FIG. 48
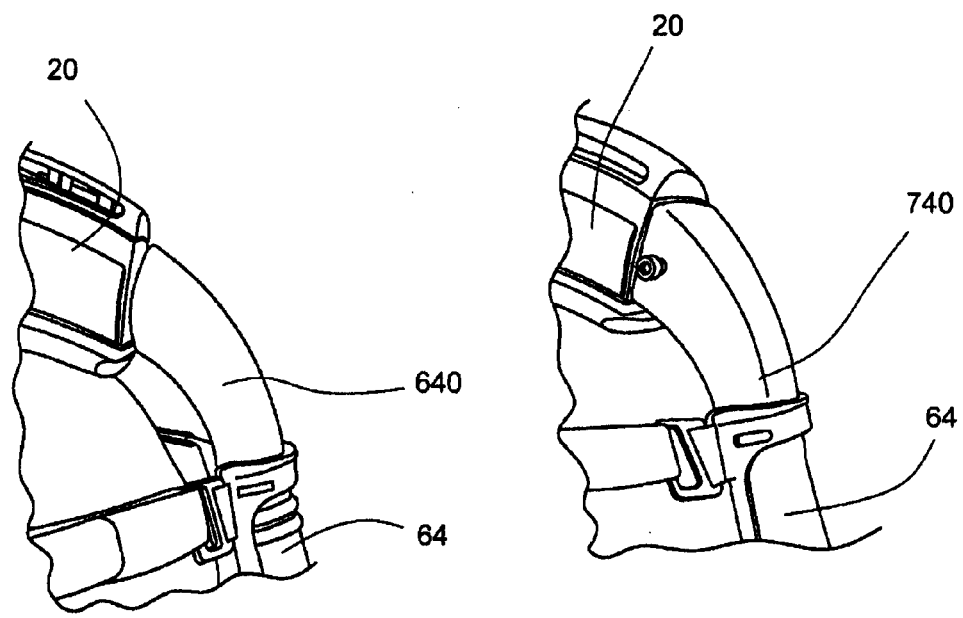
FIG. 49
FIG. 50

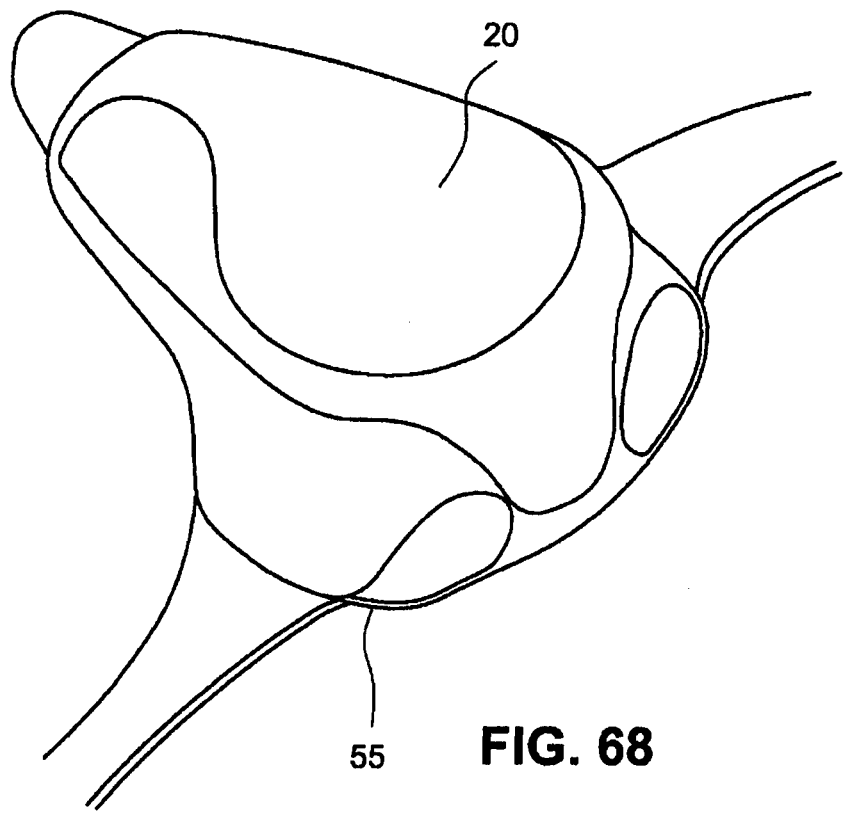
FIG. 68
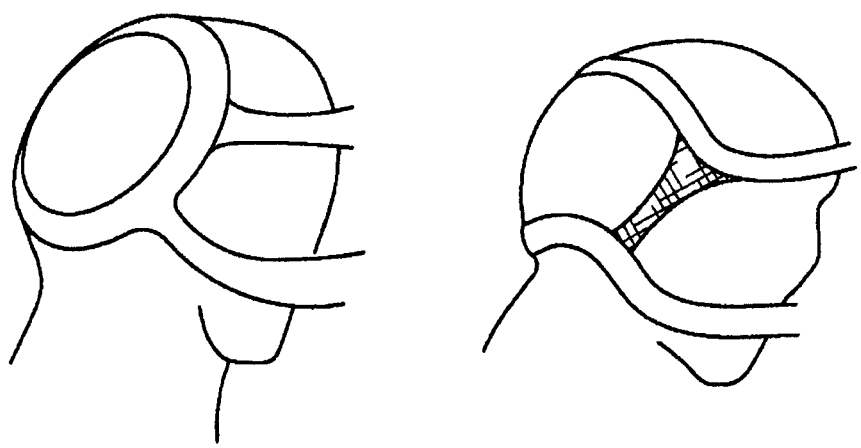
FIG. 69
FIG. 70

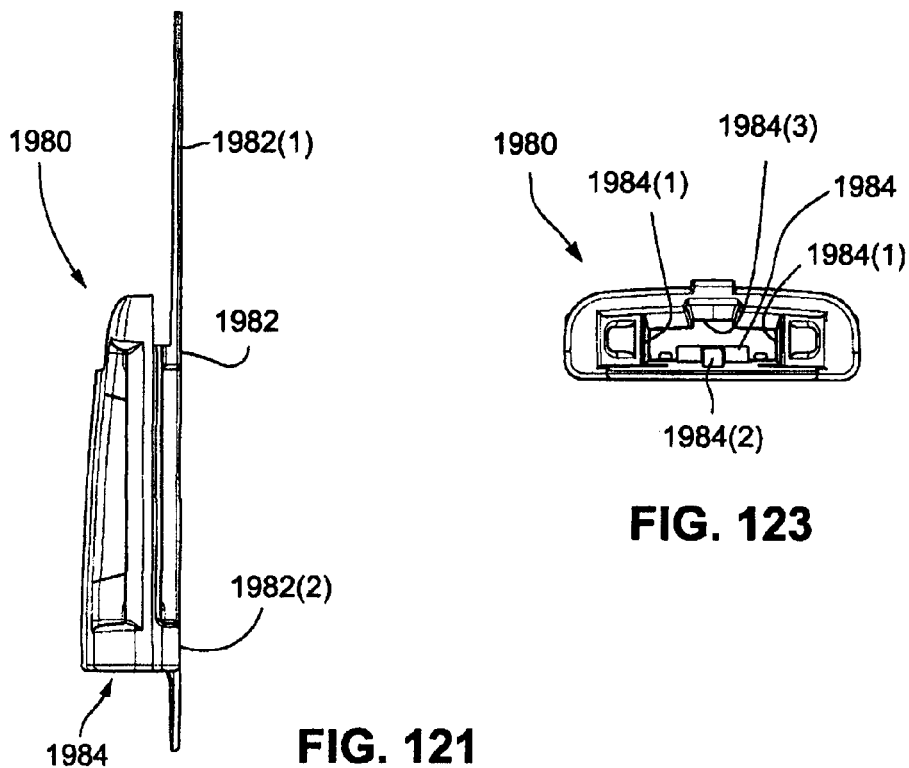
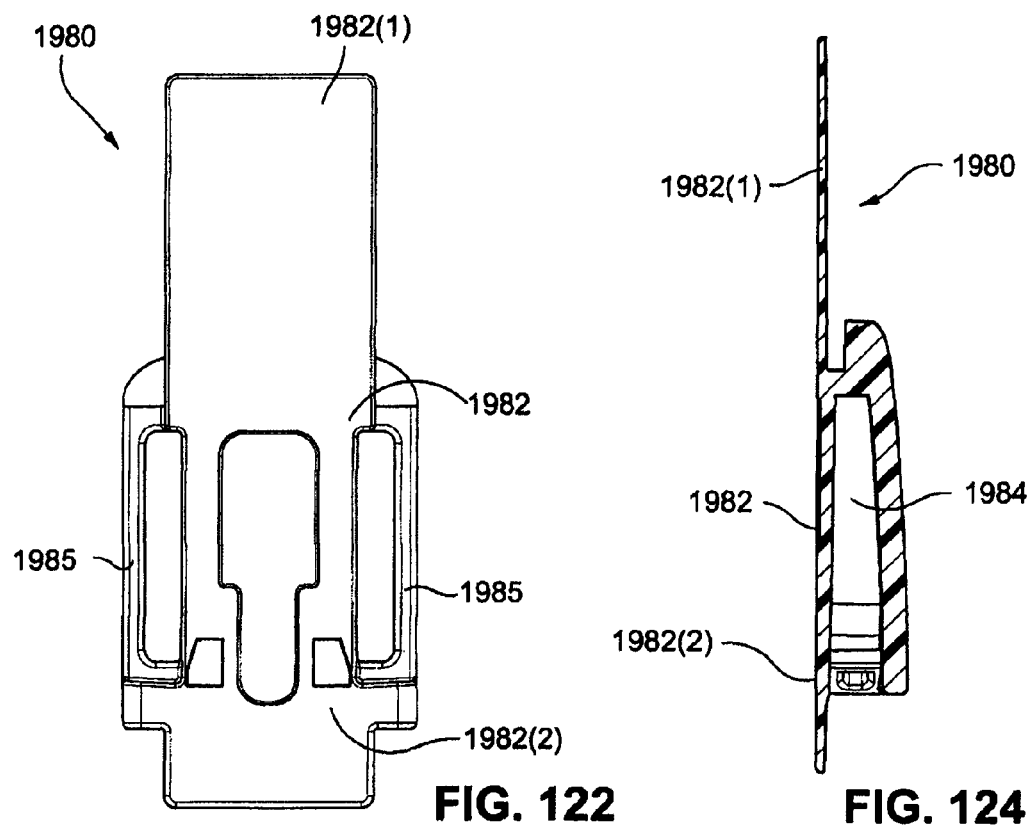

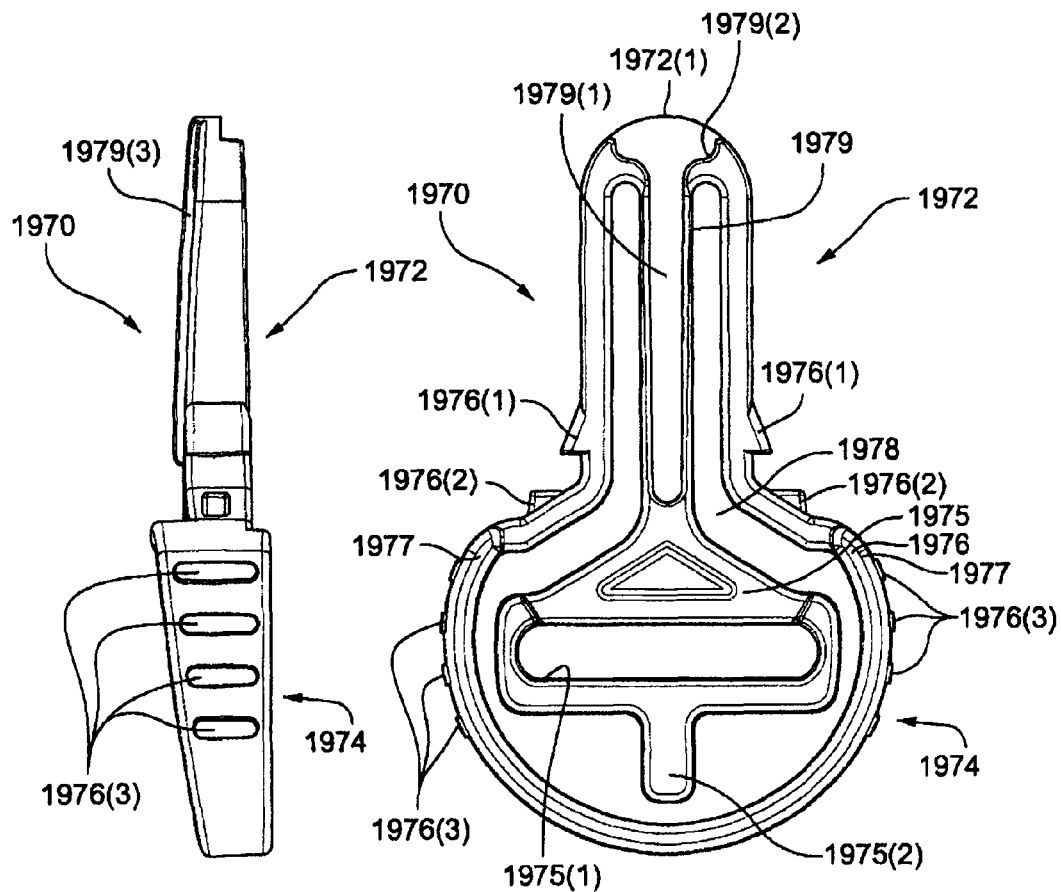
FIG. 127  FIG. 128
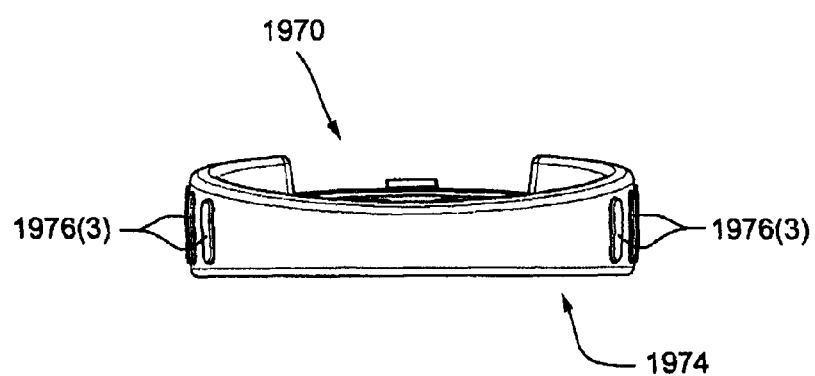
FIG. 129

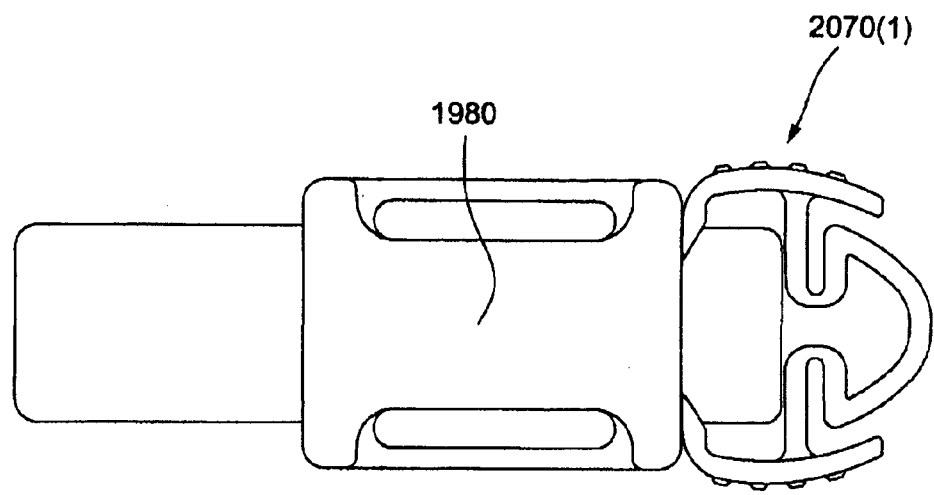
FIG. 132
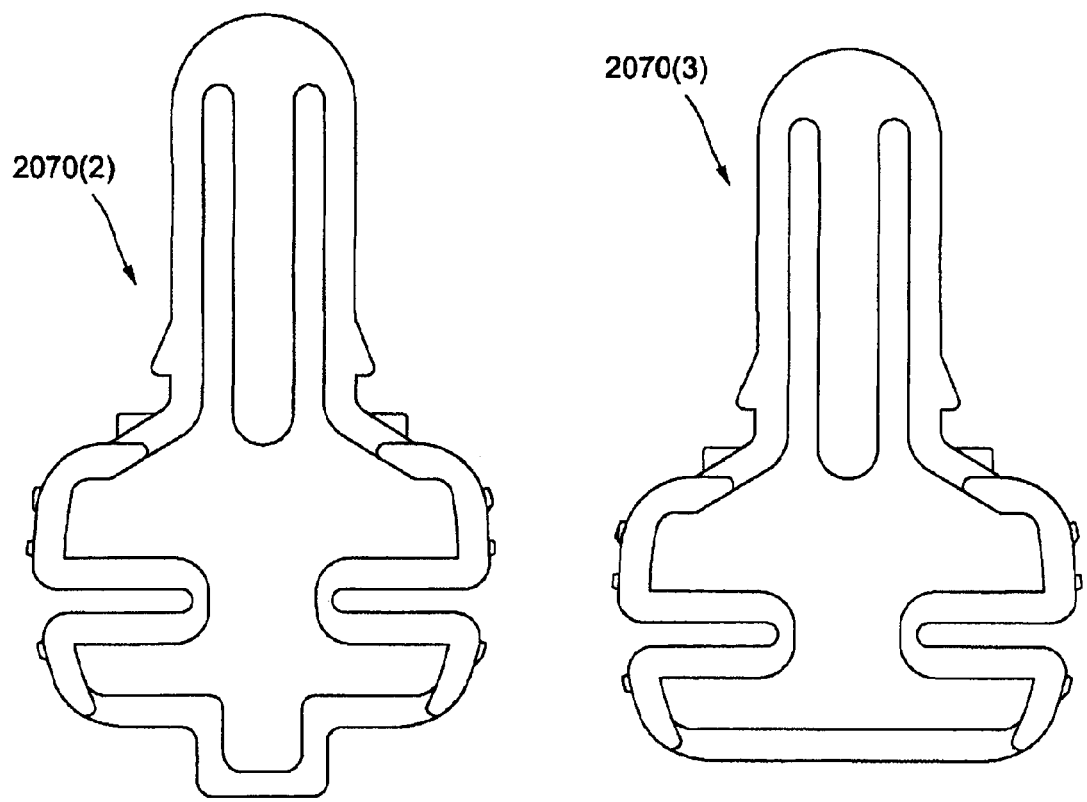
FIG. 133
FIG. 134

PAP SYSTEM

CROSS-REFERENCE TO APPLICATION

This application is the U.S. national phase of International Application No. PCT/AU2011/001107, filed 26 Aug. 2011, which designated the U.S. and claims the benefit to U.S. Provisional No. 61/344,588, filed 27 Aug. 2010, and U.S. Provisional No. 61/457,317, filed 25 Feb. 2011, the entire contents of each of which are hereby incorporated by reference.

FIELD OF TECHNOLOGY

The present technology relates to Positive Airway Pressure (PAP) systems and/or methods of use for treatment, e.g., of Sleep Disordered Breathing (SDB) with Continuous Positive Airway Pressure (CPAP) or Non-Invasive Positive Pressure Ventilation (NIPPV).

BACKGROUND OF TECHNOLOGY

Examples of head mounted blowers, wearable CPAP, or portable CPAP are known in the art. For example, see U.S. Patent Application Publications 2006/0237013 A1 and 2009/0320842 A1, each incorporated herein by reference, and the BreatheX™ system.

SUMMARY OF TECHNOLOGY

One aspect of the disclosed technology relates to a pneumatic connector or the pneumatic connection between the patient interface and another component, e.g., the flow generator, the forehead support, etc. In general, an aspect of the disclosed technology relates to providing stability, comfort, and reasonable adjustment in the region between patient interface and another component.

Another aspect of the disclosed technology relates to a flexible connection (e.g., one or more articulation joints or articulated connectors) between the patient interface and another component (e.g., flow generator, forehead support, etc.) to provide flexibility for the patient interface to fit on different patient's faces.

Another aspect of the disclosed technology relates to an outlet tube assembly between the flow generator and the patient interface, the outlet tube assembly including an outlet tube and top and/or bottom articulated connectors that provide one and/or two articulation points to add flexibility to the top and/or bottom portions of the outlet tube. The articulation system provided by the outlet tube assembly may provide a range of positions to accommodate different forehead shapes and sizes of different patients.

Another aspect of the disclosed technology relates to a PAP system adapted for treatment of respiratory disease or sleep disordered breathing. The PAP system includes headgear adapted to engage a patient's head, a patient interface adapted to be secured to and sealed against a portion of a patient's face, in use, by the headgear, a flow generator adapted to be connected to the patient interface, and wherein the flow generator is adapted to be secured by a portion of the headgear to the patient's head, and an outlet tube to interconnect the flow generator and the patient interface. The patient interface includes a frame and a sealing arrangement supported by the frame. The sealing arrangement includes a seal portion, a body portion, and an inlet tube in communication with the outlet tube. The frame and the outlet tube are constructed of a relatively rigid material.

Another aspect of the disclosed technology relates to a PAP system adapted for treatment of respiratory disease or sleep disordered breathing. The PAP system includes headgear adapted to engage a patient's head a patient interface adapted to be secured to and sealed against a portion of a patient's face, in use, by the headgear, a flow generator adapted to be connected to the patient interface, and wherein the flow generator is adapted to be secured by a portion of the headgear to the patient's head, and an outlet tube assembly to interconnect the flow generator and the patient interface. The outlet tube assembly includes an outlet tube constructed of a relatively rigid material, a top articulated connector constructed of a relatively soft flexible material configured to connect a top portion of the outlet tube with an outlet of the flow generator, and a bottom articulated connector constructed of a relatively soft flexible material configured to connect a bottom portion of the outlet tube with an inlet tube of the patient interface.

Another aspect of the disclosed technology relates to a mask arrangement including a patient interface adapted to be secured to and sealed against a portion of a patient's face in use and an outlet tube constructed of a relatively rigid material configured to receive a supply of pressurized gas from a flow generator in use. The patient interface includes a frame constructed of a relatively rigid material and a cushion supported by the frame. The frame includes an inlet tube in fluid communication with the outlet tube.

Another aspect of the disclosed technology relates to a headgear arrangement including at least one headgear strap, a chin strap, and a clip arrangement structured to engage both the at least one headgear strap and the chin strap.

Another aspect of the disclosed technology relates to a PAP system adapted for providing a supply of pressurized respiratory gas to a patient. The PAP system includes headgear adapted to engage the patient's head, a patient interface adapted to be secured to and sealed against a portion of the patient's face, in use, by the headgear, a flow generator adapted to be connected to the patient interface and to generate a supply of pressurized gas, in use, wherein the flow generator is adapted to be secured by a portion of the headgear to a patient's head, and a tube assembly between the flow generator and the patient interface to deliver the pressurized gas generated by the flow generator to the patient interface. The tube assembly provides a relatively smooth and fixed internal flow path to provide a relatively even and uninterrupted flow for the pressurized gas.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIGS. 6 and 7 show connection of the outlet tube to the flow generator according to an example of the present technology;

FIG. 8 shows the frame and inlet tube of the PAP system of FIG. 4;

FIGS. 13 to 46 show PAP systems including a largely enclosed silicone cushion adapted to interface with rigid molded components according to examples of the present technology;

FIGS. 47 to 55 show alternative examples of the outlet tube and alternative examples for connecting the outlet tube to the flow generator and patient interface according to examples of the present technology;

FIGS. 56 to 79 show alternative examples of headgear according to examples of the present technology;

FIG. 121 is a side view of the clip receptacle of FIG. 119;

FIG. 122 is a bottom view of the clip receptacle of FIG. 119;

FIG. 123 is a rear view of the clip receptacle of FIG. 119;

FIG. 124 is a cross-sectional view of the clip receptacle of FIG. 119;

FIG. 127 is a side view of the headgear clip of FIG. 125;

FIG. 128 is a bottom view of the headgear clip of FIG. 125;

FIG. 129 is a rear view of the headgear clip of FIG. 125;

FIGS. 130 to 132 show a headgear clip according to another example of the present technology;

FIG. 133 shows a headgear clip according to another example of the present technology;

FIG. 134 shows a headgear clip according to another example of the present technology;

DETAILED DESCRIPTION OF ILLUSTRATED EXAMPLES

Figure 1:
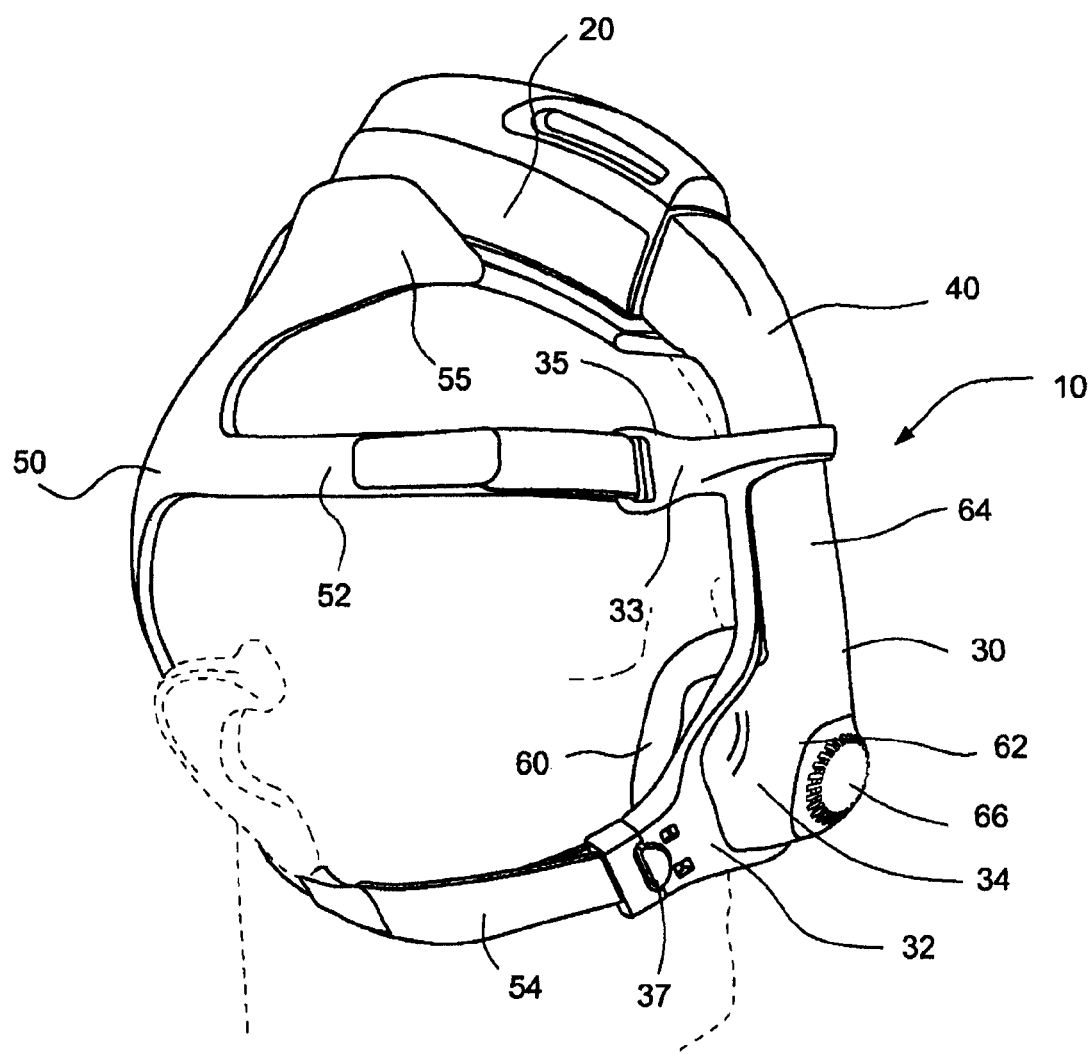
FIG. 1 is a perspective view of a headworn PAP system according to an example of the present technology.

The following description is provided in relation to several examples (most of which are illustrated, some of which may not) which may share common characteristics and features. It is to be understood that one or more features of any one example may be combinable with one or more features of the other examples. In addition, any single feature or combination of features in any example or examples may constitute patentable subject matter.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

The terms "rigid" or "relatively rigid" will be taken to mean not readily deforming to finger pressure and/or tensions or loads typically encountered when setting up and maintaining a patient interface or tubing with an entrance to a patient's airway. A rigid material is considered to have a Young's modulus measure of at least 1 gigapascal (GPa). The terms "semi-rigid" or "relatively semi-rigid" will be taken to mean being sufficiently rigid to not substantially distort under the effects of tube drag and/or is capable of supporting its own weight without distortion.

One or more examples may include exemplary dimensions. Although specific dimensions and ranges may be provided, it is to be understood that these dimensions and ranges are merely exemplary and other dimensions and ranges are possible depending on application. For example, ranges that vary from those provided +/−10% may be suitable for particular applications.

PAP System

A PAP system (e.g., CPAP system) typically includes a PAP device (including a blower for generating air at positive pressure), an air delivery conduit (also referred to as a tube or tubing), and a patient interface. In use, the PAP device generates a supply of pressurized air (e.g., 2-30 cm $H_2O$) that is delivered to the patient interface via the air delivery conduit. The patient interface or mask may have suitable configurations as is known in the art, e.g., full-face mask, nasal mask, oro-nasal mask, mouth mask, nasal prongs, etc. Also, headgear may be utilized to comfortably support the patient interface in a desired position on the patient's face.

Certain examples relate to PAP systems in which the PAP device or blower is adapted to be worn on the patient's head, is built into or incorporated into the patient interface or mask, is wearable or carried by the patient, is portable, is reduced in size or combinations thereof. In certain examples, the blower may be of the types described in International Application PCT/AU2010/001031, filed Aug. 11, 2010, entitled "Single Stage, Axial Symmetric Blower and Portable Ventilator," which is incorporated herein by reference in its entirety.

Exemplary Headworn PAP System

FIG. 1 illustrates a headworn PAP system 10 including a blower or flow generator 20, a patient interface or mask 30 (e.g., nasal mask), and an outlet tube 40 that interconnects the patient interface and the flow generator. Headgear 50 secures the flow generator and patient interface in position on the patient's head in use.

The patient interface 30 includes a frame 32 which supports a sealing arrangement 34. The frame 32 provides a forehead support 33 with upper headgear connectors 35 for engaging upper side straps 52 of the headgear. The frame 32 provides lower headgear connectors 37 for engaging lower side straps 54 of the headgear.

The sealing arrangement 34 includes a cushion or seal portion 60 (e.g., nasal seal), a body portion 62, and an inlet tube or chimney portion 64. The forehead support may engage or hold the inlet tube. The sealing arrangement may include a vent 66 to allow the exhalation of gases from the mask and patient.

The outlet tube 40 includes a first end configured to connect to the outlet of the flow generator 20 and a second end configured to connect to the inlet tube 64 of the sealing arrangement. In an example, the outlet tube may directly engage the inlet tube, e.g., inlet tube received within the outlet tube. Alternatively, a connector tube may be provided to interconnect the outlet tube and the inlet tube. In such arrangement, the connector tube may be supported by the forehead support of the frame.

The headgear 50 includes a cradle 55 structured to engage the underside and/or sides of the flow generator 20 and support the same on the patient's head.

Figure 2:
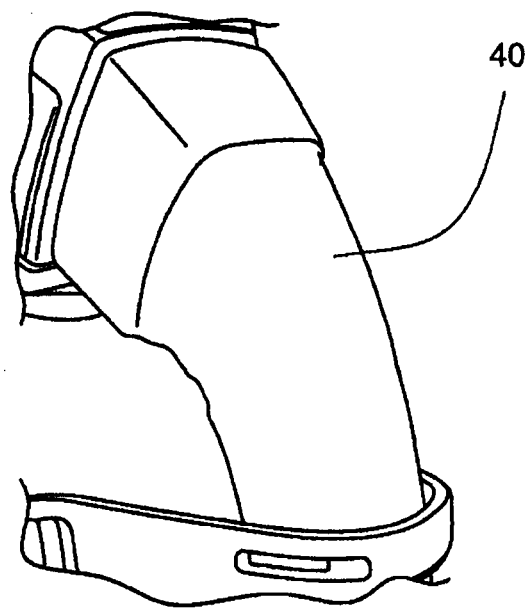
FIG. 2 shows an outlet tube of the PAP system of FIG. 1.
Figure 3:
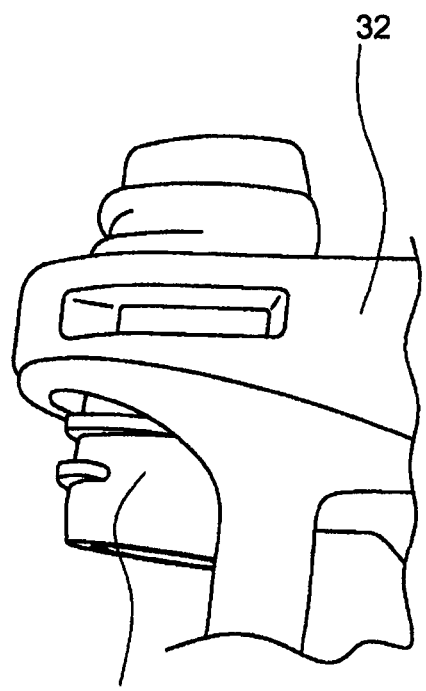
FIG. 3 shows a connector tube of the PAP system of FIG. 1.

FIG. 2 is an enlarged view of an outlet tube 40 (which length may be adjusted to enhance comfort, fit, performance, etc.). FIG. 3 is an enlarged view of the connector tube 39 supported by the frame 32 and adapted to interconnect the outlet tube and the inlet tube.

In this example, the sealing arrangement 34 and the outlet tube 40 are constructed of a relatively soft material (e.g., silicone) and the frame 32 is constructed of a more rigid material (e.g., polycarbonate).

Additional exemplary examples of PAP systems are disclosed in PCT Application No. PCT/AU2010/001106, filed Aug. 27, 2010, entitled PAP System, the entire contents being incorporated herein by reference in its entirety.

Headworn PAP System with Rigid Components

In an alternative example, one or more additional components (e.g., outlet tube, inlet tube) of the PAP system may be constructed of a rigid or semi-rigid material (e.g., polycarbonate, polypropylene, nylon), which may reduce noise transmission. The rigid or semi-rigid material may be formed as a composite of material in which one material is used to reinforce or support another material to provide the rigid or semi-rigid properties required. The rigid components are adapted to provide a relatively smooth and fixed internal airflow path to assist in reducing or dampening the radiated and/or conducted noise. A relatively smooth and fixed internal airflow path provides a relatively even and uninterrupted flow for the pressurized gas from the blower or flow generator to the patient interface or mask. The PAP system may produce a noise range level of approximately 30 dB to 50 dB, such as 35 dB to 45 dB.

For example, the outlet tube may be constructed of a rigid or semi-rigid material (e.g., polycarbonate). In such example, flexible joints may be provided between the outlet tube and the outlet of the flow generator and between the outlet tube and the inlet tube, e.g., to allow some articulation.

Also, the outlet tube may connect to an outlet tube portion extending from the flow generator, or the outlet tube portion may be removed and the connection may be to an outlet within the housing of the flow generator.

The rigid or semi-rigid materials may be overmolded with soft moldings, e.g., to make them more comfortable on the patient's skin.

Also, the relative angle of the inlet tube from the mask and how far off the face the inlet tube extends is generally more acute, but may be adjusted to enhance comfort and performance.

Figure 4:
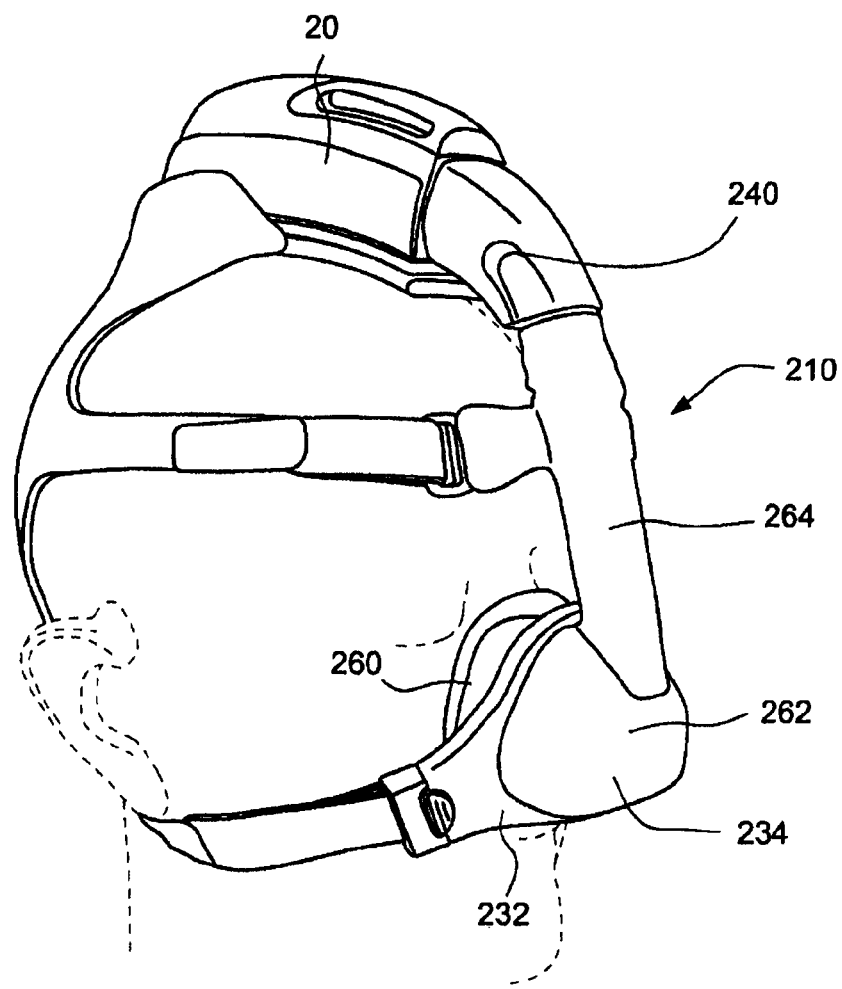
FIG. 4 is a perspective view of a headworn PAP system according to another example of the present technology.

FIG. 4 illustrates a PAP system 210 in which the frame 232, and the body portion 262 and the inlet tube 264 of the sealing arrangement 234 are constructed of a rigid or semi-rigid material (e.g., polycarbonate) and the cushion 260 is constructed of a silicone material. Also, the outlet tube 240 may be constructed of a rigid or semi-rigid material (e.g., polycarbonate). The vent may also be a constructed of a rigid or semi-rigid material such as polypropylene or polycarbonate. The vent may include any of the noise reducing vent designs described in U.S. Patent Application Publication No. 2009/0050156, published Feb. 26, 2009, which is incorporated herein by reference in its entirety.

Figure 5:
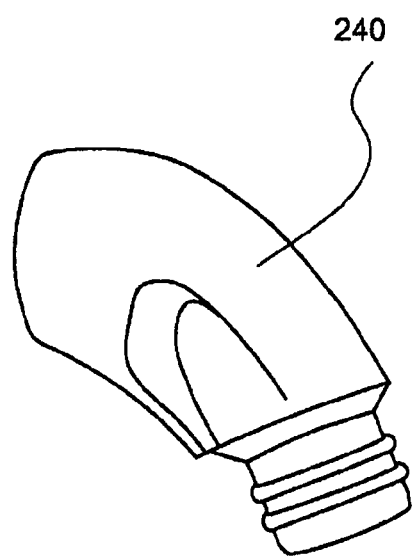
FIG. 5 shows an outlet tube of the PAP system of FIG. 4.

FIG. 5 is an enlarged view of an outlet tube 240. FIGS. 6 and 7 are views showing the connection of the outlet tube 240 to the flow generator 20. As illustrated, the outlet 21 within the housing of the flow generator may be separated from the housing and may be shaped or structured to allow up and down rotation. The outlet may act as a flexible hinge while still maintaining its original function as a sealed air conduit between the flow generator and the outlet tube 240.

FIG. 8 shows the rigid frame 232 and rigid body portion 262 and inlet tube 264. In this example, the inlet tube may be connected to or otherwise interact with the mask frame at an upper region of the mask frame, while also being positioned towards the front or away from the mask to cushion connection. This may enhance the volume of inspired oxygen from the air by positioning the inlet closer to the patient's nares. Thus, the inlet tube may be positioned closer to the mask interface channel and the angle relative to the line of draw may be more acute resulting in improved comfort and performance of the mask.

Figure 9:
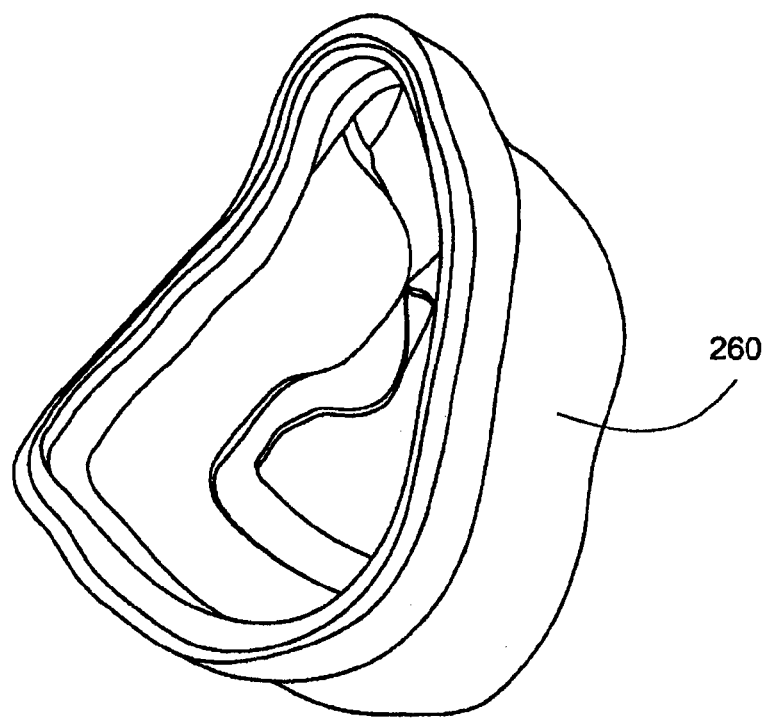
FIG. 9 shows a cushion of the PAP system of FIG. 4.
Figure 10:
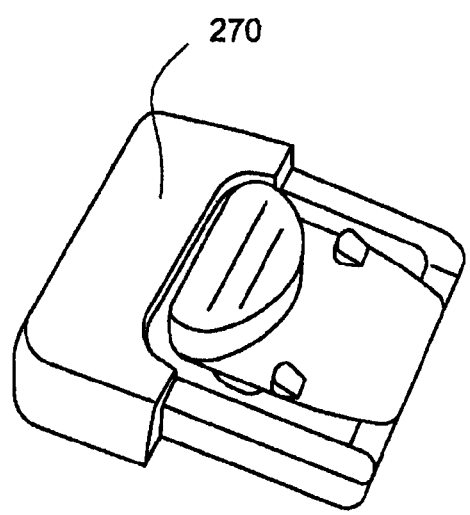
FIG. 10 shows a headgear clip of the PAP system of FIG. 4.

FIG. 9 shows an example of the cushion 260 including an interface bead for sealing with the frame. An exemplary cushion is disclosed in WO 2010/135785, published Dec. 2, 2010, which is incorporated herein by reference in its entirety. An exemplary cushion to frame engagement bead is disclosed in U.S. Patent Application Publication No. 2008/0276937, published Nov. 13, 2008, which is incorporated herein by reference in its entirety. FIG. 10 shows an example of a headgear clip 270 for attaching headgear straps to the frame. An exemplary headgear clip is disclosed in U.S. Pat. No. 6,374,826, granted Apr. 23, 2002, which is incorporated herein by reference in its entirety.

The following provides alternative examples of PAP systems structured to provide a more rigid air flow path between the flow generator and the cushion.

Figure 11:
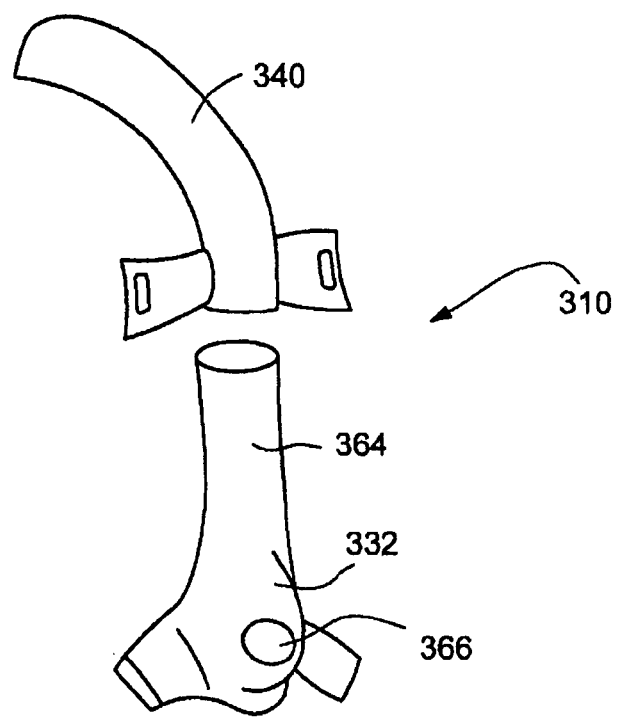
FIGS. 11 and 12 show PAP systems including a rigid and integrated frame and inlet tube according to examples of the present technology.
Figure 12:
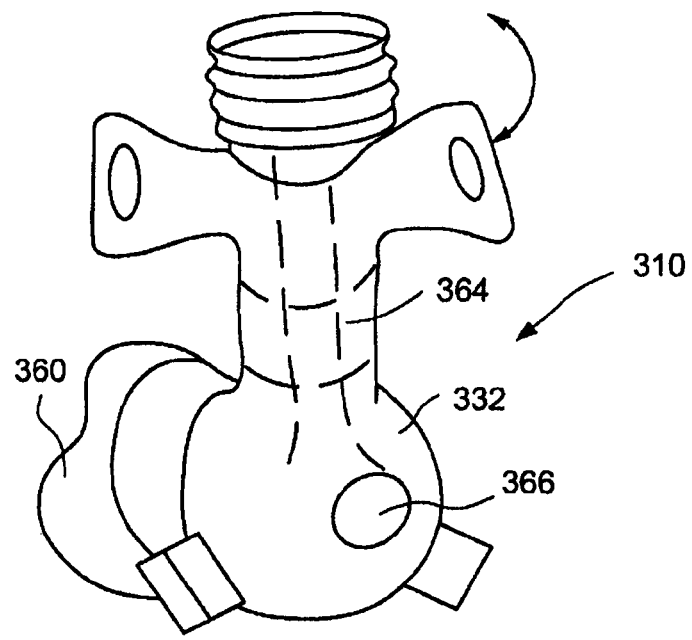
Figure 20:
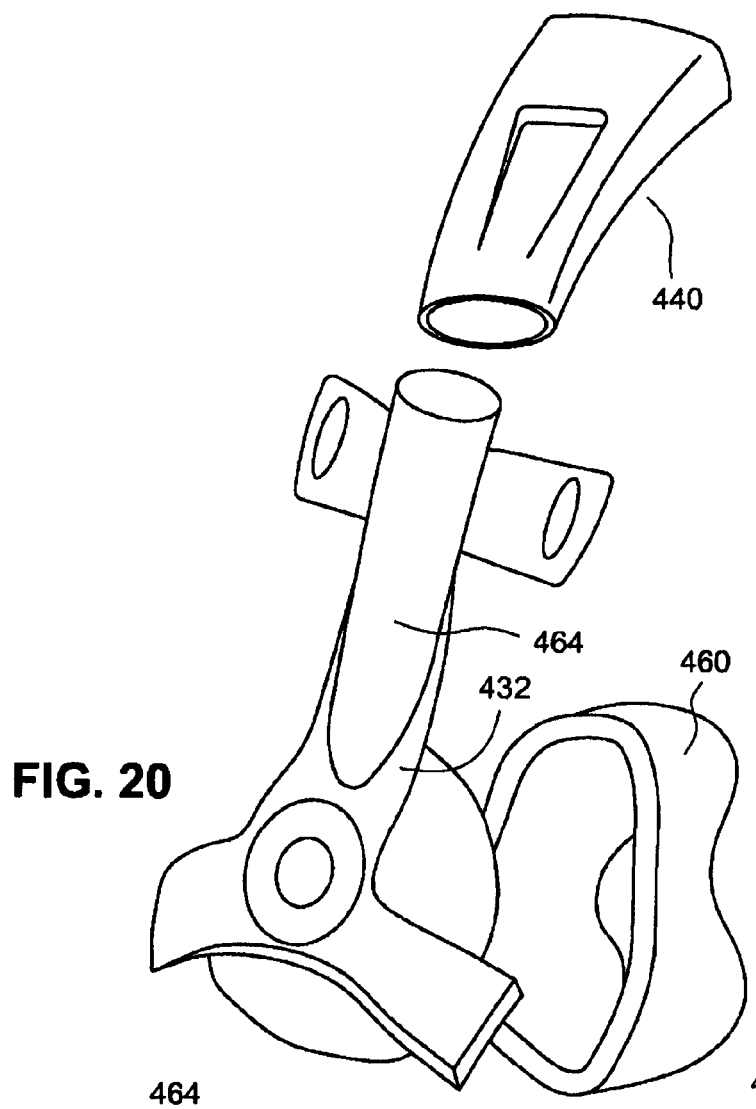
Figure 21:
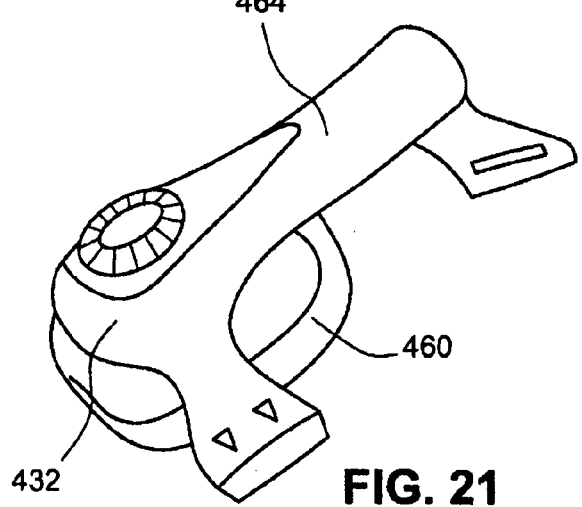
Figure 22:
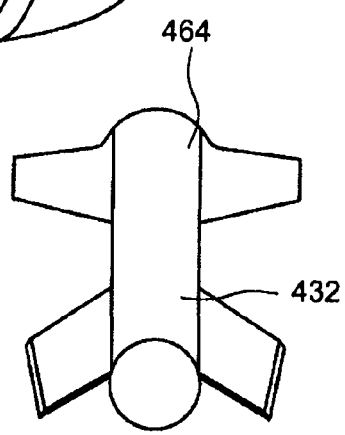

For example, FIGS. 11 and 12 illustrate PAP systems 310 each including a rigid and integrated frame 332 and inlet tube 364. The rigid and integrated frame and inlet portion includes a vent 366. In FIG. 11, lower headgear connectors are provided to the integrated frame and inlet portion, and upper headgear connectors are provided to the outlet tube 340. In FIG. 12 upper and lower headgear connectors are provided to the integrated frame and inlet portion. The integrated frame and inlet portion is structured to support a push-on style cushion 360. A flexible connection, e.g., such as a concertina connection, may be provided at the connection point between the rigid and integrated frame and inlet portion and the rigid outlet tube 340 to provide flexibility for the mask to fit on different users faces. Any flexible connection may be used, e.g., one or more articulation joints may be utilized. FIG. 20 shows a similar design to that shown in FIG. 12 where an integrated frame 432, inlet tube 464, forehead support and headgear clip receptacles or attachment points are all formed in a single component and then a cushion 460 is attached to the frame via a perimeter bead adapted to be retained within a frame channel. The forehead support may also include apertures adapted to receive upper headgear straps, the apertures being located at the ends of the forehead support. FIG. 21 is a side perspective view of this mask example. FIG. 22 shows the frame incorporating the lower headgear clip receptacles and a forehead support. The forehead support may also include upper headgear clip receptacles.

FIGS. 13-46 illustrate examples of PAP systems including a largely enclosed silicone cushion adapted to interface with rigid molded components providing the frame, inlet portion, vent, headgear connectors, etc. For example, FIGS. 13-46 illustrate various views and examples of a rigid frame 432 adapted to interface with a cushion 460, rigid inlet tube 464, and/or a rigid outlet tube 440.

FIGS. 13 to 15 show an example of the patient interface unit having a frame 432 to which a cushion is attached and an inlet tube 464 is connected to the frame. The cushion may include a number of interfacing structures adapted to interface or allow removable connection with the frame 432. The cushion also includes an inlet tube interface adapted to allow connection of the inlet tube of the mask. The connection of the inlet tube to the cushion may be a removable connection. The inlet tube may also attach to an upper portion of the rigid frame. The inlet tube may be a rigid tube that may also include a forehead support integrated with the tube. An articulation point such as a concertina or flexible joint may be located at or above the forehead support and provide flexible movement to allow adjustment of the mask to fit different user's forehead shapes. A rigid outlet tube 440 is attached to the opposite side of the articulation point. The outlet tube 440 is adapted to connect to the outlet of the flow generator. A vent and headgear straps may also be connected to the cushion as shown in the figures. Frame 432 may be constructed of a first material and a second material. The first material may form the body of the frame and the second material may form the structure or supporting portions of the frame. Preferably, the second material may be harder or stiffer than the first material. The second material may be formed as spines, inserts or braces, as shown on FIG. 13.

Figure 16:
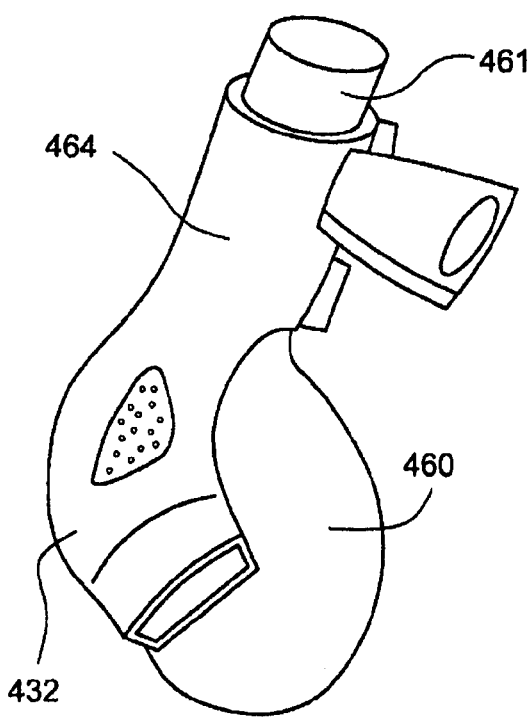
Figure 17:
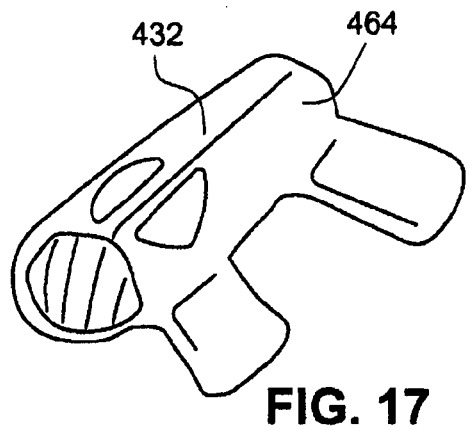

In an alternative example shown in FIG. 16, a rigid frame 432 including an inlet tube 464, vents, a forehead support and headgear clip receptacles are attached to a cushion 460 including a soft tube 461, such as a silicone tube. The soft tube 461 is encapsulated or surrounded by the rigid inlet tube 464 of the frame 432. The forehead support may be formed by a pair of living hinges to provide flexibility in movement as shown in FIG. 17. Vents may be formed in the frame, or may be separately attachable to the frame for example by clipping a vent insert into the frame.

Figure 18:
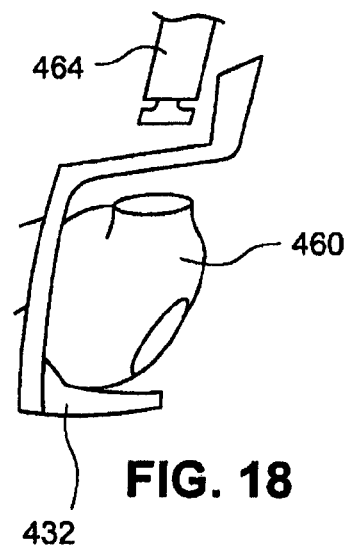
Figure 19:
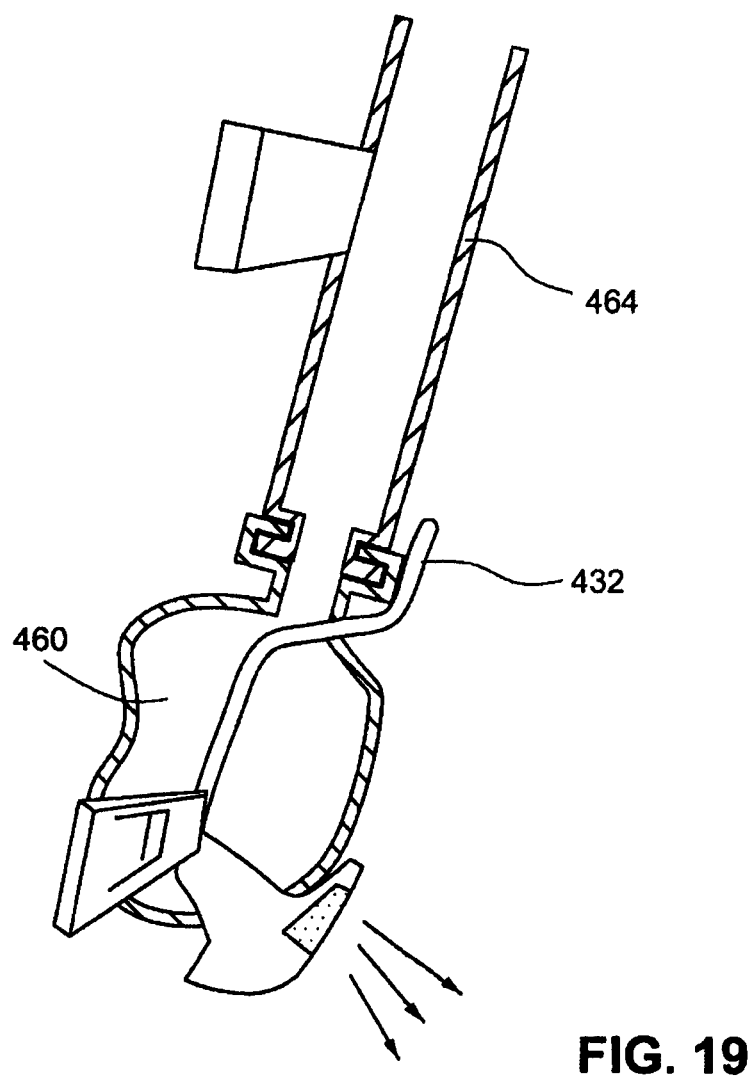

FIG. 18 shows an example of a rigid frame 432 that attaches to cushion 460 and an inlet tube 464 is removably attached to the cushion 460 and frame 432, e.g., via a locking mechanism. FIG. 19 shows inlet tube connected to the frame 432 and cushion 460 using a catch and lock mechanism. A forehead support may be attached to the inlet tube 464 as shown. The inlet tube may be further connected to an outlet tube that is attached to the flow generator. A vent may also be incorporated into the frame 432.

FIGS. 23 to 28 show an example of the mask having a rigid frame 432 to support the cushion 460. The mask is formed from the assembly of three components, the cushion 460, the frame 432 and the inlet tube 464 as indicated in FIG. 24. The frame may include headgear clip receptacles configured to attach to headgear clips. The cushion may be attached to the frame and a vent portion 466 of the frame may be inserted into a vent aperture within a front portion of the cushion 460. The inlet tube 464 may be attached to the cushion 460 and frame 432 by inserting a ribbed interface 464(1) through an aperture in the frame and cushion as indicated in FIG. 27. The frame 432 seals the cushion 460 around the ribbed interface 464(1) of the inlet tube 464 as shown in FIG. 27. FIG. 28 shows an example of the cushion 460.

Figure 29:
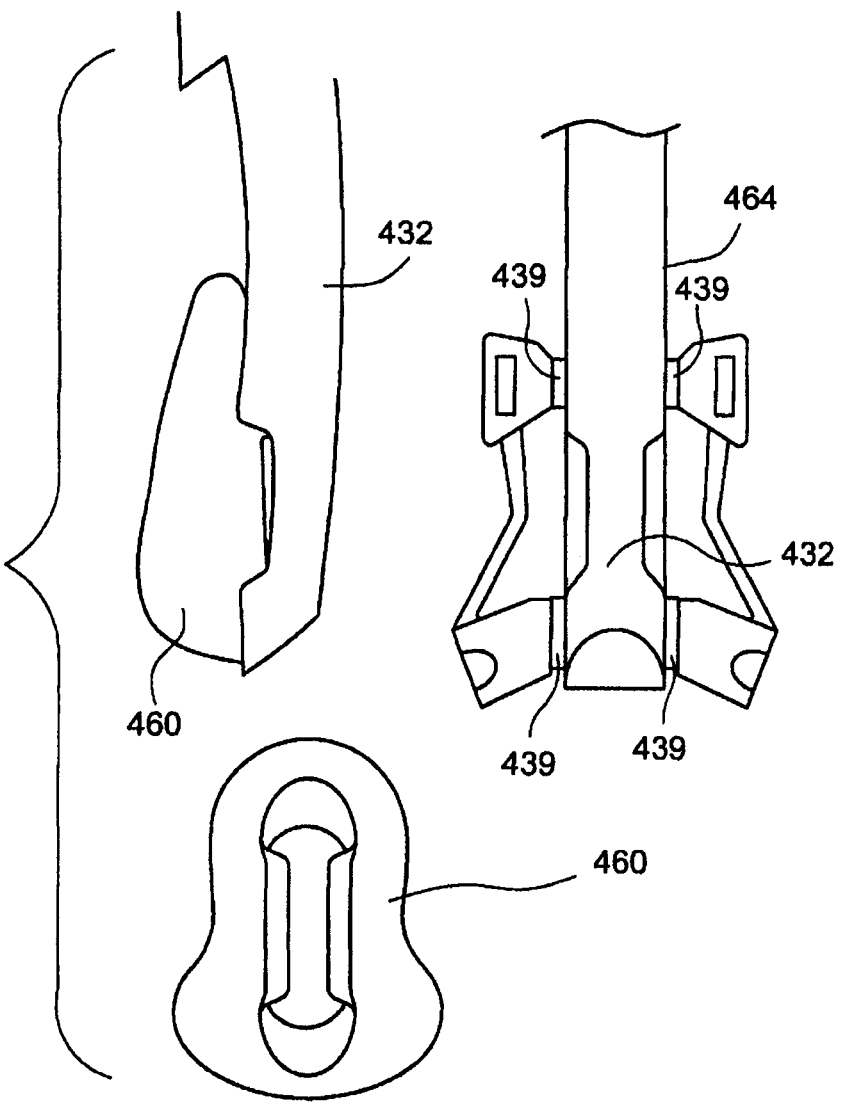

FIG. 29 shows an alternative frame arrangement wherein the forehead support and headgear clips are integrated with the frame 432 in a manner to provide a living hinge 439 at each of the points where the forehead support and/or headgear clip receptacle attaches to the central portion of the frame. The living hinges allow the forehead supports and/or headgear clip receptacles to flex as required to fit a user's face. The inlet tube 464 may be formed in an upper section of the frame. The cushion 460 may be attached to the frame.

FIGS. 30 and 31 show an example with a rigid or semi-rigid frame 432 integrated with a rigid or semi-rigid inlet tube 464 (e.g., polycarbonate). A cushion 460 may be attached to the frame. A flexible or semi-rigid outlet tube 440 may be attached to the inlet tube 464. For example, the outlet tube 440 may be formed of silicone. The outlet tube 440 is connected to the flow generator positioned on the user's head and configured to deliver pressurized gas from the flow generator to the mask cushion, via the inlet tube, for delivery to the user.

Figures 33, 34:
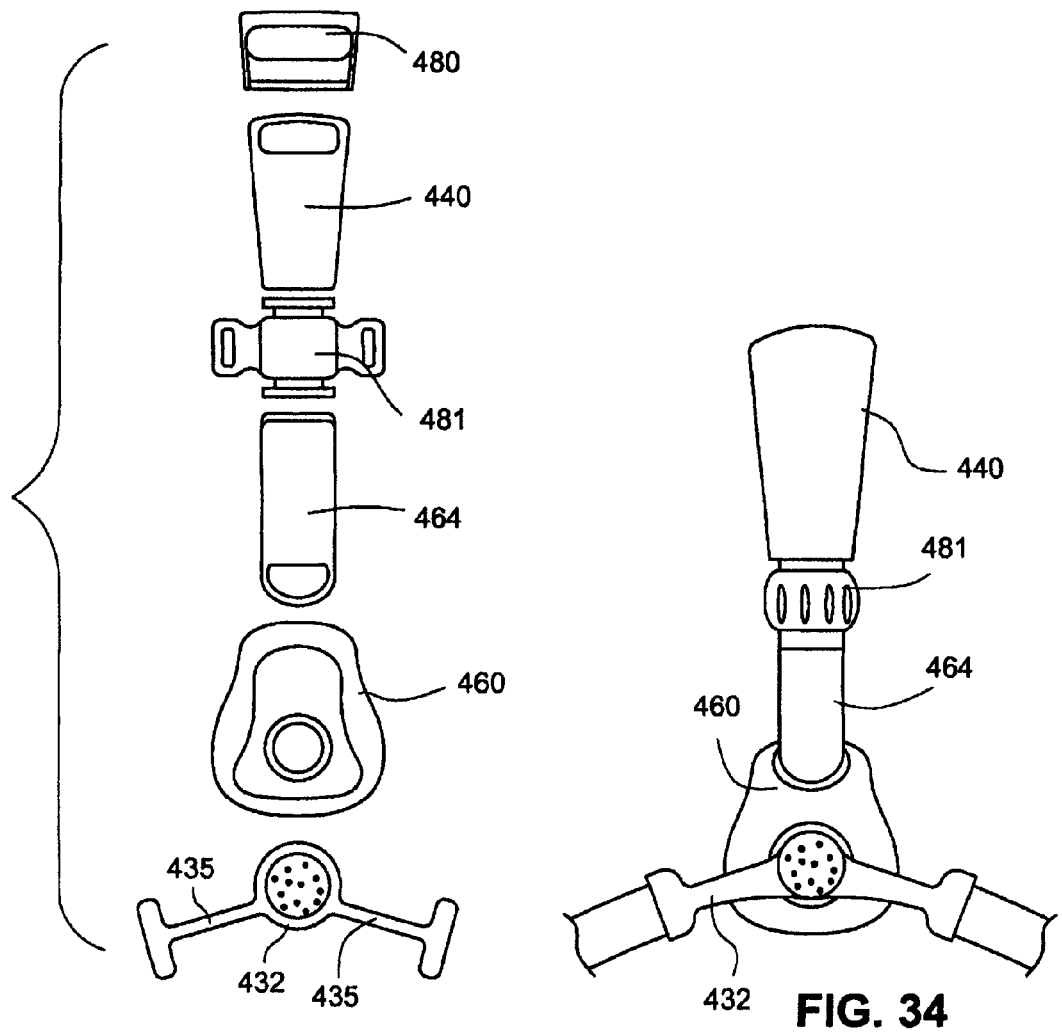

In FIGS. 32 and 33, connector portions 480 and 481 and cushion 460 may be relatively soft (e.g., silicone), while outlet tube 440, inlet tube 464, and frame 432 are relatively rigid or semi-rigid (e.g., polycarbonate). The frame 432 may include headgear connector portions 435 that provide attachment means for headgear straps. Headgear connector portions 435 may be flexible to permit adjustment of the angle of the headgear straps with respect to the patient's face. Preferably, headgear connector portions 435 may extend beyond the perimeter of the cushion 460 so that when headgear straps are connected to the headgear connector portions 435, the cushion 460 is not collapsed or deformed due to contact with the headgear straps. As shown in FIG. 33, the frame 432 may include a vent portion adapted to connect to the cushion 460 and provide a means for exhausted gases to exit the cushion 460. The frame 432 may have the venting portion proximal to the center of the body of the frame 432. The venting portion may be formed of a rigid or semi-rigid material.

Figure 35:
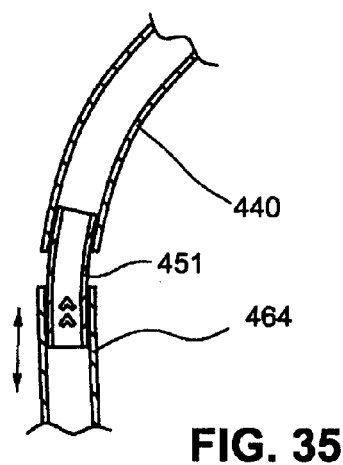

In FIGS. 34 and 35, connector portion 481, outlet tube 440, inlet tube 464, and frame 432 may be constructed of a relatively rigid material. The connector portion 481 may be structured to adjust the relative position of the outlet and/or inlet tubes 440, 464 (e.g., see FIG. 35) to one another. Connector portion 481 may aid adjustment of the position of inlet tube 464 relative to outlet tube 440, for example by a rotating mechanism. For example, the rotation of connector portion 481 may cause one of the inlet tube 464 and outlet tube 440 to telescope or slide inside of the alternate tube. A coupling tube 451 between the outlet tube 440 and the inlet tube 464 may be adjusted by the connector 481. For example, coupling tube may cause one or both of the inlet tube 464 and outlet tube 440 to slide along the coupling tube. The frame 432 may have a vent or other venting means to permit the flow of exhaled gases from inside the mask to atmosphere. Frame 432 may also include a rotating mechanism to adjust the position of the vent or other venting means, e.g., the patient may be able to twist or rotate the rotating portion to position the vents away from their bed partner. The frame 432 may include headgear connector portions structured to couple to headgear straps to assist in retaining the mask on the patient's face in use.

Figure 36:
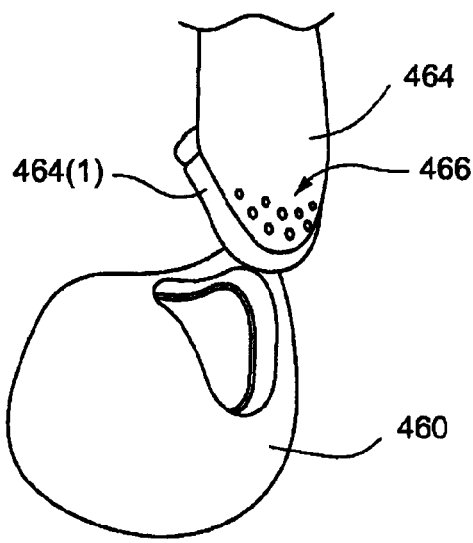
Figure 37:
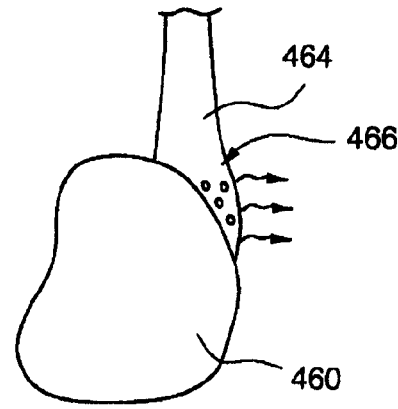
Figure 38:
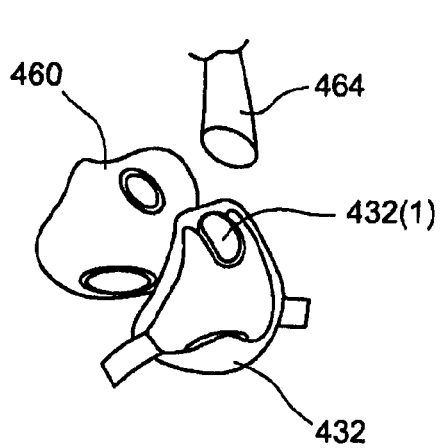

FIGS. 36 to 38 show a further example of a mask arrangement having a separate inlet tube 464 configured to attach to the frame 432 and cushion 460. The inlet tube 464 may be attached to the frame 432 by insertion into an aperture 432(1) at the front of the frame and a bead on the inner surface of the aperture inserting into a channel 464(1) at the end of the inlet tube 464. The cushion 460 is attached to the frame from the opposite side to the inlet tube. Connection of the inlet tube 464 to the frame 432 also provides a sealed connection between the cushion and the inlet tube. The inlet tube wraps down at the front of the frame. A vent portion 466 may be formed in the lower portion of the inlet tube 464 as shown in FIGS. 36 and 37. Alternatively, a vent portion may be incorporated into another portion of the frame 432 (not shown). The vent may be formed of a relatively rigid or semi-rigid material. The cushion 460 is supported by the rigid frame 432.

Figure 39:
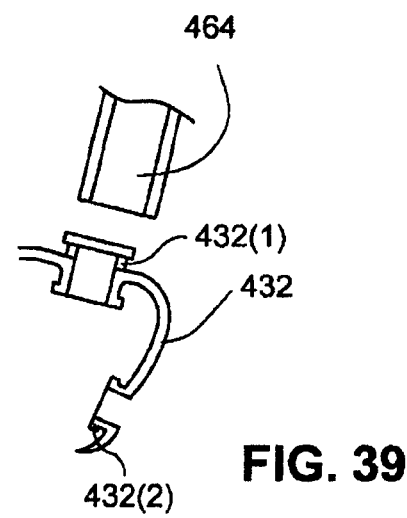
Figure 40:
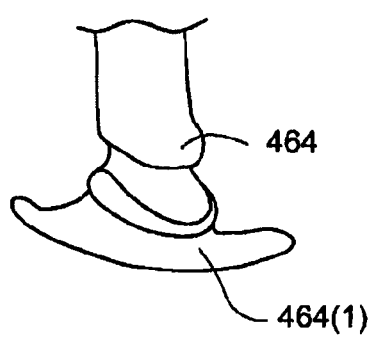

FIGS. 39 and 40 show further examples of mask arrangements. FIG. 39 illustrates a frame 432 including a first connector 432(1) providing opposing tube portions to connect to the inlet tube 464 and to an upper aperture in the cushion 460, and a second connector 432(2) to connect to a lower aperture in the cushion 460. The second connector 432(2) and/or lower aperture may also support a vent. In FIG. 40, the inlet tube 464 may provide an enlarged end portion 464(1) structured to engage or otherwise interface with the frame and/or cushion. The enlarged end portion may be flexible to provide flexibility between the frame and/or cushion.

Figure 41:
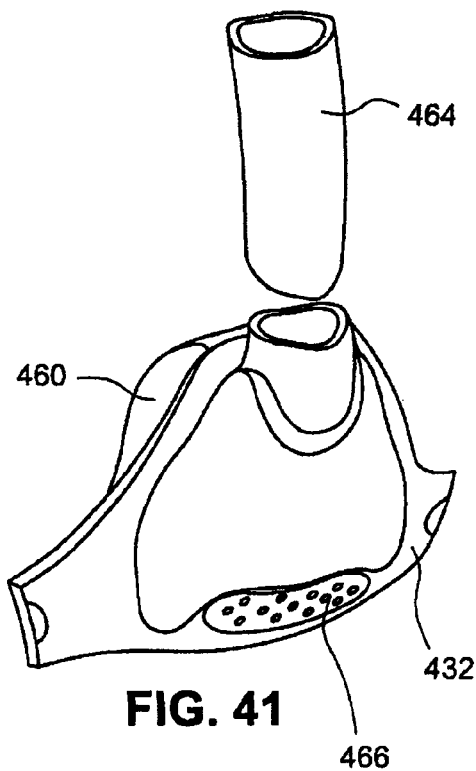
Figure 42:
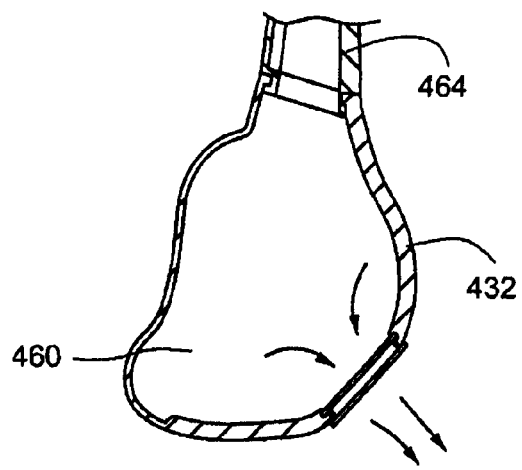

In FIG. 41, a vent 466 may be provided to the frame 432. Also, the cushion 460 may include a small extension to engage the harder inlet tube 464. FIG. 42 indicates how the exhaled gas is vented out through the vent in the mask when the outlet tube 464 is connected to the frame 432 and cushion 460.

Figure 43:
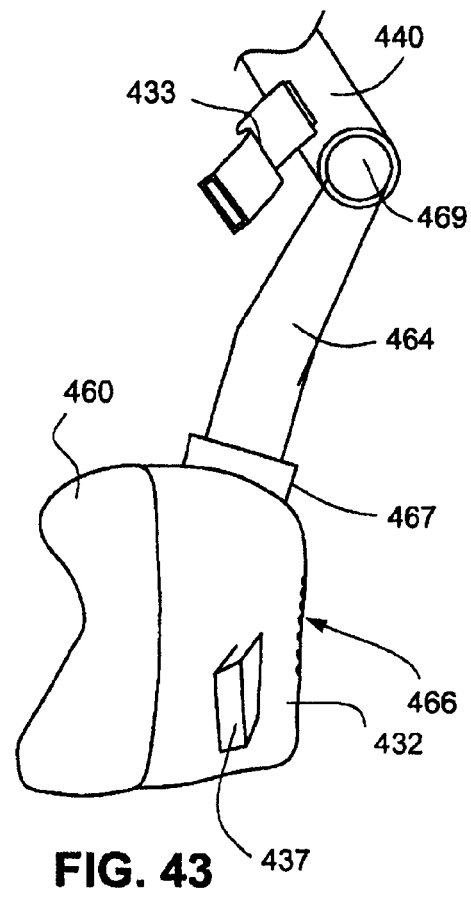

In FIG. 43, the PAP system includes a silicone cushion 460, a rigid or semi-rigid frame 432, lower headgear connectors 437 (e.g., clip receptacles) provided to the frame to connect lower headgear straps, a vent 466 provided to the frame, a first joint 467 to connect a rigid inlet tube 464, and a rigid outlet tube 440 having one end coupled to the flow generator and another end coupled to the inlet tube 464 by a second joint 469. Preferably, second joint 469 and/or first joint 467 may be a ball joint. Alternatively, second joint 469 and/or first joint 467 may be a hinge joint. An upper headgear connector 433 to connect upper headgear straps may be provided to the outlet tube 440 (as illustrated) or to the inlet tube 464 (not shown).

Figure 44:
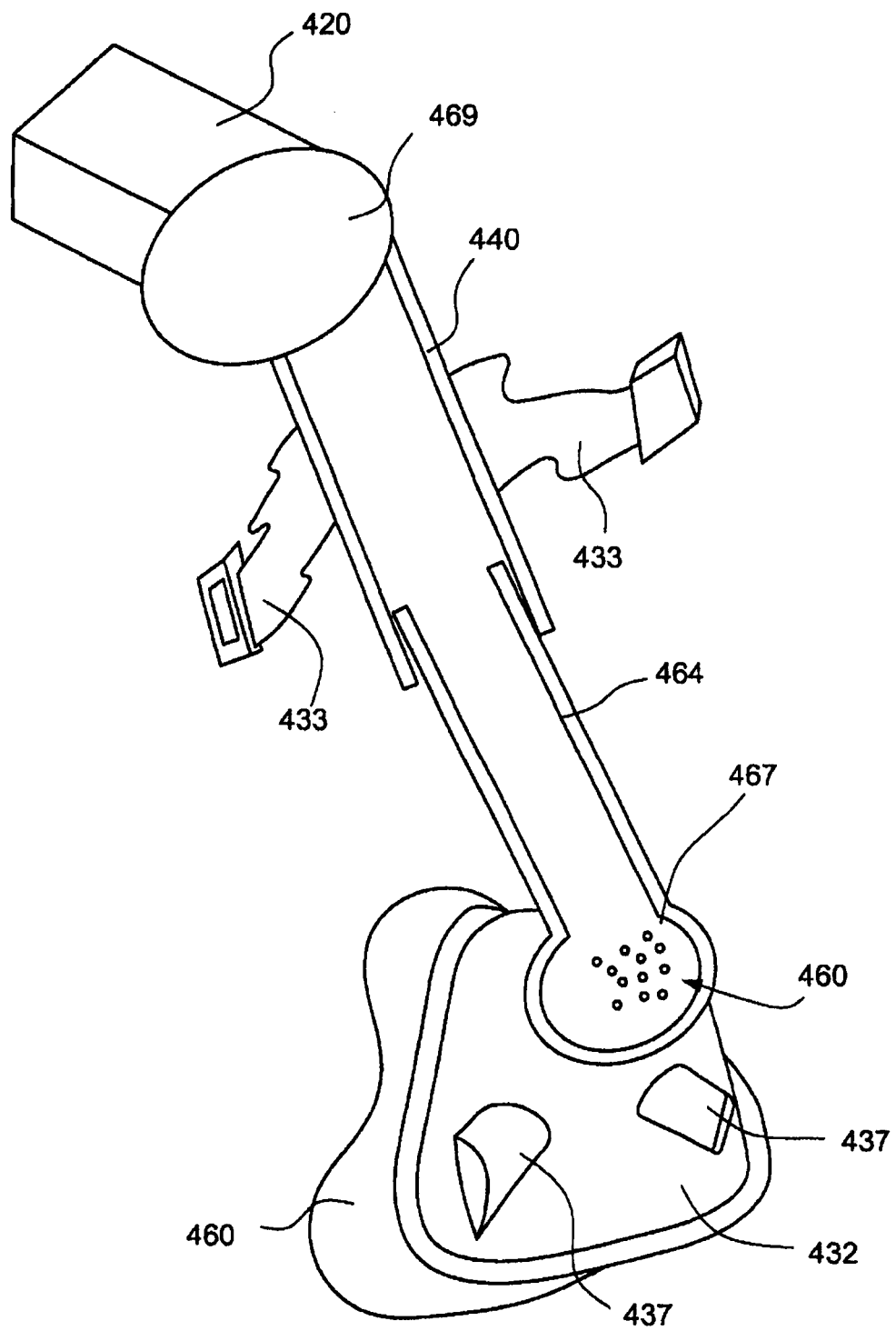

In FIG. 44, the PAP system includes a silicone cushion 460, a rigid frame 432, lower headgear connectors 437 (e.g., clip receptacles) provided to the frame to connect lower headgear straps, a rigid inlet tube 464 coupled to the frame by a ball joint 467 (e.g., ball joint includes vent 466), and a rigid outlet tube 440 having one end coupled to the flow generator 420 by a ball joint 469 and another end slidably coupled to the inlet tube 464 for slidable adjustment. The slidable adjustment enables the combined length of the inlet tube and the outlet tube to adapt to different forehead heights. A flexible upper headgear connector 433 to connect upper headgear straps may be provided to the outlet tube 440.

Figure 45:
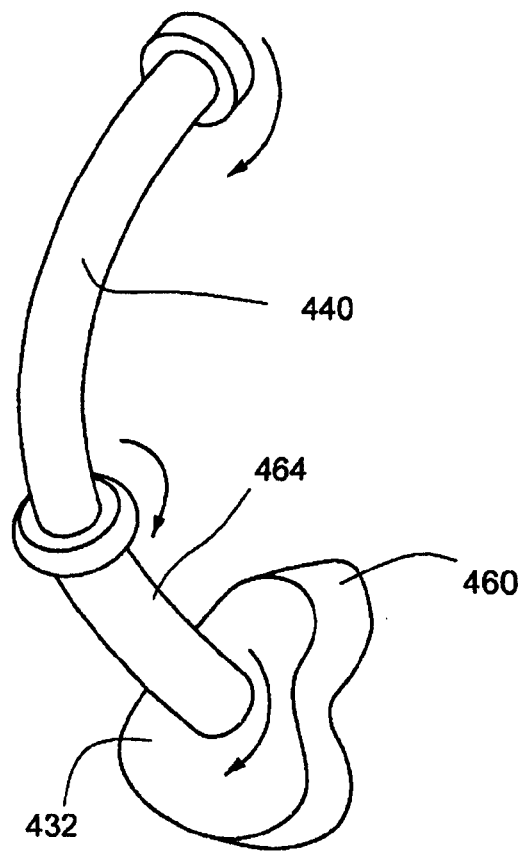

In FIG. 45, the PAP system includes a cushion 460, a frame 432, inlet tube 464, and outlet tube 440. The frame, inlet tube, and outlet tube are rotatably coupled to one another for rotatable adjustment. In an example, the outlet tube and inlet tube may be constructed of hard nylon molded with rigid material connections.

Figure 46:
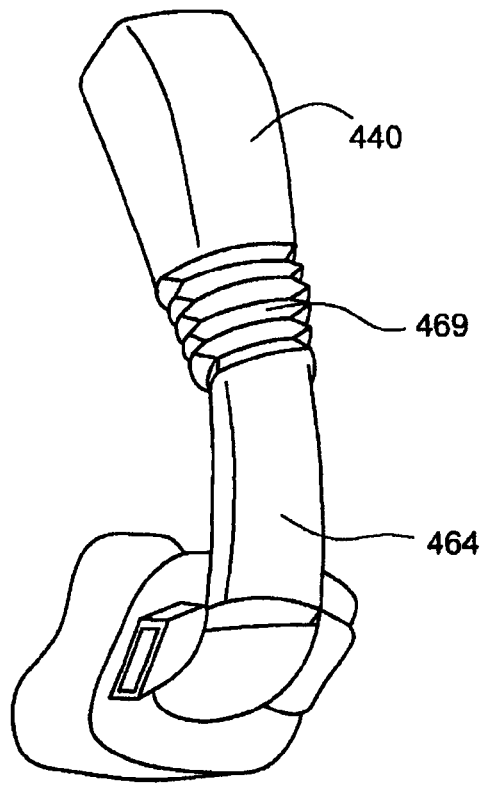

In FIG. 46, the outlet tube 440 may be constructed of clear nylon and a joint 469 may be provided to connect the outlet tube with the inlet tube 464. As illustrated, the joint 469 may be corrugated or flexible to allow length adjustment and rotation.

FIGS. 80-84 show a headworn PAP system 1510 according to another example of the present technology. As illustrated, the headworn PAP system 1510 includes a patient interface 1530 adapted to be secured to and sealed against a portion of the patient's face, in use, by headgear, a flow generator 1520 adapted to be connected to the patient interface and secured by a portion of the headgear to the patient's head (e.g., on the head forward of the crown), and an outlet tube assembly 1540 that interconnects the patient interface and the flow generator (e.g., outlet tube assembly may also be referred to as a forehead tube assembly as it is positioned over the patient's forehead in use).

The patient interface 1530 includes a relatively rigid frame 1532 which supports a cushion 1560 (e.g., nasal seal). The frame 1532 includes a body portion 1534 defining a breathing chamber, an inlet tube 1564, a forehead support 1533 with upper headgear connectors 1535 (e.g., including slots) for engaging upper side straps of the headgear, and lower headgear connectors 1537 (e.g., including clip receptacles for engaging headgear clips 1570) for engaging lower side straps of the headgear. The body portion 1534 may include a vent 1566 to allow the exhalation of gases from the mask and patient. The vent may be formed of a rigid or semi-rigid material to reduce noise.

Outlet Tube Assembly

The outlet tube assembly 1540 is configured to interconnect the outlet 1521 (e.g., see FIGS. 83 and 84) of the flow generator 1520 and the inlet tube 1564 of the patient interface 1530. In the illustrated example, as shown in FIGS. 80 to 91, the outlet tube assembly 1540 includes a relatively rigid outlet tube 1542, an upper or top articulated connector 1544 (also referred to as an upper or top knuckle) configured to connect an upper end or top portion 1543 of the outlet tube 1542 with the outlet 1521, and a lower or bottom articulated connector 1546 (also referred to as a lower or bottom knuckle) configured to connect a lower end or bottom portion 1545 of the outlet tube 1542 with the inlet tube 1564. In an example, all the connection interfaces include a relatively soft material engaged with a relatively hard material to provide a good seal.

The top and bottom articulated connectors 1544, 1546 provide at least two articulation points to add flexibility to the top and bottom portions of the outlet tube 1542. The curve of the patient's forehead is an important aspect as it determines the angle at which the patient interface will sit on the patient's face. The articulation system provided by the outlet tube assembly provides a range of positions to accommodate different forehead shapes, sizes, heights and/or angles of different patients. Patient's foreheads may vary in shape and height, such as high, low, or sloping, as well as in length such as between 65 mm and 125 mm, e.g., 75-100 mm, 70-120 mm, 80-110 mm, 90-100 mm, etc.

Top Articulated Connector

The top articulated connector 1544 provides a flexible interface between the outlet 1521 of the flow generator 1520 and the top portion 1543 of the relatively rigid outlet tube 1542. The top articulated connector 1544 provides one or more of the following functions: retain and seal the relatively rigid outlet tube to the flow generator; provide fore and aft flex to accommodate a range of anthropometric variations across the patient fit range; provide lateral (side to side) stability; provide visual continuity between the form of the flow generator and the relatively rigid outlet tube; and/or provide structure adapted to accommodate smaller head sizes and allow the outlet tube to wrap over the forehead to the flow generator positioned on the head.

Figure 83:
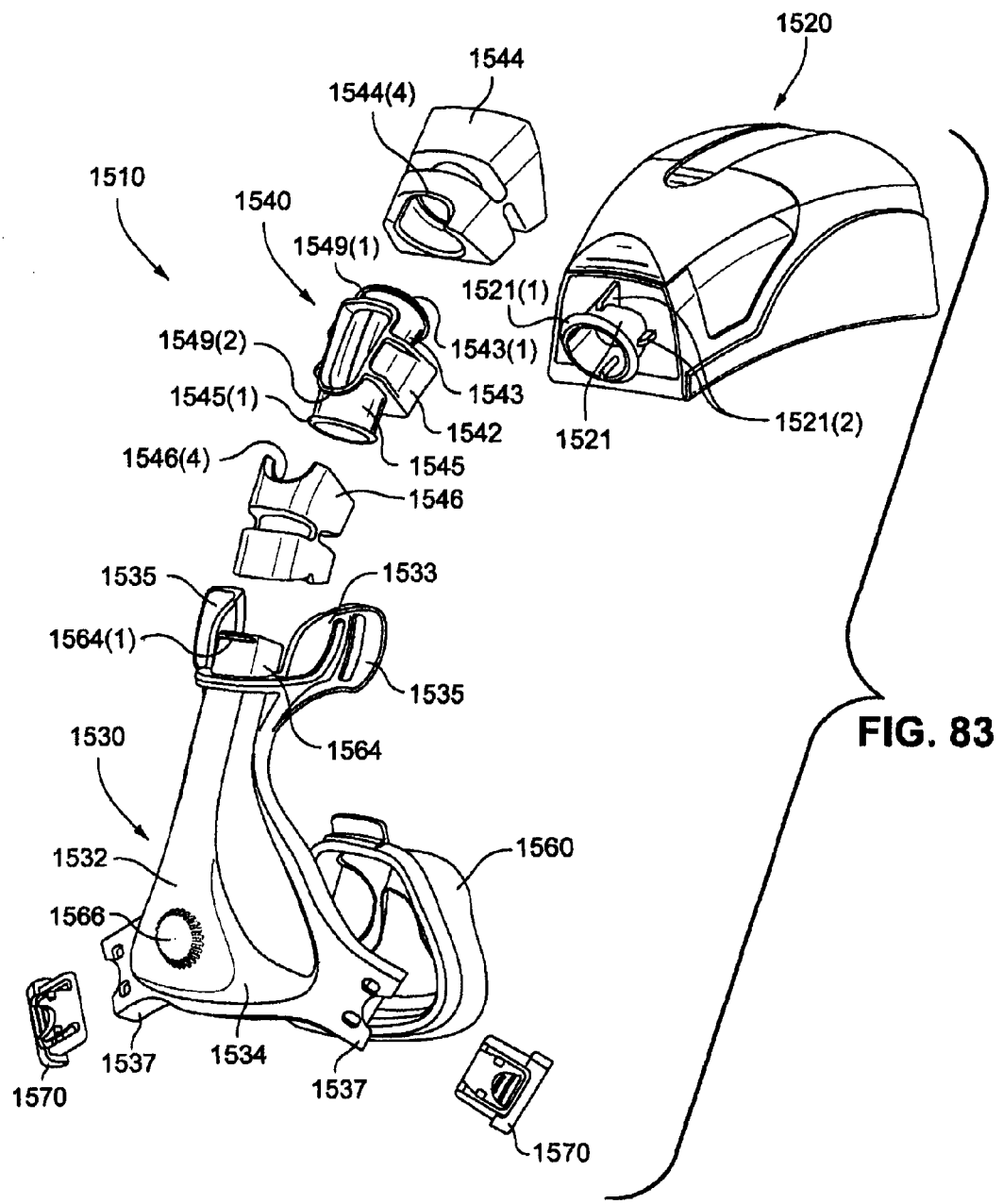
FIG. 83 is an exploded view of the headworn PAP system of FIG. 80.
Figure 84:
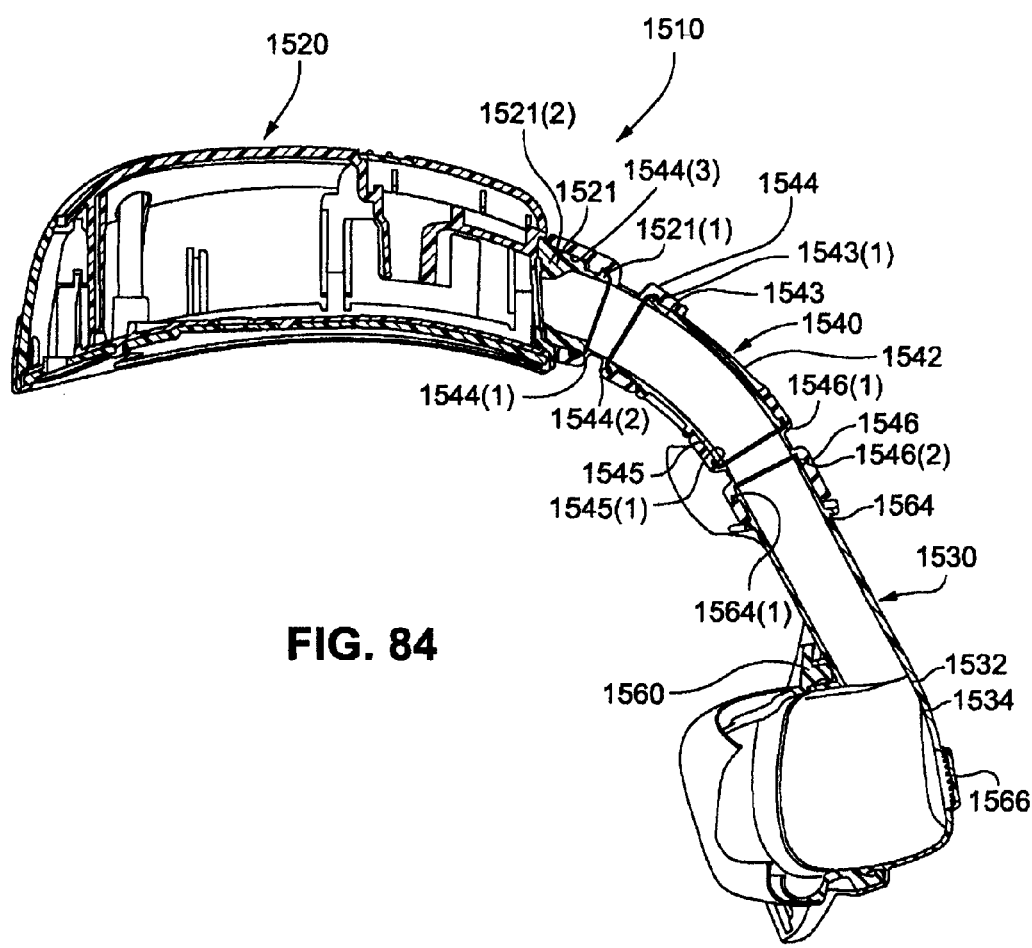
FIG. 84 is a cross-sectional view of the headworn PAP system of FIG. 80.
Figure 85:
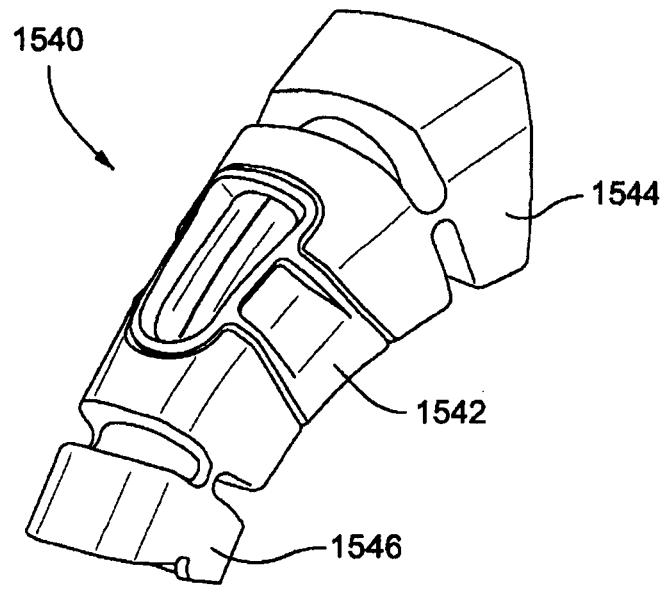
FIG. 85 is a perspective view of an outlet tube assembly according to an example of the present technology.
Figure 86:
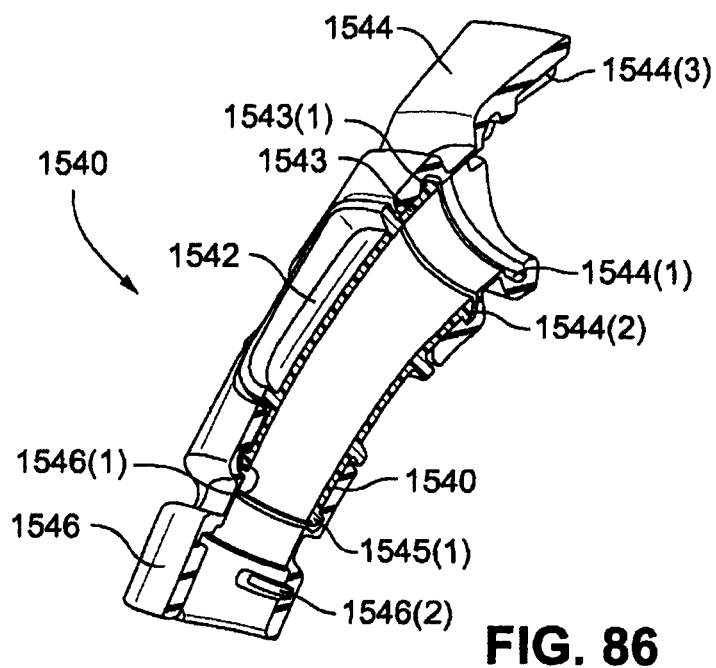
FIG. 86 is a cross-sectional view of the outlet tube assembly of FIG. 85.
Figure 87:
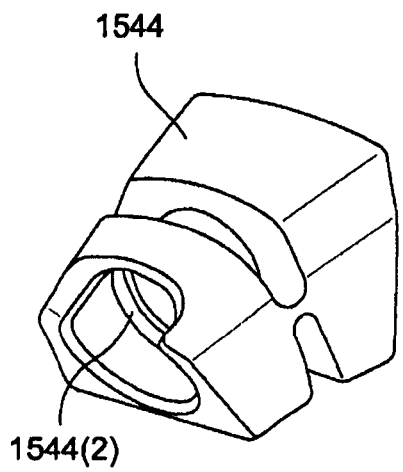
FIGS. 87 and 88 are perspective views of a top articulated connector of the outlet tube assembly of FIG. 85.

As best shown in FIGS. 83, 84 and 86, the top articulated connector 1544 includes a first annular recess 1544(1) along an interior surface thereof adapted to engage an annular barb or flange 1521(1) (e.g., oval shaped, circular shaped) provided to the end of the outlet 1521, i.e., connector pushed over outlet. The top articulated connector 1544 also includes a second annular recess 1544(2) (e.g., see FIGS. 84, 86, and 87) along an interior surface thereof adapted to engage an annular barb or flange 1543(1) provided to the top portion 1543 of the outlet tube 1542, i.e., connector pushed over outlet tube. The connection between the relatively rigid outlet 1521 and relatively rigid outlet tube 1542 with the relatively flexible connector 1544 provides sufficient retention and seal between these components.

In the illustrated example, the barbs include a generally rounded shape such as circular, oval, or ellipse shape. However, other barb shapes are possible, e.g., square, rectangular, or arced shaped. Also, the connection between the top articulated connector, outlet, and outlet tube may include the opposite arrangement, e.g., barb may be located on the top articulated connector and the flow generator may include an outlet made of a softer material to allow it to be pushed over the barb on the connector.

As best shown in FIGS. 83, 84, and 86, the connection between the top articulated connector 1544 and the flow generator outlet 1521 includes one or more recesses (cutouts) and corresponding ribs to provide a poke-yoke or mistake-free connection. In the illustrated example, the flow generator outlet includes one or more ribs 1521(2) (e.g., 2, 3, 4, or more ribs) adapted to engage corresponding recesses 1544(3) along an interior surface of the top articulated connector 1544. However, the opposite arrangement may also be used, i.e., ribs on connector and recesses on outlet.

Such rib/recess arrangement prevents a standard circular air delivery tube from being attached to the flow generator outlet as a retained and sealed connection will not be formed. For example, the ribs 1521(2) on the flow generator outlet 1521 will prevent a standard tube from pushing too far onto the flow generator outlet thus resulting in an unstable connection. Furthermore, if a standard tube is pushed over the ribs of the flow generator outlet, this will result in leaks around the ribs in use. However, a standard connection without ribs may be utilized but this would allow any standard tube to be connected to the flow generator. Such an arrangement may result in ineffective therapy being provided, unless the flow generator is able to compensate for the different tube impedances.

The top articulated connector may also have a thickness adapted to provide a higher retention force with the flow generator outlet. A thicker top articulated connector may have a higher hoop stress at the connection between the flow generator outlet and the top articulated connector, thereby increasing the retention force. This higher retention force may also better stabilize the position of the mask with respect to the flow generator. The top articulated connector may have a thickness of, for example, about 2-10 mm, about 4-6 mm, about 4 mm.

Figure 88:
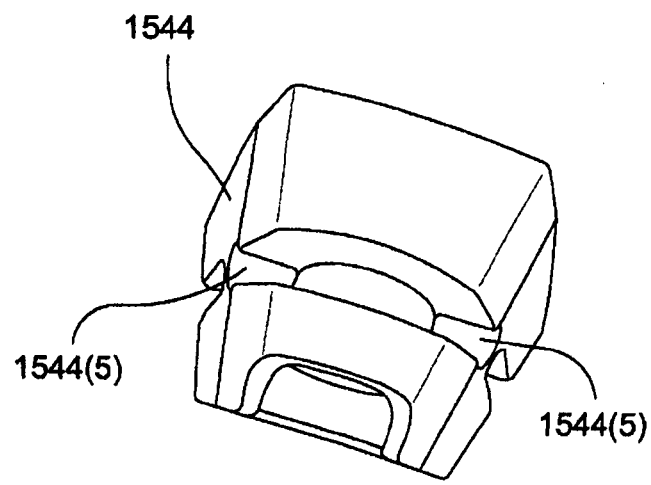
Figure 89:
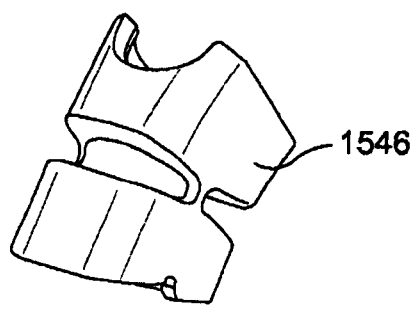
FIGS. 89 and 90 are perspective views of a bottom articulated connector of the outlet tube assembly of FIG. 85.

As best shown in FIG. 88, the top articulated connector 1544 includes a set of side ribs 1544(5) (e.g., radius of curvature of about 5-10 mm, e.g., 7 mm) that provide side to side stability but allow backward and forward movement. The side ribs 1544(5) are formed by having a thinned wall section in the top articulated connector 1544. The thin walled section allows the top articulated connector to flex or articulate in a backward and forward direction to accommodate a range of anthropometric variations between patients, i.e., different forehead heights and angles between different patients. The thin wall section may have a thickness of about 0.1 to 1 mm, for example about 0.2 mm to 0.6 mm, for example about 0.5 mm. In an alternative example, not shown, the articulation may be achieved by using a combination of materials that allow more flexibility to a certain region of the top articulated connector 1544. For example, co-molding a more flexible material in the region 1544(5) instead of side ribs to allow flexibility in movement of the connector. The top articulated connector 1544 may provide an articulation or flexing range of about 0-90° in each of the forward and backwards directions, preferably about 0-60°, or about 0-50°, or about 0-45°, such as 0-30°, 0-25°, 0-20°, 0-15°. It is to be understood that other flexing angles may be utilized. In some examples, the top articulated connector 1544 may be designed to flex less in the backward direction towards the patients' forehead as opposed to forward away from the patient's forehead or vice versa.

The top articulated connector may have a varying external surface finish. For example, the top articulated connector may have a polished top surface and other surfaces frosted. This may enhance the visual appeal of the component and may aid usability, i.e., make the sides of the top articulated connector easier to grip. It may also indicate alignment.

Bottom Articulated Connector

The bottom articulated connector 1546 provides a flexible interface between the bottom portion 1545 of the relatively rigid outlet tube 1542 and the inlet tube 1564 of the frame 1532. The bottom articulated connector 1546 provides one or more of the following functions: provide a sealed airpath between the relatively rigid outlet tube and the frame; retain the relatively rigid outlet tube to the frame; provide forward and backward movement with respect to the face; allow different angles as defined by the shape of the user's head; provide visual continuity between the form of the relatively rigid outlet tube and the frame; allow easy removal and assembly including orientation; provide a very flexible joint where the level of flexibility is not dictated but is passively determined by the specific shape of the user's head; and/or provide side to side stability (e.g., connector may include a set of side ribs that provide the side to side stability but do not prevent backward and forward movement).

As best shown in FIGS. 83, 84, and 86, the bottom articulated connector 1546 includes a first annular recess 1546(1) along an interior surface thereof adapted to engage an annular barb or flange 1545(1) (e.g., oval shaped, circular shaped) provided to the bottom portion 1545 of the outlet tube 1542, i.e., connector pushed over outlet tube. The bottom articulated connector 1546 also includes one or more spaced apart second recesses 1546(2) along an interior surface thereof adapted to engage respective barbs or flanges 1564(1) provided to the end of the inlet tube 1564, i.e., connector pushed over inlet tube. The connection between the relatively rigid outlet tube 1542 and relatively rigid inlet tube 1564 with the relatively flexible connector 1546 provides sufficient retention and seal between these components. It should be appreciated that the barbs may have other suitable shapes (e.g., square, rectangular, or arced shaped), and the connection between the bottom articulated connector, outlet tube, and inlet tube may include the opposite arrangement, e.g., barbs may be located on the bottom articulated connector and the outlet tube and inlet tube may be made of a softer material to allow it to be pushed over the barbs on the connector.

Figure 90:
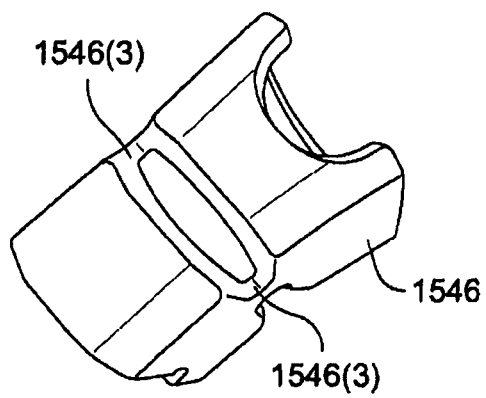
Figure 91:
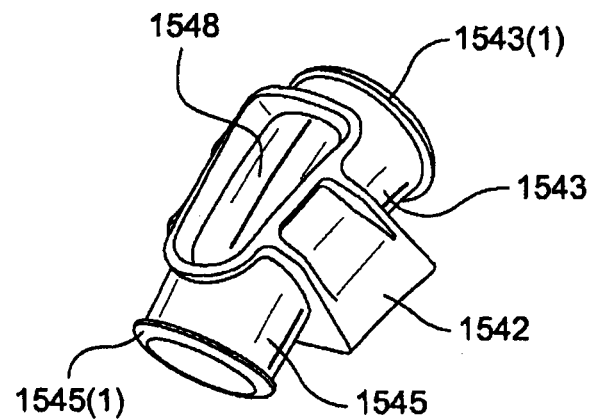
FIG. 91 is a perspective view of an outlet tube of the outlet tube assembly of FIG. 85.

As best shown in FIG. 90, the bottom articulated connector 1546 includes a set of side ribs 1546(3) (e.g., radius of curvature of about 1-6 mm, e.g., 2.7 mm) that provide side to side stability but allow backward and forward movement. The side ribs 1546(3) are formed by having a thinned wall section in the bottom articulated connector 1546. The thin walled section allows the bottom articulated connector to flex or articulate in a backward and forward direction to accommodate a range of anthropometric variations between patients, i.e., different forehead heights and angles between different patients. The thin wall section may have a thickness of about 0.1 to 1 mm, for example about 0.2 mm to 0.6 mm, for example about 0.5 mm. In an alternative example, not shown, the articulation may be achieved by using a combination of materials that allow more flexibility to a certain region of the bottom articulated connector 1546. For example, co-molding a more flexible material in the region 1546(3) instead of side ribs to allow flexibility in movement of the connector. A lower shore hardness material may be used at the articulation region. The bottom articulation connector 1546 may provide an articulation or flexing range of about 0-90° in each of the forward and backwards directions, preferably about 0-60° or about 0-50°, or about 0-45°, such as 0-30°, 0-25°, 0-20°, 0-15°. It is to be understood that other flexing angles may be utilized. In some examples, the bottom articulation connector 1546 may be designed to flex less in the backward direction towards the patients' forehead as opposed to forward away from the patient's forehead or vice versa.

The bottom articulated connector may have a varying external surface finish. For example, the bottom articulated connector may have a polished top surface and other surfaces frosted. This may enhance the visual appeal of the component and may aid usability, i.e., make the sides of the bottom articulated connector easier to grip. It may also indicate alignment.

Outlet Tube

The relatively rigid outlet tube 1542 provides a conduit path between the top articulated connector 1544 and the bottom articulated connector 1546. The relatively rigid outlet tube 1542 provides one or more of the following functions: provide airflow between the top articulated connector and the bottom articulated connector; retain and seal to the top articulated connector and the bottom articulated connector; provide visual continuity between the top articulated connector and the bottom articulated connector; and/or allow easy removal and assembly including orientation.

Preferably, the top articulated connected and the bottom articulated connector may be connected to the relatively rigid outlet tube in such a way that the relatively rigid outlet tube forms the majority or large portion of the inner surface or air path. For example, the top articulated connected and the bottom articulated connector may wrap or slide over an outer surface of the relatively rigid outlet tube. Such an arrangement may reduce noise, as the relatively rigid outlet tube may be constructed of a material that is sound dampening, insulating or prevents transmission of noise. This may be due to the material's properties or the manner in which the material is treated or formed. For example, the relatively rigid outlet tube may be formed of a relatively stiff or rigid material, for example a material that is able to support its own weight. The relatively stiff or rigid material has a Young's modulus measure of at least 1 gigapascal (GPa), such greater than 1.5 GPa, or greater than 2 GPa. Such a material may be inherently noise dampening due to the molecular structure of the material. Preferably, the outlet tube may also be relatively thin so as to reduce the weight and visual bulk of the mask.

Preferably, the outlet tube extends along a central or mid portion of the outlet tube assembly. Preferably, there are soft or relatively flexible connections between the outlet tube and the mask inlet and the flow generator outlet. Preferably, these relatively flexible connections (for example, a top articulated connector and a bottom articulated connector) are of sufficient height to prevent the outlet tube from hitting or contacting the mask inlet and the flow generator outlet. This is to avoid wear of the outlet tube, mask inlet and flow generator outlet. Furthermore, since these components (outlet tube, mask inlet and flow generator outlet) may be relatively rigid, contact of these components may result in noise.

In an example, the outlet tube includes a fixed length of about 30-70 mm, e.g., about 60 mm, about 45 mm, about 50 mm, about 47 mm, which is not adjustable. In an alternative example, the outlet tube may include a bellows section that provides auto-adjustment of the length of the outlet tube to fit the user's face. In a further alternative example, a sliding adjustment may be provided to adjust the position of the flow generator on the user's head. The sliding adjustment may be included in the headgear cradle that supports the flow generator to allow adjustment to fit different size heads.

As best shown in FIG. 86, the diameter of the outlet tube 1542 tapers from its top portion near the outlet of the flow generator to its bottom portion near the inlet tube of the frame, i.e., larger diameter at the top portion to smaller diameter at the bottom portion. Exemplary diameters are: about 20 mm at the top portion to about 15 mm at the bottom portion; about 18 mm at the top portion to about 16 mm at the bottom portion. However, a taper in the opposite direction may also be utilized. This arrangement provides one or more of the following benefits: benefits for tooling to allow the outlet tube to be molded; and/or benefits with respect to noise.

Preferably, the internal surface is smooth, i.e., does not contain any steps, grooves, corrugations etc., to reduce the noise created in the outlet tube. That is, the outlet tube may have a smooth or continuous bore. Any transitions in the diameter of the bore may preferably be smooth transitions, e.g., a gradient.

In an alternative example (not shown), the top articulated connector 1544, the bottom articulated connector 1546, and the outlet tube 1542 may be formed in a single inlet tube component with one or more, and preferably two or more, articulation regions incorporated within the inlet tube component. As noted above, the articulation regions may be provided by thin walled sections of the inlet tube component and/or the use of different materials having different levels of flexibility and/or rigidity, for example, the top and bottom portions may be manufactured from relatively flexible material to allow the flexing or articulation and the central portion may be formed of a more rigid material.

Outlet tube may also have a cut out or thumb grip 1548 (see FIG. 91) on its upper surface. The cut out may provide a gripping portion and may also provide a surface for the top and bottom articulated connectors 1644, 1646 to abut when connected to outlet tube 1642.

Mistake Free Connection

In an example, the outlet tube assembly 1540 is structured to ensure the components are connected in the correct orientation, e.g., poke-yoke or mistake-free connection. For example, as shown in FIG. 83, the outlet tube 1542 includes upper and lower generally U-shaped protrusions or fingers 1549(1), 1549(2) adapted to be received in corresponding recesses 1544(4), 1546(4) provided to the top and bottom articulated connectors 1544, 1546.

Figure 92:
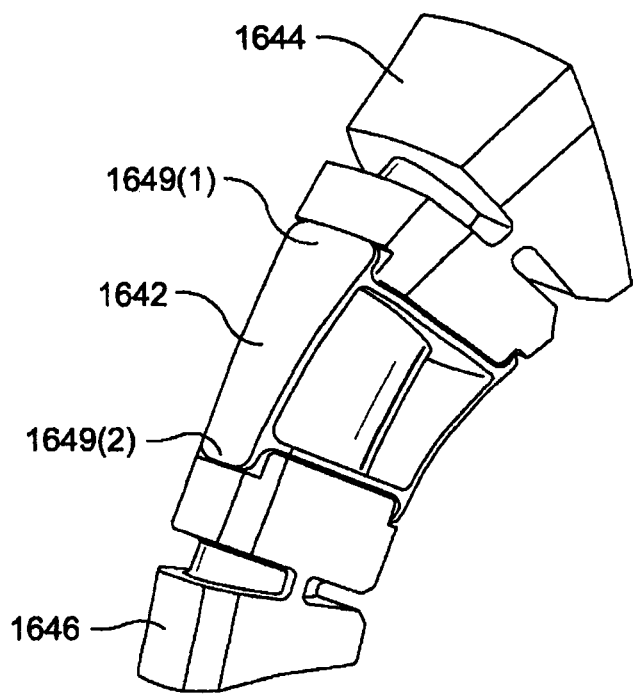
FIG. 92 is a perspective view of an outlet tube assembly according to another example of the present technology.
Figure 93:
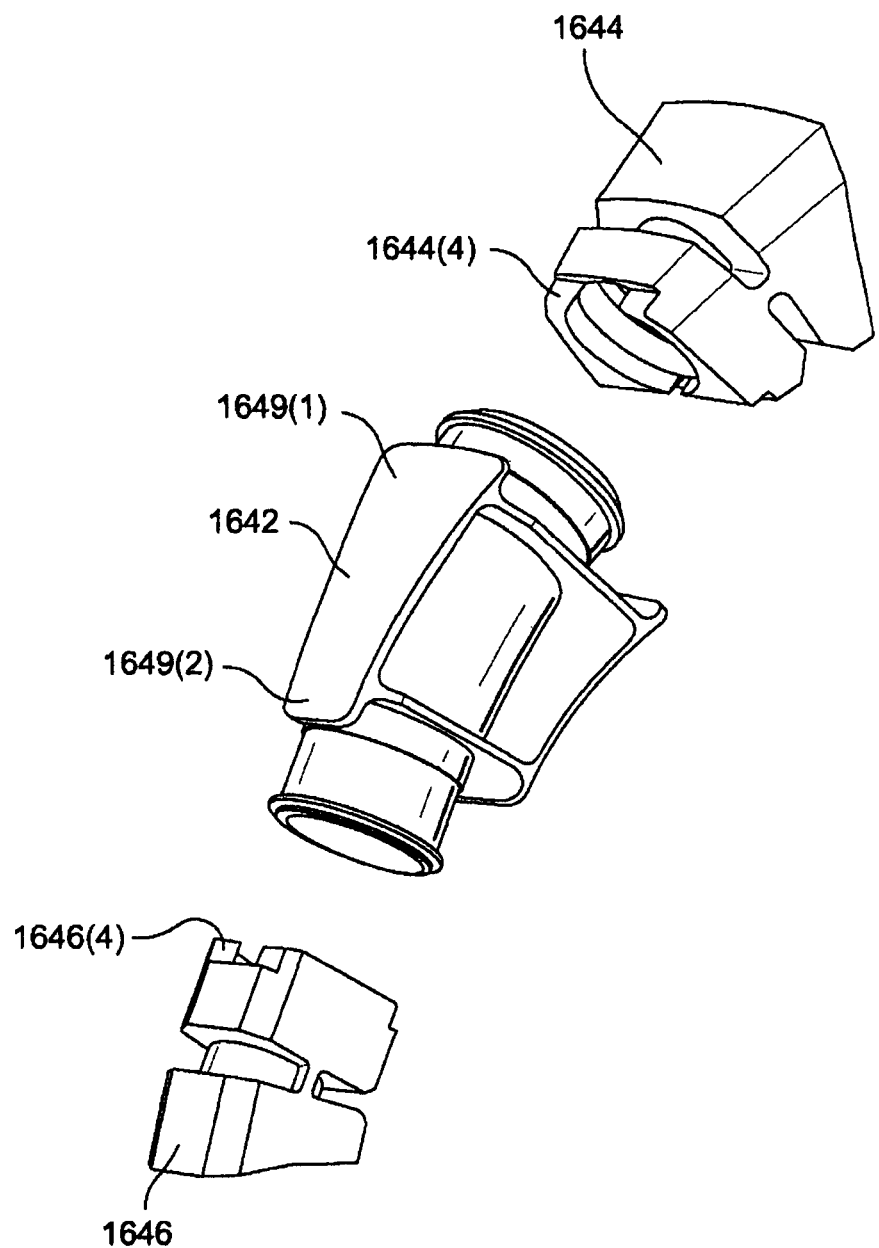
FIG. 93 is a cross-sectional view of the outlet tube assembly of FIG. 92.

In another example, as shown in FIGS. 92 and 93, outlet tube 1642 may include upper and lower generally square-shaped protrusions or fingers 1649(1), 1649(2) adapted to be received in corresponding recesses 1644(4), 1646(4) provided to top and bottom articulated connectors 1644, 1646. Upper and lower generally square-shaped protrusions or fingers 1649(1), 1649(2) may also prevent top and bottom articulated connectors 1644, 1646 from rotating about outlet tube 1642.

Frame

In an example, the frame 1532 is a relatively rigid, transparent shell (e.g., constructed of polycarbonate) which provides one or more of the following functions: retains the cushion; provides airpath between the bottom articulated connector and the cushion; provides connection for the upper and lower side straps of the headgear; retains and seals with the bottom articulated connector; contains the forehead support to locate the patient interface against the forehead; and/or contains the vent.

In an example, the frame 1532 may be structured to accommodate a desired depth of the membrane 1562 at the top of the cushion (i.e., across the nasal bridge). At this point, provision may also be made for a cushion bead depth and then the diameter of the vertical inlet tube 1564. The sum of these distances creates a minimum horizontal distance from the face which is approximately the furthermost protrusion of the frame.

In an example, the frame is structured such that the vent 1566 is generally perpendicular to a line of draw to facilitate molding. The area surrounding the vent may also be substantially flat and perpendicular to provide a relatively smooth transition from the vent to the rest of the frame. This, combined with the desired spacing in the nasal bridge region, may define the depth in the nasal bridge region of the frame.

The frame may be styled to incorporate the desired functionality into a smooth homogenous form with a minimum of abrupt changes of direction which can lead to reflections and light lines in a transparent part. Also, the frame is structured to minimize obtrusiveness.

The lower headgear connectors 1537 (i.e., clip receptacles for engaging headgear clips) as best shown in FIGS. 80 to 83 provide visual weight to the bottom of the frame, while the nose area tapers upwards and transitions into the inlet tube 1564. The upper headgear connectors 1535 and forehead support 1533 provide visual balance to the clip receptacles, defining a shape that suggests a slim hourglass form when viewed from the front.

The frame geometry may also be defined to some degree by the angle and location of the inlet tube 1564 to ensure the mask fits correctly on the patient's face.

Forehead Support

The forehead support 1533 provides one or more of the following functions: provide comfortable location of the patient interface against a range of forehead shapes and angles without adjustability; allow freedom of movement for the relatively rigid outlet tube and bottom articulated connector to accommodate a range of forehead shapes and angles; resist anticipated reasonable abuse load scenarios without breaking; accommodate straps (e.g., strap connection); and/or accommodate the bottom articulated connector sealing and retention interface.

In the illustrated example, the forehead support 1533 is a fixed forehead support, i.e., non-adjustable. In an alternative example, the forehead support may be adjustable, e.g., flexible or selectively adjustable between two or more positions.

Figure 94:
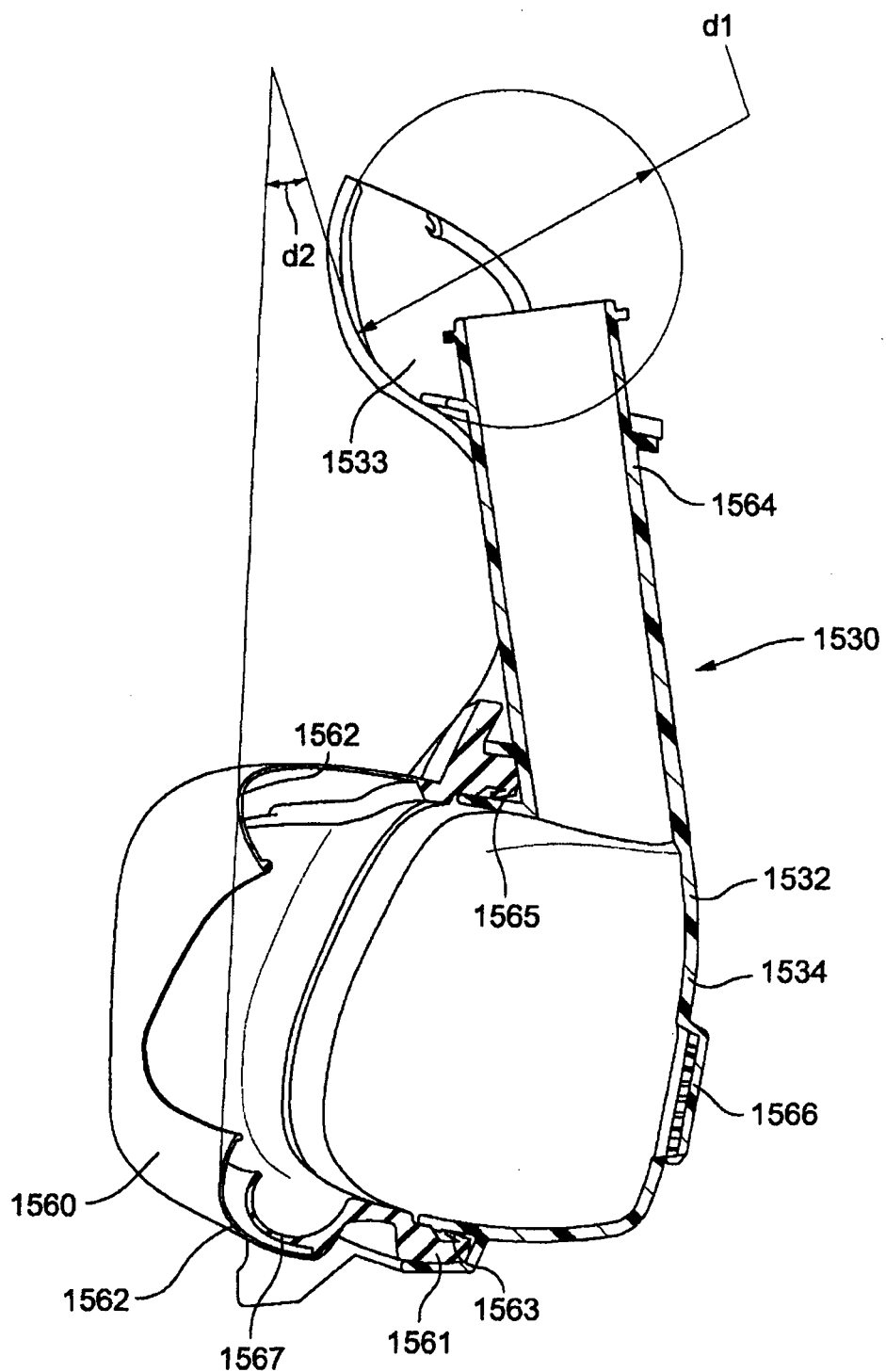
FIG. 94 is a cross-sectional view of a patient interface according to an example of the present technology.

FIG. 94 shows exemplary angle and position of the forehead support 1533 relative to the cushion 1560, e.g., d1 about 40-60 mm (e.g., about 50 mm) and d2 about 5-15° (e.g., 9.3°).

In an example, one or more forehead pads (e.g., constructed of silicone, foam, etc.) may be provided to the forehead support to improve frictional resistance between the patient interface and the patient's forehead, e.g., to prevent the flow generator mass moving the patient interface up when the patient's head is tilted back.

Chin Strap

In an alternative example, a chin strap may be used to assist in retaining the patient interface in position and preventing the flow generator from moving the patient interface upwards in use. The chin strap may be provided as an integral component with the PAP system or may be provided as an accessory or retro-fit.

Figure 95:
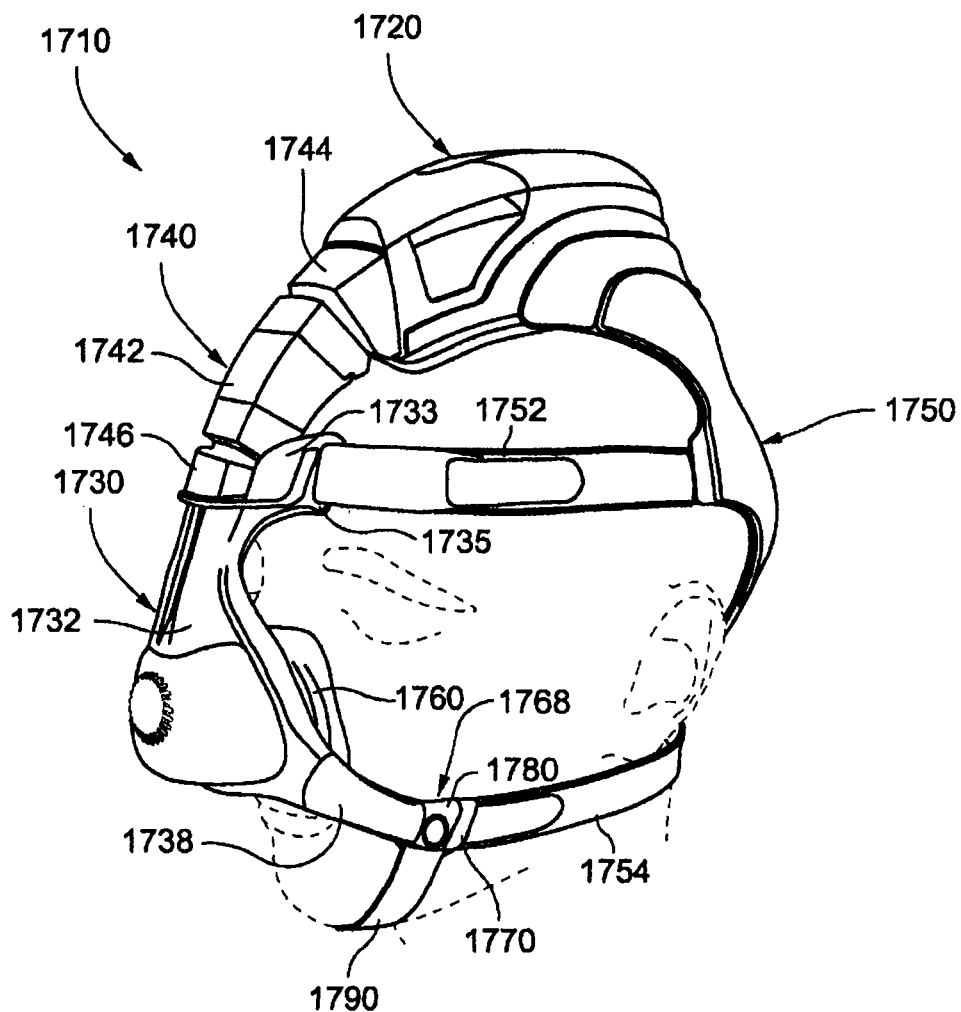
FIG. 95 is a perspective view of a headworn PAP system including a chin strap according to an example of the present technology.
Figure 96:
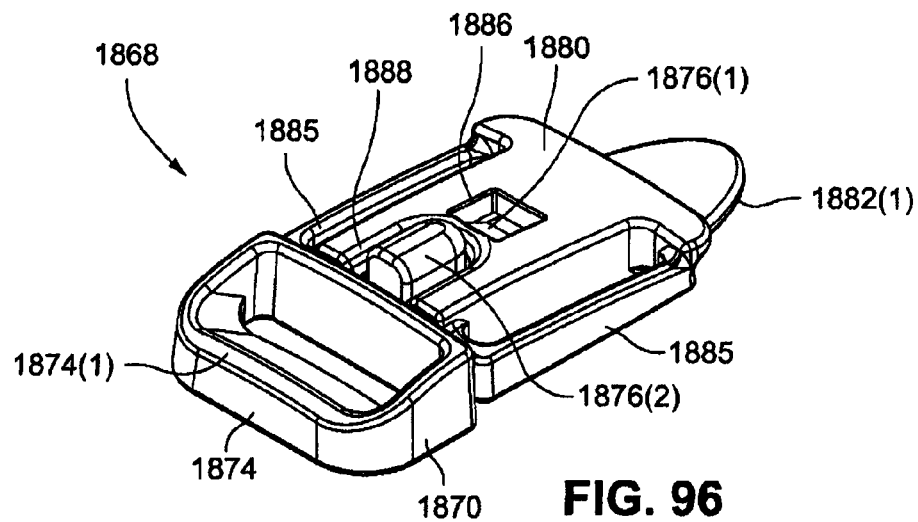
FIG. 96 is a perspective view of a clip arrangement according to an example of the present technology.
Figure 97:
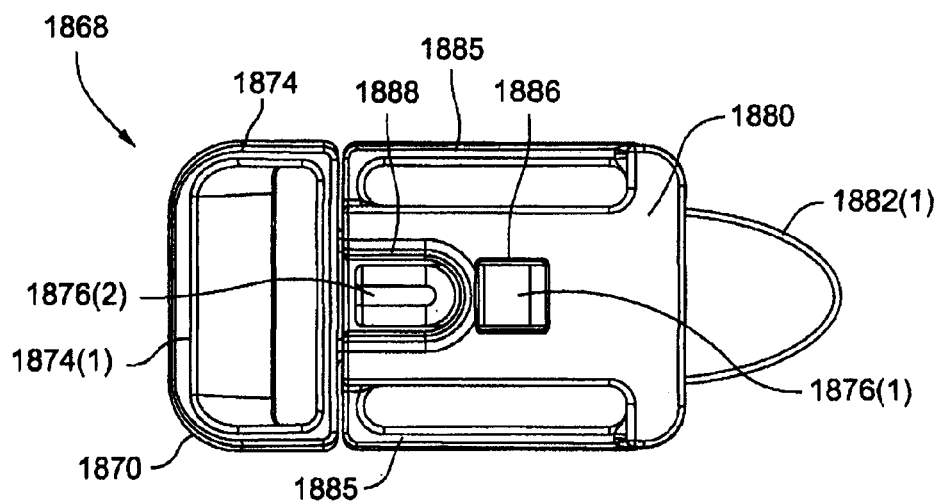
FIG. 97 is a top view of the clip arrangement of FIG. 96.
Figure 98:
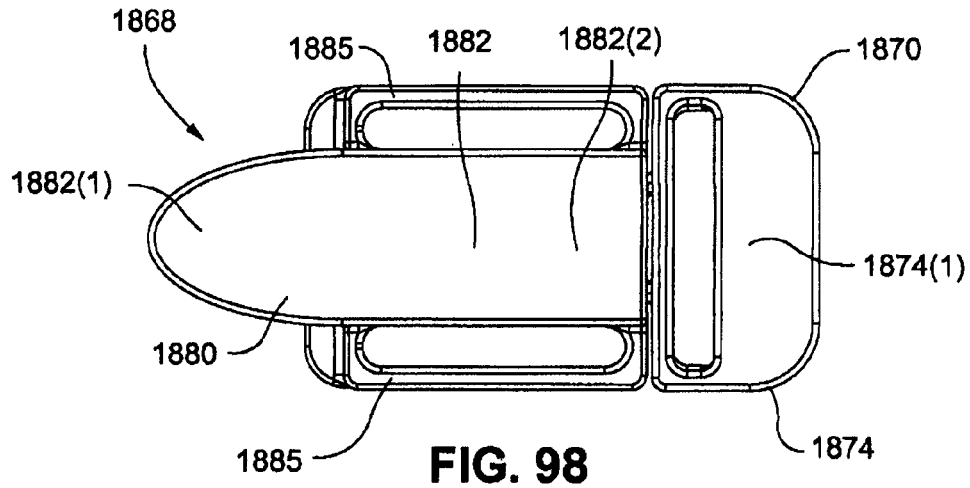
FIG. 98 is a bottom view of the clip arrangement of FIG. 96.
Figure 99:
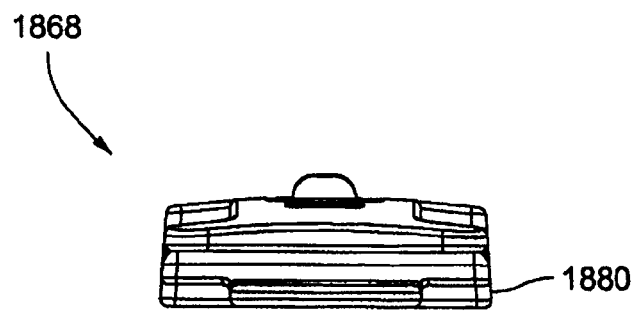
FIG. 99 is a rear view of the clip arrangement of FIG. 96.
Figure 100:
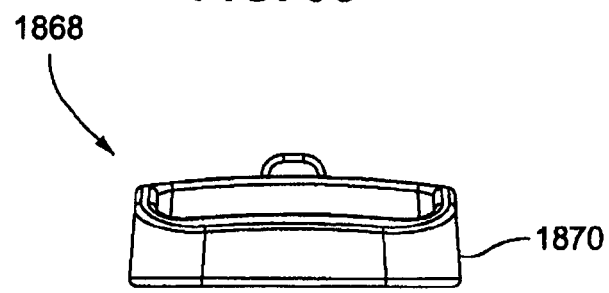
FIG. 100 is a front view of the clip arrangement of FIG. 96.
Figure 101:
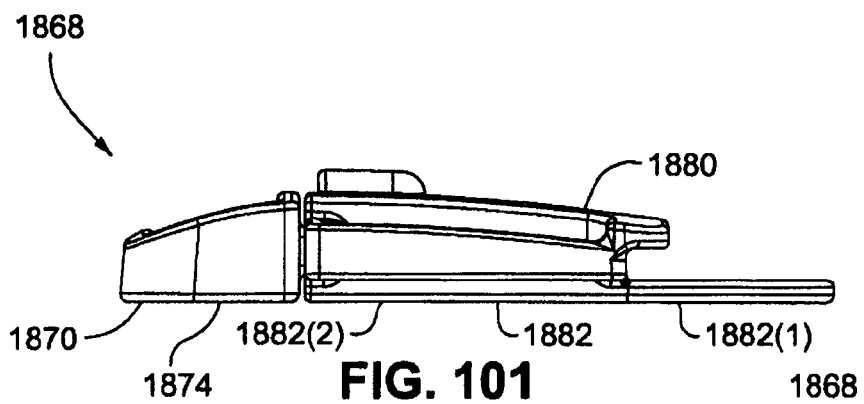
FIG. 101 is a side view of the clip arrangement of FIG. 96.

For example, FIG. 95 shows a headworn PAP system 1710 including a chin strap 1790 according to an example of the present technology. As illustrated, the headworn PAP system 1710 includes a patient interface 1730 (including frame 1732 and cushion 1760) adapted to be secured to and sealed against a portion of the patient's face, in use, by headgear 1750, a flow generator 1720 adapted to be connected to the patient interface and secured by a portion of the headgear 1750 to the patient's head, and an outlet tube assembly 1740 (including outlet tube 1742 and upper and lower articulated connectors 1744, 1746) that interconnects the patient interface and the flow generator.

An upper portion of the frame 1732 provides a forehead support 1733 with upper headgear connectors 1735 (e.g., including slots) for engaging upper side straps 1752 of the headgear. A lower portion of the frame provides a clip arrangement 1768 (e.g., including a clip receptacle 1780 for engaging a headgear clip 1770) on each side thereof for engaging both the lower side straps 1754 of the headgear and the chin strap 1790.

As illustrated, the clip arrangement 1768 is provided to an elongated arm or strap 1738 (e.g., constructed of silicone) extending from the frame 1732, which helps to support and position the clip arrangement. In an example, the silicone strap 1738 may be coupled to the frame 1732 by one or more lugs structured to interlock or otherwise engage the frame. The clip arrangement 1768 is provided to the opposite end of the silicone strap 1738 and includes structure to attach to both a lower side strap 1754 and the chin strap 1790. In an alternative example, the strap 1738 may be a piece of headgear material adapted to connect to the clip receptacle and loop through a slot provided to the frame (e.g., exemplary embodiment of such arrangement described below).

FIGS. 96-117 illustrate a clip arrangement 1868 according to another example of the present technology. As illustrated, the clip arrangement 1868 includes a clip receptacle 1880 (shown isolated in FIGS. 104-110) adapted to be secured or otherwise provided to the frame and a headgear clip 1870 (shown isolated in FIGS. 111-117) adapted to be releasably or removably connected to the clip receptacle.

Figure 102:
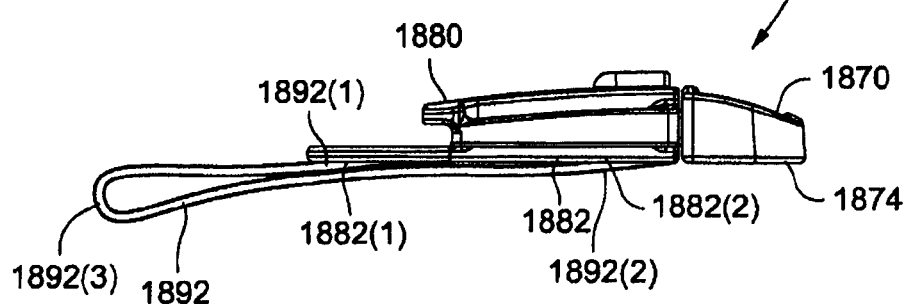
FIG. 102 shows the clip arrangement of FIG. 96 attached to a strap.
Figure 103:
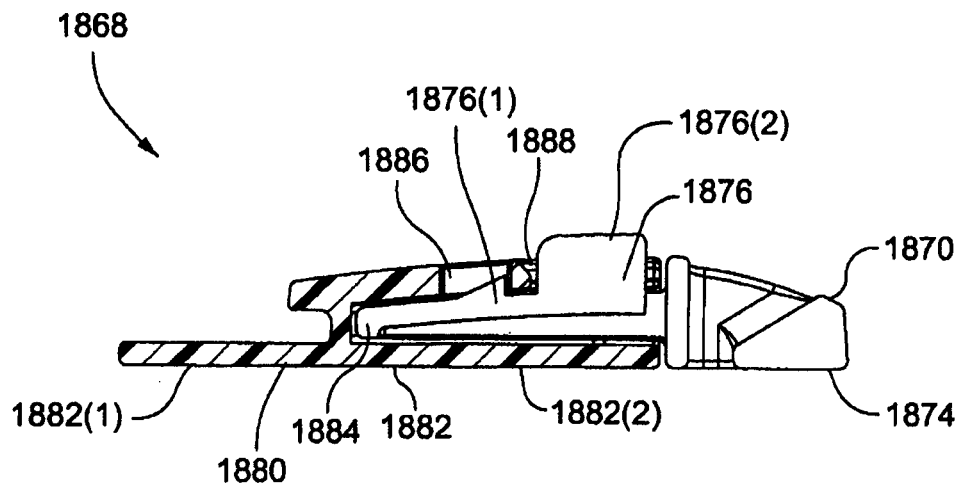
FIG. 103 is a cross-sectional view of the clip arrangement of FIG. 96.

As best shown in FIGS. 104-110, the clip receptacle 1880 includes a patient contacting side (or side closest to the patient's skin in use) having an elongated bottom wall 1882 adapted to attach to a strap 1892 (e.g., see FIG. 102) for securing or otherwise attaching the clip receptacle to the frame. The bottom wall 1882 provides a front portion or tongue 1882(1) structured to be inserted or otherwise attached to a first end of the strap. For example, the strap may be constructed of composite material (e.g., foam and fabric layers) and the tongue may be inserted between foam and fabric layers of the strap and then glued, stitched, heat-welded, or otherwise attached within the composite material. Alternatively, the tongue 1882(1) may be attached externally to the first end 1892(1) of the strap 1892 as shown in FIG. 102. The rear portion 1882(2) of the bottom wall 1882 is structured to attach to a second end of the strap. For example, the rear portion 1882(2) may be attached externally to the second end 1892(2) of the strap 1892 as shown in FIG. 102. As illustrated, this arrangement prevents the clip receptacle from directly contacting the patient's skin in use. Also, such attachment arrangement shown in FIG. 102 (i.e., first end of strap attached to tongue and second end of strap attached to rear portion) creates a loop 1892(3) adapted to engage or otherwise attach to a slot provided on the frame in use.

The non-patient contacting side (or side that faces away from the patient's skin in use) includes a slot or aperture 1884 adapted to receive the front portion of the headgear clip in use, an opening or snap receiving portion 1886 adapted to receive or interface with a snap provided to the headgear clip in use, and a recess or button receiving portion 1888 adapted to receive or interface with a button provided to the headgear clip in use.

Also, each side of the clip receptacle includes a cross-bar or chin strap loop 1885 that forms an opening through which a chin strap may pass and be removably attached. In use, the chin strap will only attach to one side of the clip receptacle. The chin strap loop is provided on both sides of the receptacle so that a single receptacle may be manufactured which is structured for use on each of the right and left sides of mask, i.e., specific receptacle does not have to be manufactured for each side of the mask.

Figure 105:
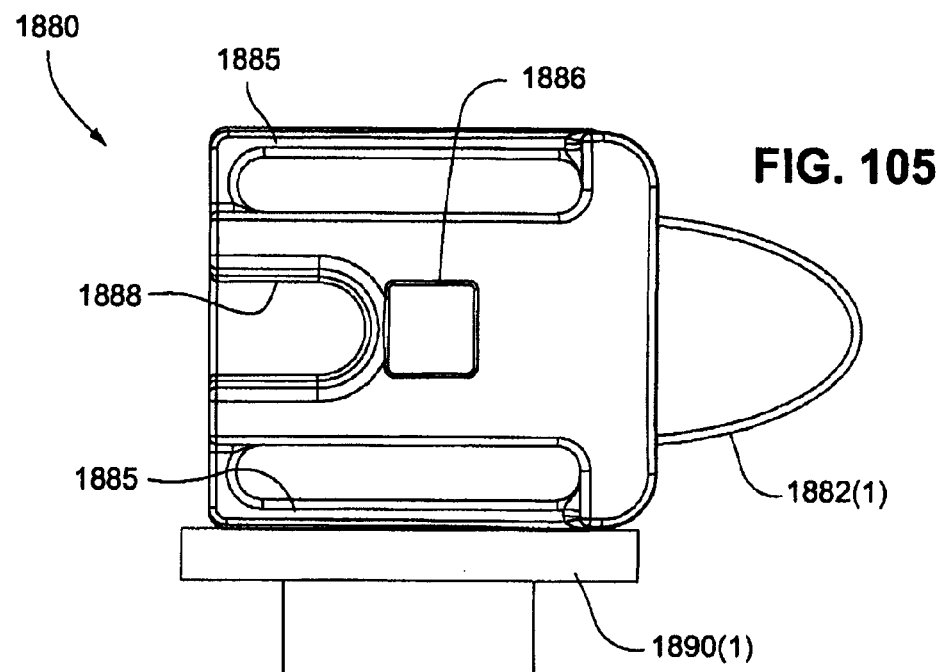
FIG. 105 is a top view of the clip receptacle of FIG. 104.
Figure 106:
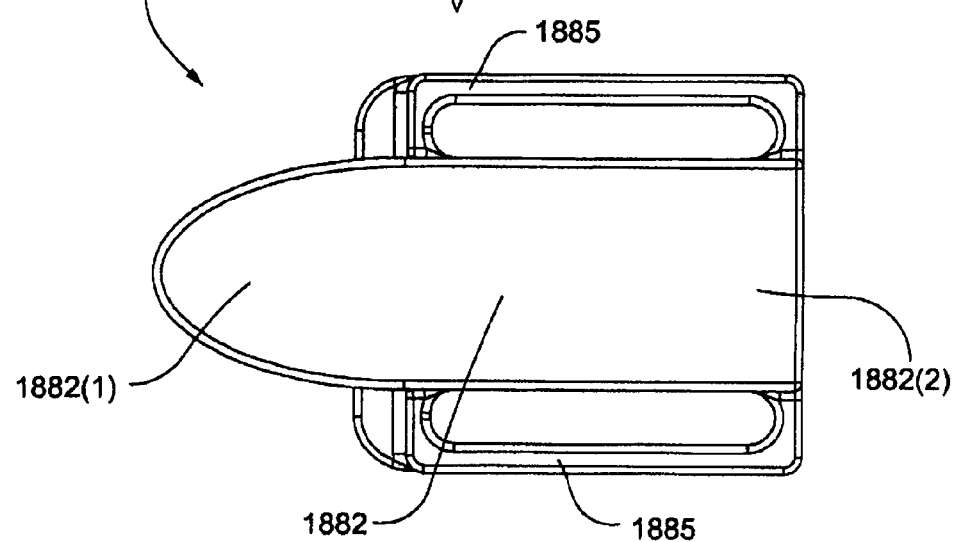
FIG. 106 is a bottom view of the clip receptacle of FIG. 104.
Figure 107:
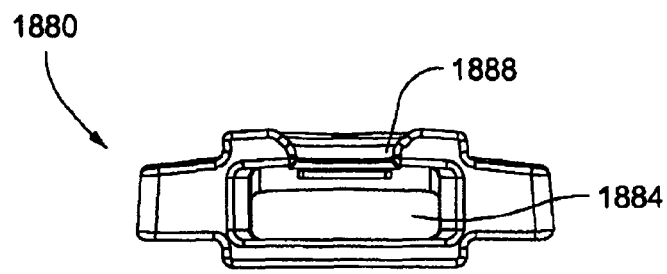
FIG. 107 is a front view of the clip receptacle of FIG. 104.
Figure 108:
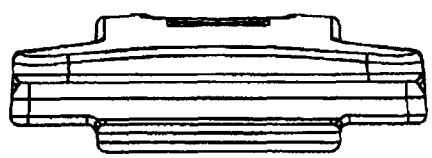
FIG. 108 is a rear view of the clip receptacle of FIG. 104.
Figure 109:
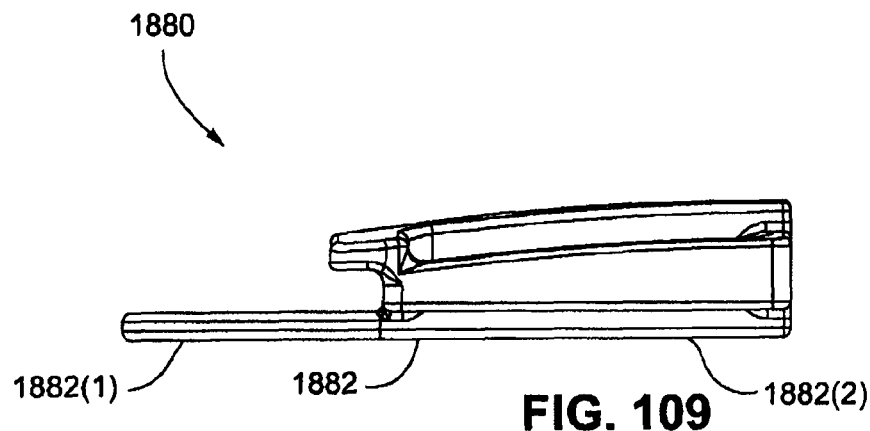
FIG. 109 is a side view of the clip receptacle of FIG. 104.
Figure 110:
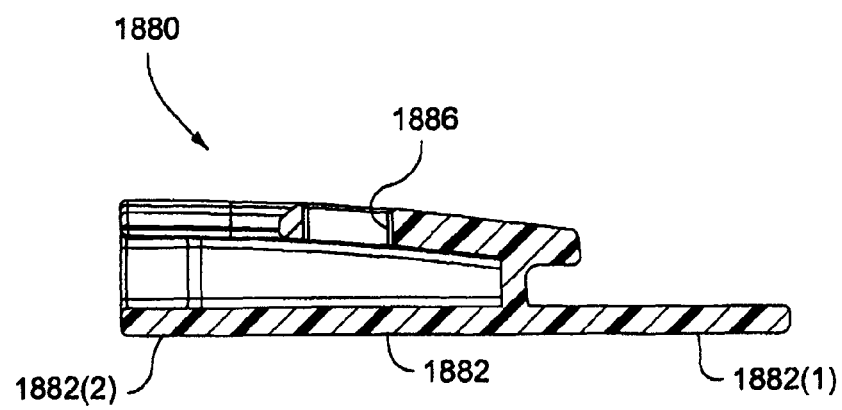
FIG. 110 is a cross-sectional view of the clip receptacle of FIG. 104.
Figure 111:
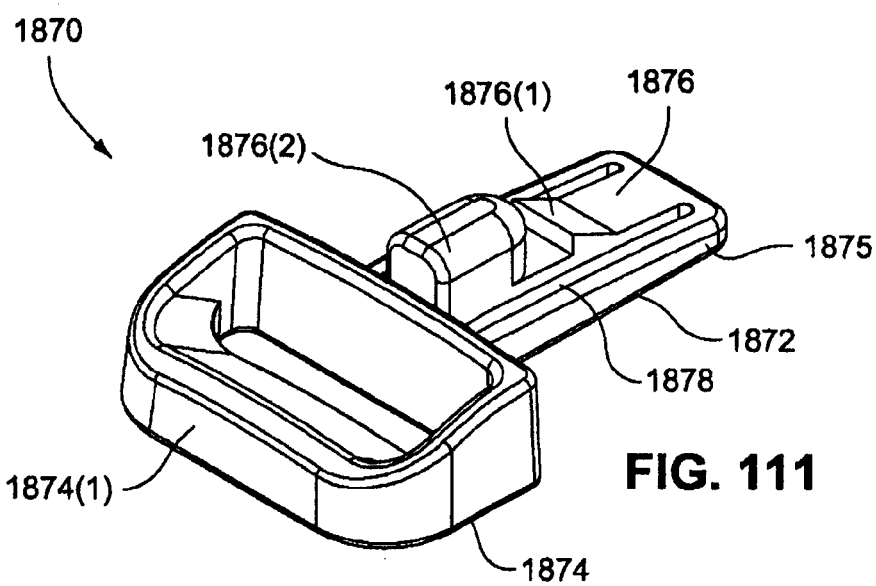
FIG. 111 is a perspective view of a headgear clip of the clip arrangement of FIG. 96.
Figure 112:
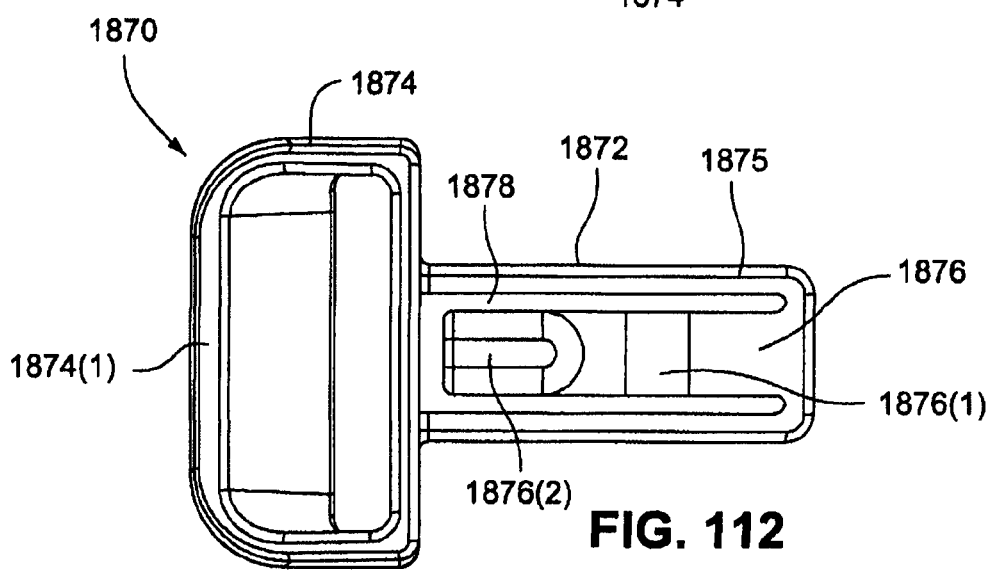
FIG. 112 is a top view of the headgear clip of FIG. 111.
Figure 113:
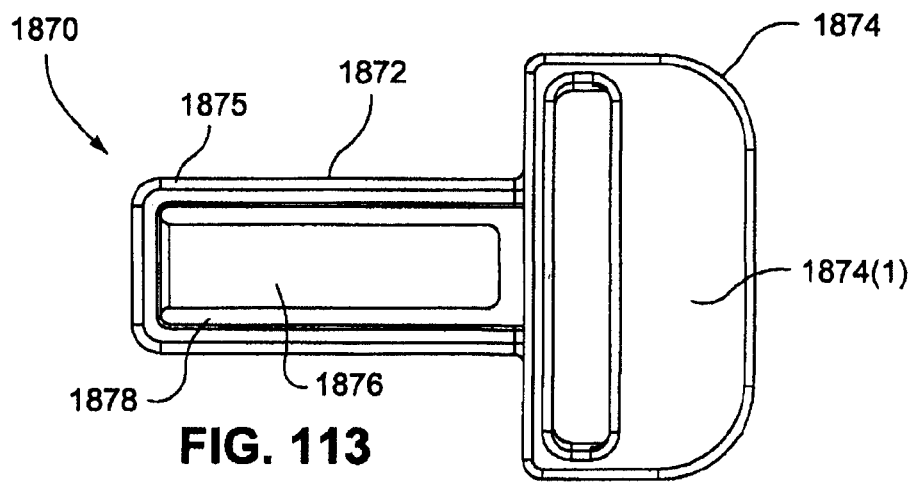
FIG. 113 is a bottom view of the headgear clip of FIG. 111.
Figure 114:
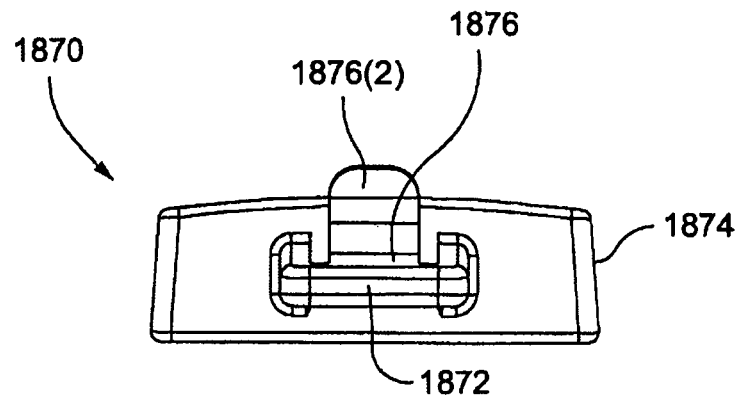
FIG. 114 is a rear view of the headgear clip of FIG. 111.
Figure 115:
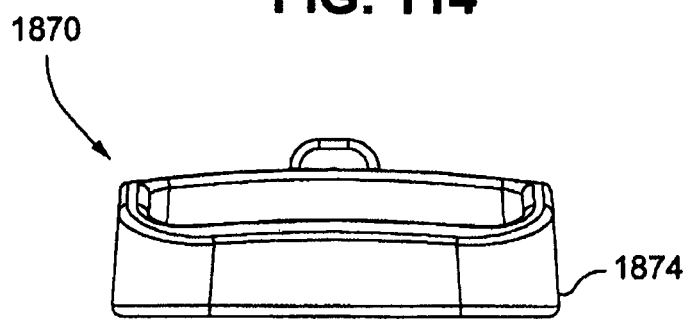
FIG. 115 is a front view of the headgear clip of FIG. 111.
Figure 116:
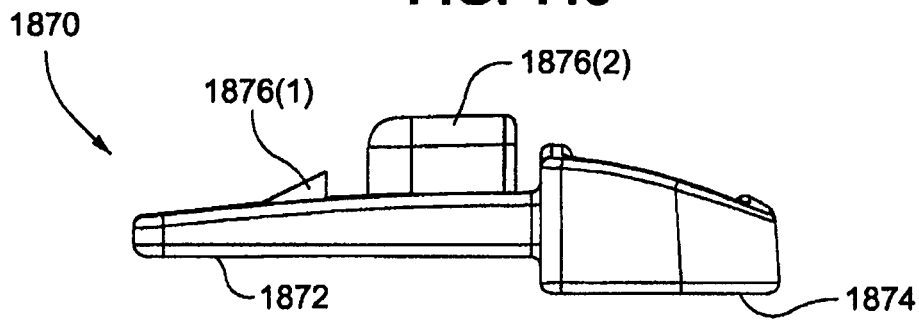
FIG. 116 is a side view of the headgear clip of FIG. 111.
Figure 117:
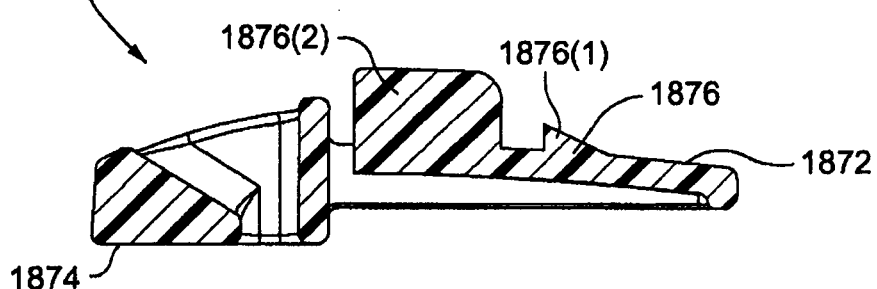
FIG. 117 is a cross-sectional view of the headgear clip of FIG. 111.

FIG. 105 shows a chin strap 1890 according to an example of the present technology. As illustrated, the chin strap may have a constant diameter except one end includes a thickened region 1890(1) that is wider than the chin strap. This arrangement allows the chin strap to loop through one chin strap loop of a clip receptacle on a first side of the mask (e.g., left side) and due to the extra width of the thickened region will remain in place by an interference fit. The opposite end of the chin strap will then loop through the other chin strap loop of a clip receptacle on a second side of the mask (e.g., right side) and secure onto itself, e.g., via a tab 1890(2) with hook material adapted to engage loop material of chin strap.

As best shown in FIGS. 111-117, the headgear clip 1870 includes a front portion 1872 adapted to interface with the clip receptacle and a rear portion 1874 adapted to interface with the lower side strap of the headgear.

As illustrated, the front portion 1872 includes a main body 1875 and a flexible spring arm 1876 provided to the main body and spaced from the main body by a groove or flexing space 1878 which allows the spring arm to flex up and down, i.e., into and out of the plane of the main body. A snap or tapered protrusion 1876(1) is provided to an intermediate portion of the spring arm and adapted to engage or interface with the opening or snap receiving portion 1886 in the receptacle in use. The free end of the spring arm includes a button 1876(2) adapted to release the snap from engagement with the snap receiving portion of the receptacle in use.

The rear portion 1874 includes a cross-bar or lower headgear strap loop 1874(1) that forms an opening through which a lower headgear strap may pass and be removably attached, e.g., an end portion of the lower strap of the headgear may be wrapped around the cross-bar.

Figure 104:
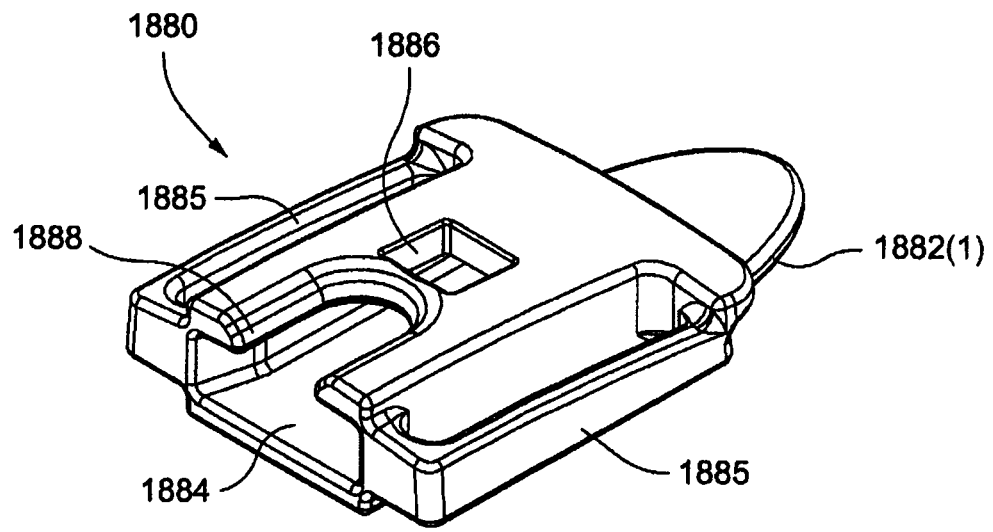
FIG. 104 is a perspective view of a clip receptacle of the clip arrangement of FIG. 96.

In use, the front portion 1872 of the headgear clip may be inserted into the slot 1884 of the clip receptacle 1880 to engage the snap 1876(1) with the snap receiving portion 1886 and secure the headgear clip 1870 to the clip receptacle 1880 (e.g., FIGS. 96-103 show the headgear clip assembled to the clip receptacle). As shown in FIG. 104, the slot 1884 may be tapered adjacent its opening to facilitate entry of the headgear clip. The button 1876(2) may be depressed to disengage the snap from the snap receiving opening and thereby allow the headgear clip to be release from the clip receptacle.

Figure 118:
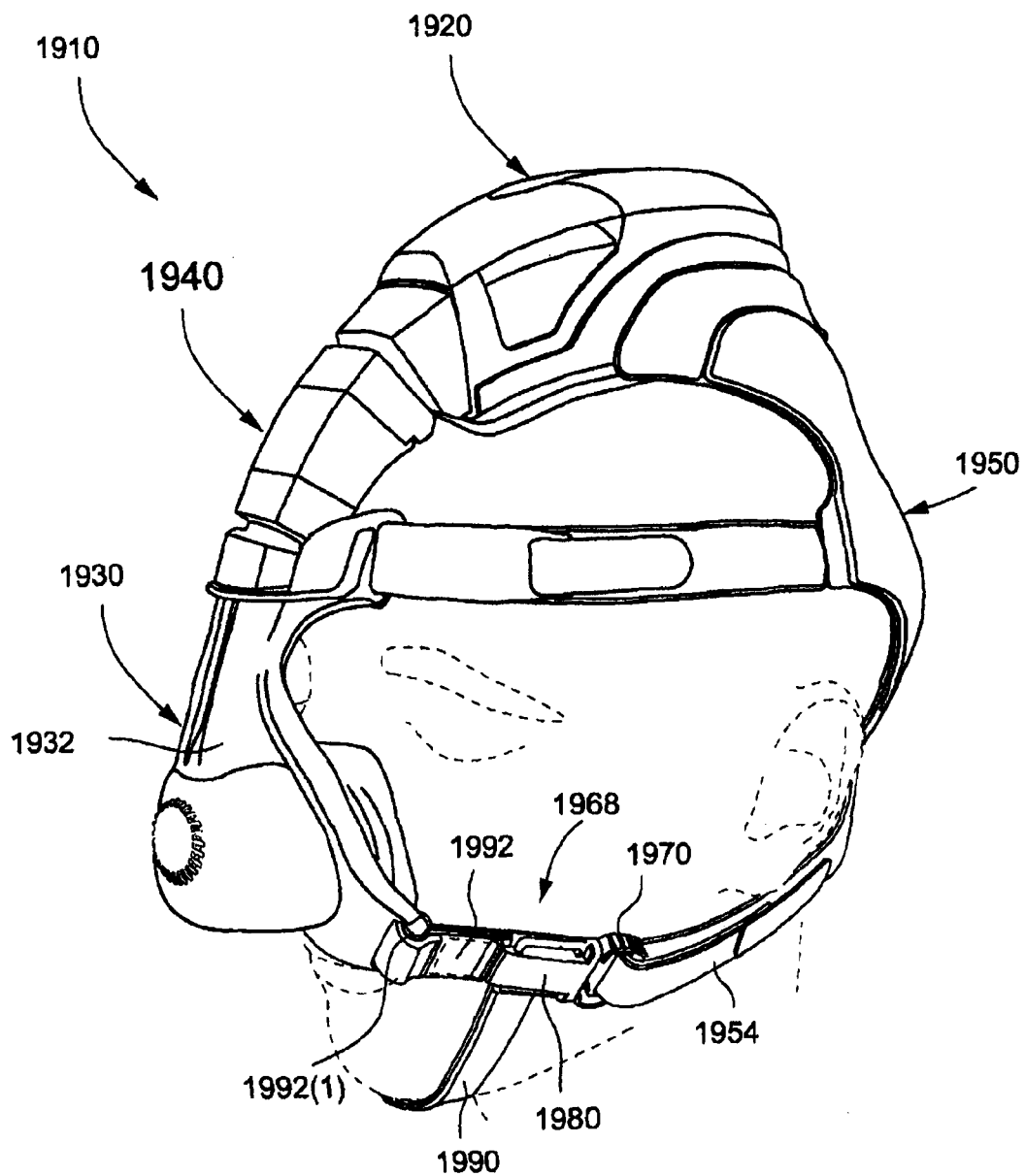
FIG. 118 is a perspective view of a headworn PAP system including a clip arrangement according to an example of the present technology.
Figure 119:
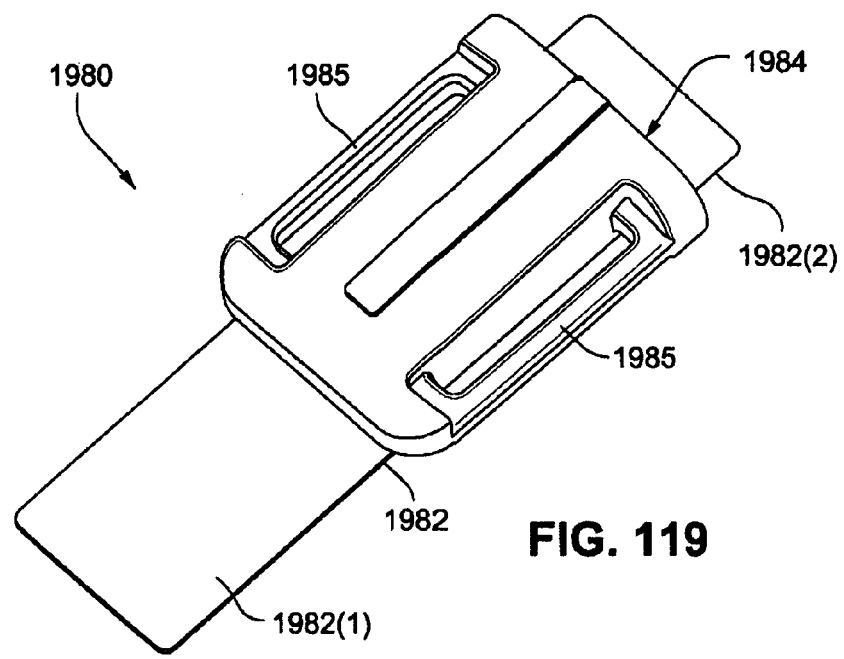
FIG. 119 is a perspective view of a clip receptacle of a clip arrangement according to an example of the present technology.
Figure 120:
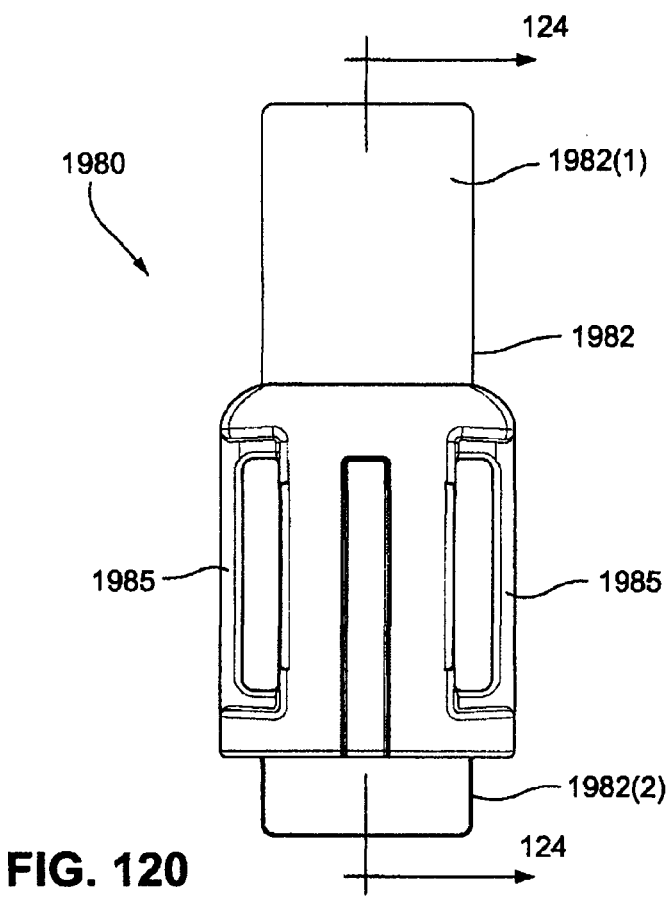
FIG. 120 is a top view of the clip receptacle of FIG. 119.
Figure 125:
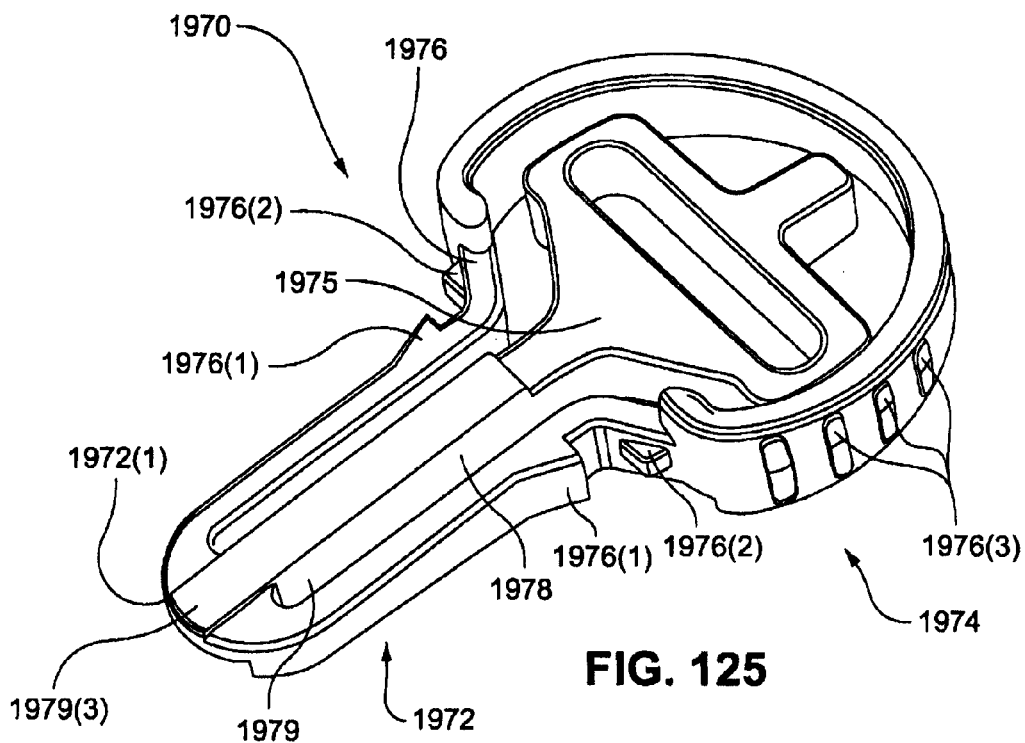
FIG. 125 is a perspective view of a headgear clip of a clip arrangement according to an example of the present technology.
Figure 126:
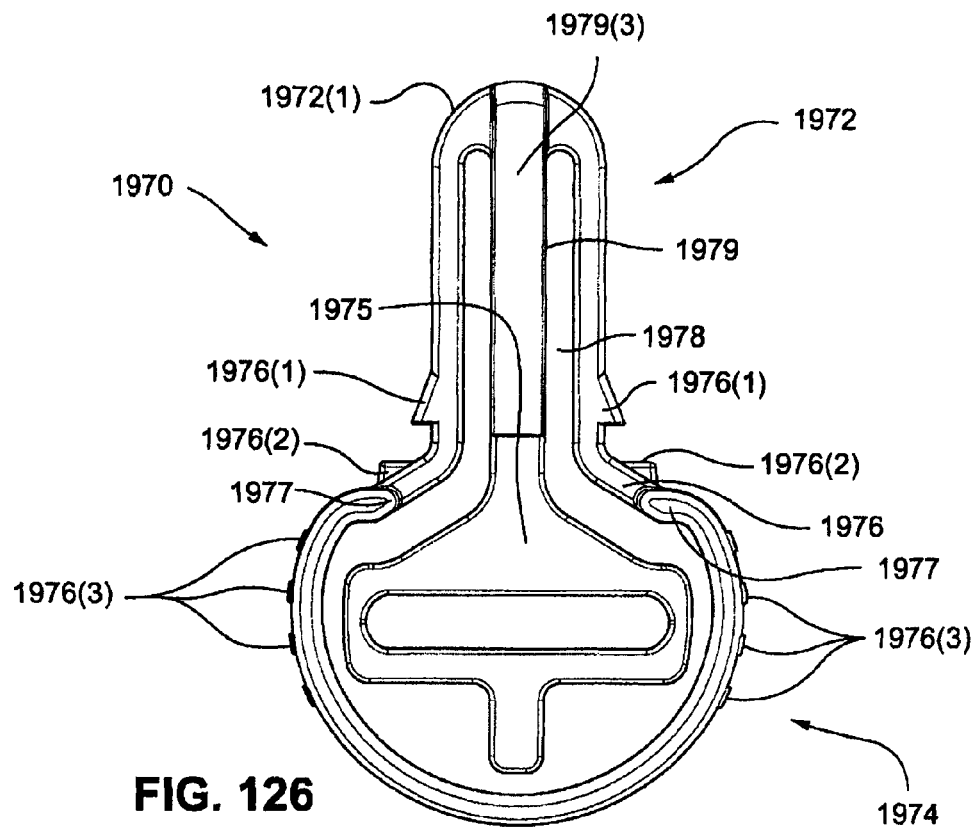
FIG. 126 is a top view of the headgear clip of FIG. 125.
Figure 130:
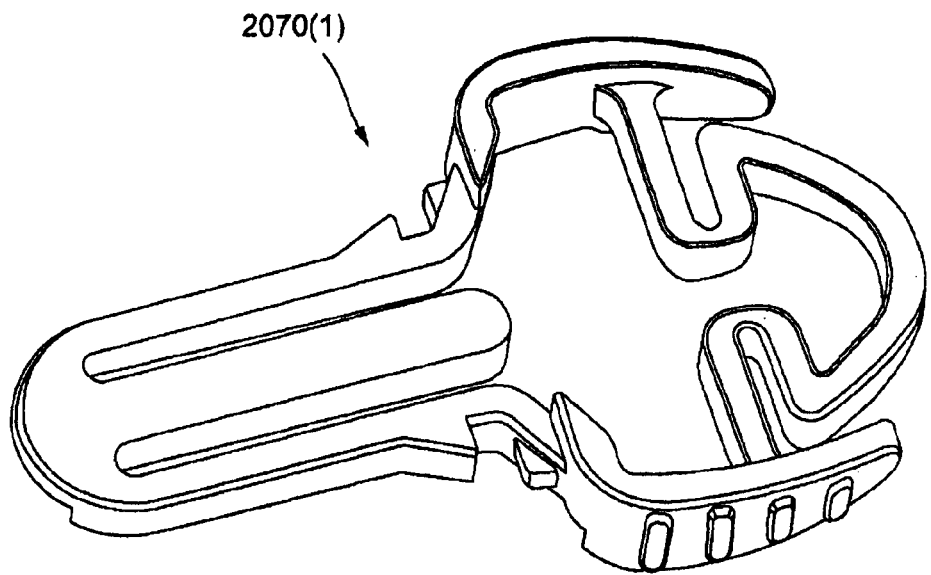
Figure 131:
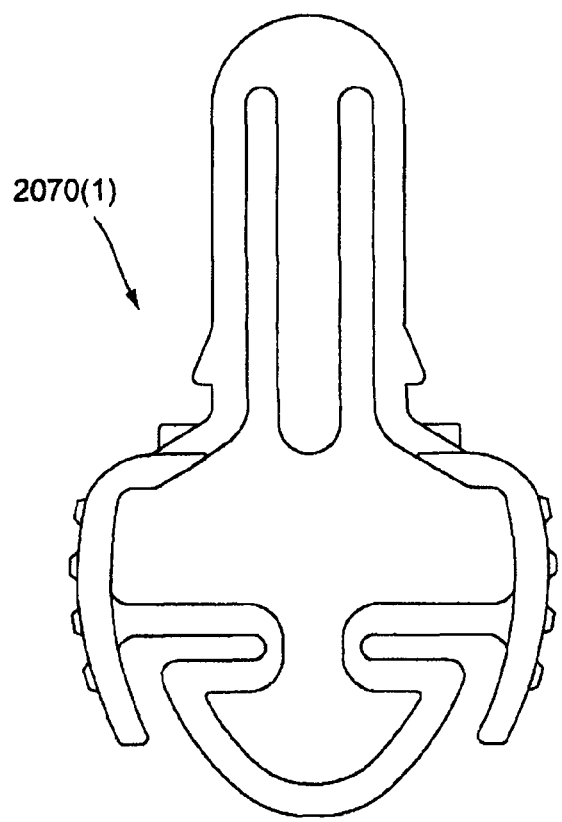
Figure 135:
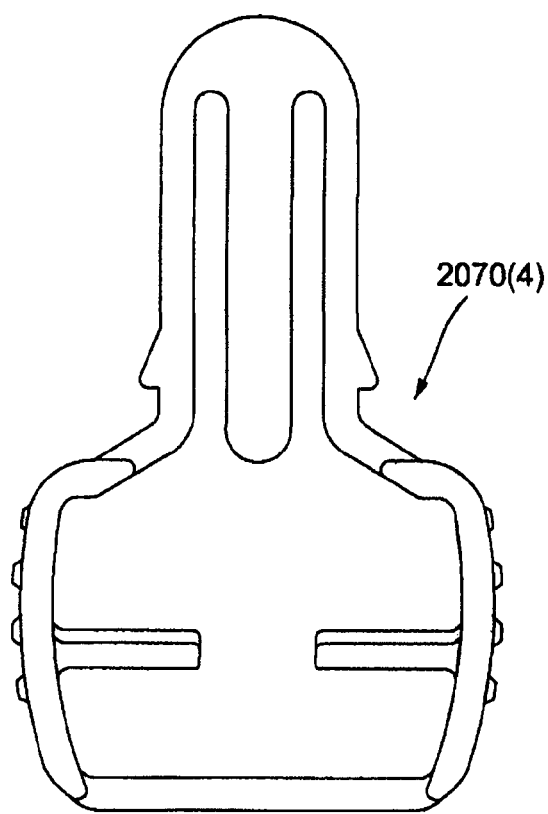
FIG. 135 shows a headgear clip according to another example of the present technology.
Figure 136:
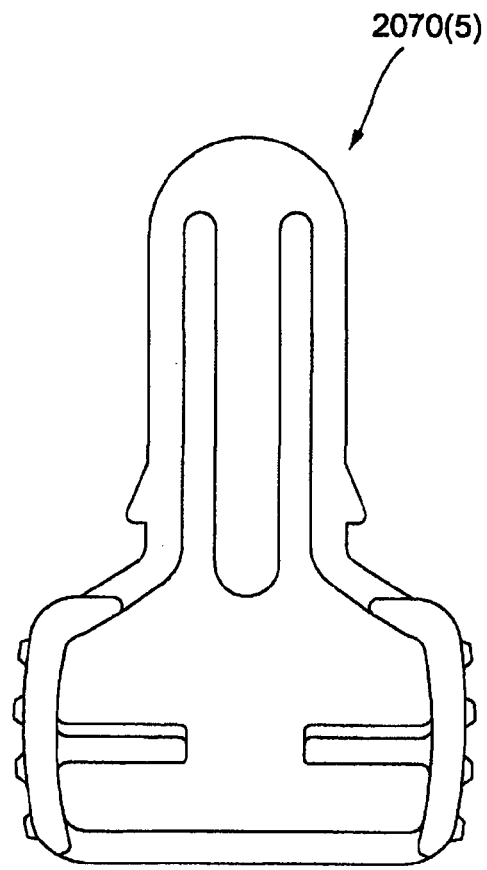
FIG. 136 shows a headgear clip according to another example of the present technology.
Figure 137:
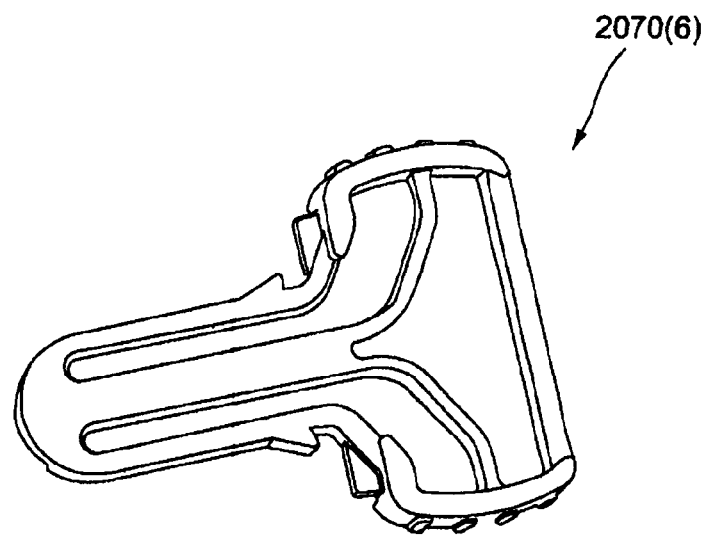
FIG. 137 shows a headgear clip according to another example of the present technology.
Figure 138:
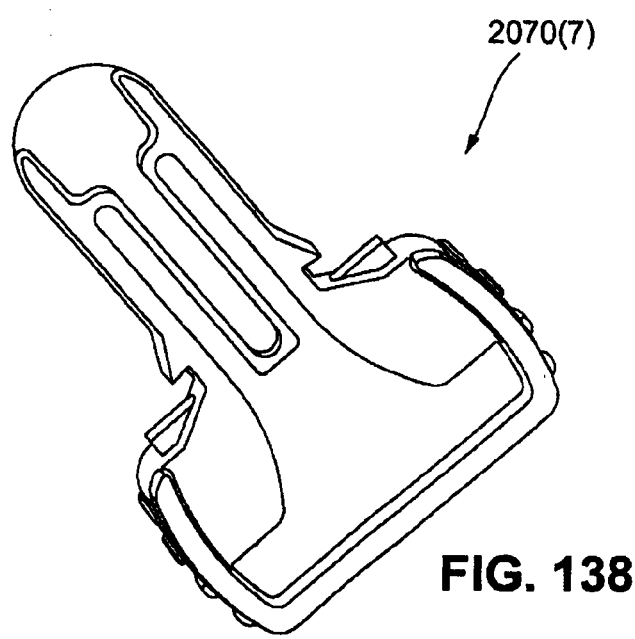
FIG. 138 shows a headgear clip according to another example of the present technology.

FIG. 118 shows a headworn PAP system 1910 including a clip arrangement 1968 according to another example of the present technology. The headworn PAP system 1910 includes a patient interface 1930 adapted to be secured to and sealed against a portion of the patient's face, in use, by headgear 1950, a flow generator 1920 adapted to be connected to the patient interface and secured by a portion of the headgear 1950 to the patient's head, and an outlet tube assembly 1940 that interconnects the patient interface and the flow generator.

The clip arrangement 1968 is provided on each side of the frame 1932 of the patient interface for engaging both lower side straps 1954 of the headgear and the chin strap 1990. The clip arrangement 1968 includes a clip receptacle 1980 (shown isolated in FIGS. 119-124) adapted to be secured or otherwise provided to the frame and a headgear clip 1970 (shown isolated in FIGS. 125-129) adapted to be releasably or removably connected to the clip receptacle.

As best shown in FIGS. 119-124, the clip receptacle 1980 includes a patient contacting side (or side closest to the patient's skin in use) having an elongated bottom wall 1982 adapted to attach to a strap 1992 (e.g., see FIG. 118) for securing or otherwise attaching the clip receptacle to the frame. The bottom wall 1982 provides a front portion or tongue 1982(1) structured to be inserted or otherwise attached to a first end of the strap (e.g., inserted and secured between layers of the strap), and a rear portion 1982(2) structured to attach to a second end of the strap. Such attachment arrangement shown in FIG. 118 creates a loop 1992(1) in the strap 1992 adapted to engage or otherwise attach to a slot provided on the frame 1932 in use.

The non-patient contacting side (or side that faces away from the patient's skin in use) includes a slot or aperture 1984 adapted to receive the front portion of the headgear clip in use. The interior of the slot 1984 provides shoulders or catch engaging portions 1984(1) (e.g., see FIG. 123) adapted to receive or interface with respective catches provided to the headgear clip in use.

Also, each side of the clip receptacle includes a cross-bar or chin strap loop 1985 that forms an opening through which a chin strap may pass and be removably attached.

As best shown in FIGS. 125-129, the headgear clip 1970 includes a front portion 1972 adapted to interface with the clip receptacle and a rear portion 1974 adapted to interface with the lower side strap of the headgear.

As illustrated, the clip 1970 includes a main body 1975 and an outer ring 1976 provided to the main body. The outer ring 1976 is spaced from the main body 1975 by a gap 1978 which provides a flexing space to allow the outer ring to resiliently deform inwardly towards the main body in use, e.g., within the plane of the main body.

The outer ring 1976 provides flexible spring arm portions 1977 on each side of clip. Each spring arm portion 1977 includes a catch or locking tab 1976(1) adapted to engage a respective catch engaging portion within the slot of the clip receptacle and a stop 1976(2) to prevent the clip from pushing into the slot of the clip receptacle too far. The outwardly facing surface of each spring arm portion includes finger grips 1976(3) (e.g., series of spaced apart protrusions) to facilitate gripping of the outer ring.

The rear portion of the main body includes a slot 1975(1) through which a lower headgear strap may pass and be removably attached, e.g., an end portion of the lower strap of the headgear may be wrapped around rear portions of the main body and outer ring, e.g., see FIG. 118. Also, the rear portion of the main body includes a tab 1975(2) to prevent inwards deformation of the outer ring in this region.

The front portion of the main body provides an elongated support tab 1979 including a groove 1979(1) adapted to receive a protrusion 1984(2) (e.g., see FIG. 123) provided in the slot of the clip receptacle when the locking clip is removably coupled to the clip receptacle. As illustrated, the open end of the groove 1979(1) includes a widened portion 1979(2) with tapered edges (e.g., see FIG. 128) to facilitate entry of the protrusion into the groove in use. Also, the support tab 1979 includes a protrusion 1979(3) adapted to engage within a groove 1984(3) (e.g., see FIG. 123) provided in the slot of the clip receptacle when the locking clip is removably coupled to the clip receptacle. Thus, upper and lower surfaces of the support tab 1979 provide different shapes, e.g., protrusion and groove, to prevent incorrect alignment and assembly of the clip to the clip receptacle. In addition, the outwardly facing surfaces 1972(1) at the front end of the clip are rounded or contoured to help guide the clip into the slot of the receptacle.

In use, the front portion 1972 of the headgear clip may be inserted into the slot 1984 of the clip receptacle 1980 to engage the catches 1976(1) with respective catch engaging portions 1984(1) and secure the headgear clip to the clip receptacle. The groove 1979(1)/protrusion 1979(3) provided to the support tab 1979 engages the protrusion 1984(2)/groove 1984(3) provided within the slot 1984 of the receptacle to facilitate entry and alignment of the headgear clip. The spring arms may be depressed to disengage the catches 1976(1) from the catch engaging portions 1984(1) and thereby allow the headgear clip to be released from the clip receptacle. In an example, each catch includes a height of about 0.5-2 mm, e.g., 1 mm, and displaces about 0.2-0.5 mm, e.g., 0.3 mm, to release from the respective catch engaging portion. In an example, the clip will retain in the receptacle for up to at least 30N of force applied in a release direction away from the receptacle.

FIGS. 130 to 138 illustrate headgear clips according to alternative examples of the present technology. In each example, sides of the clip may be pinched to disengage catches from the clip receptacle. The headgear clips illustrate different clip lengths and pinching forces for release, e.g., 10-20N. For example, the rear portion of the clips 2070(1), 2070(2), 2070(3), 2070(4), 2070(5), 2070(6), and 2070(7) include alternative arrangements with alternative stress relieving bends and headgear strap attachment points.

Vent

In an example, the vent 1566 provided to the frame 1532 may be a diffuse vent, e.g., vent cap including dome and multiple vent holes arranged on an annular side wall of the dome to provide diffuse airflow such as that described in PCT Application No. PCT/AU2009/001102, which is incorporated herein by reference in its entirety.

Cushion

As best shown in FIG. 94, the non-face contacting side of the cushion 1560 includes a tongue 1561 with a sealing lip or bead 1563 adapted to engage within a groove or channel 1565 provided to the frame 1532. The sealing lip 1563 may interface with one or more ribs provided within the channel 1565, e.g., to enhance retention.

The face-contacting side of the cushion includes a dual wall arrangement, e.g., membrane 1562 and underlying support cushion 1567. However, the cushion may include a one wall or more than two wall arrangement. Also, the wall arrangement may vary around the cushion perimeter, e.g., single wall arrangement (i.e., membrane only) in the nasal bridge region and dual wall arrangement (i.e., membrane and underlying support cushion) in the remaining regions as shown in FIG. 94.

In an example, the desired angle of the cushion on the patient's face may determine or set the angle of the inlet tube. This arrangement may be driven by the membrane depth at the top of the cushion (i.e., across the nasal bridge). At this point, provision may also be made for the cushion bead depth and then the diameter of the inlet tube. The sum of these distances creates a minimum horizontal distance from the face which is approximately the furthermost protrusion of the patient interface and may effectively determine the rest of the patient interface geometry.

Alternative Examples of Outlet Tube

FIGS. 47-55 illustrate alternative examples of the outlet tube and alternative examples for connecting the outlet tube to the flow generator and patient interface (e.g., flexible and inflexible couplings).

FIG. 47 shows a shortened and flexible outlet tube 540 provided between the flow generator 20 and the inlet tube 64 of the patient interface. FIG. 48 is an isolated view of the shortened and flexible outlet tube 540.

FIG. 49 shows a rigid outlet tube 640 with flexible couplings to the flow generator 20 and the inlet tube 64.

FIG. 50 shows a rigid outlet tube 740 with inflexible couplings to the flow generator 20 and the inlet tube 64.

Figure 51:
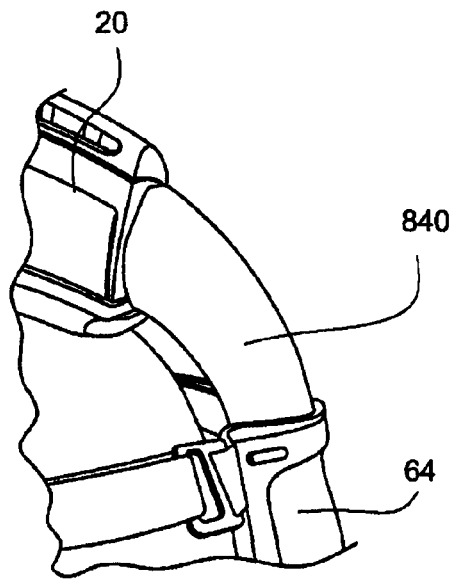

FIG. 51 shows a rigid outlet tube 840 with a flexible coupling to the flow generator 20 and an inflexible coupling to the inlet tube 64.

Figure 52:
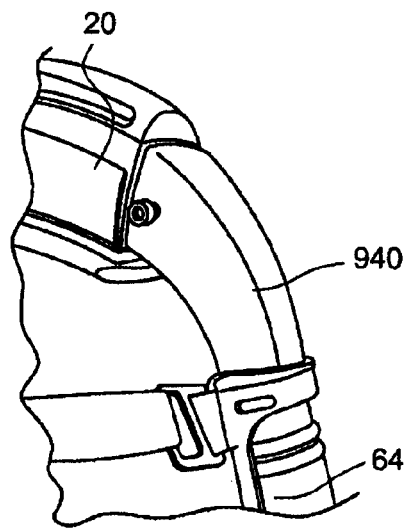

FIG. 52 shows a rigid outlet tube 940 with an inflexible coupling to the flow generator 20 and a flexible coupling to the inlet tube 64.

Figure 53:
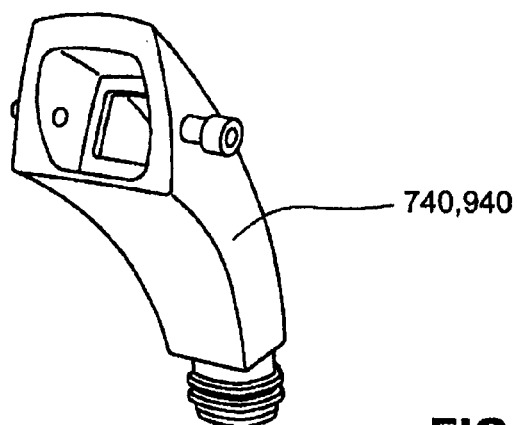

FIG. 53 shows an example of a rigid tube 740, 940 with an inflexible coupling to the flow generator.

Figure 54:
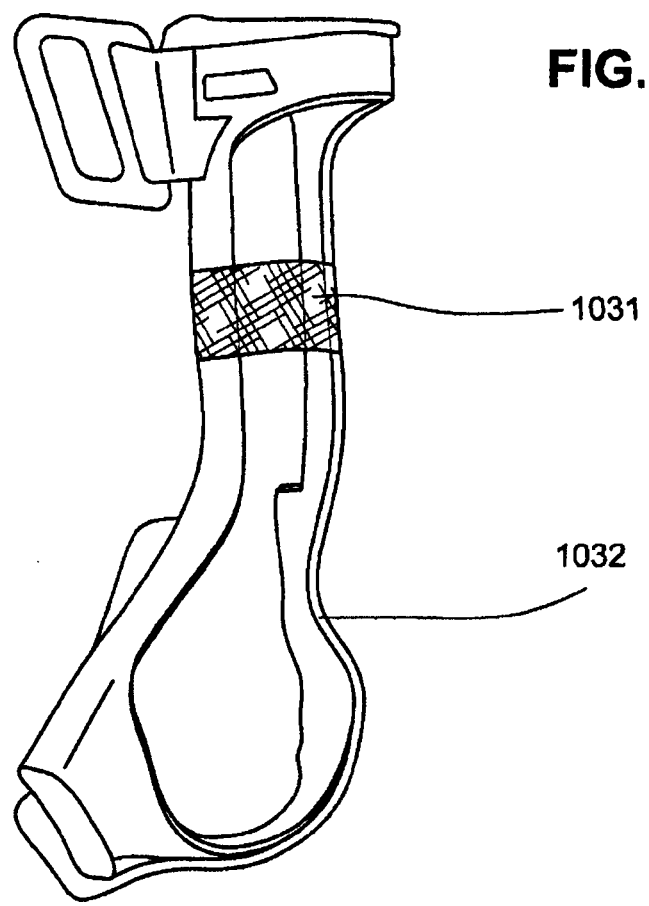

FIG. 54 shows an example of a frame 1032 with a flexible support 1031 to support and stabilize the inlet tube of the patient interface. The flexible support 1031 may be in the form of a flexible band or strip attached to the frame.

Figure 55:
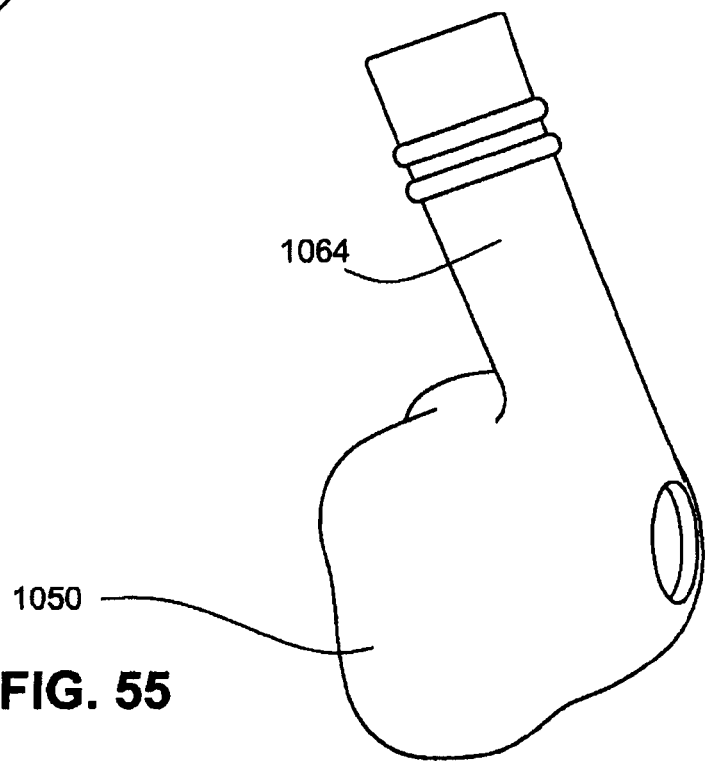

FIG. 55 shows an example of a cushion 1060 with flexible inlet tube 1064. The cushion 1060 and the flexible inlet tube 1064 may be formed as a single component from flexible material such as silicone.

Headgear

Headgear is provided to support the PAP system on the patient's head in use.

Figure 56:
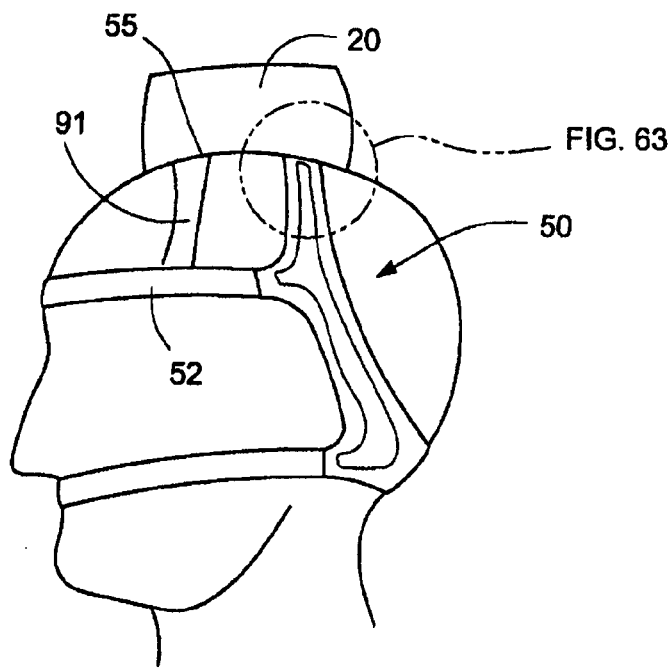
Figure 57:
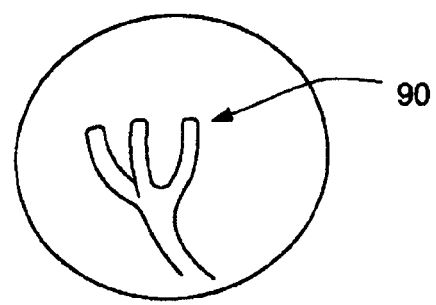
Figure 58:
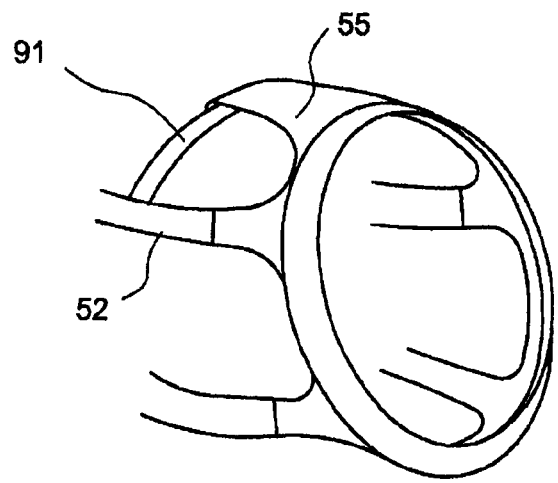

As shown in FIGS. 56 to 58, the headgear 50 may include vertical rigidizers or branches 90 along the cradle 55 to help prevent the flow generator 20 from sliding forwards and/or backwards. Also, the headgear may include additional webbing or additional strap portions (e.g., strap portion 91 between the upper side strap 52 and the cradle 55 supporting the flow generator) to prevent the flow generator from tilting. Also, the outlet tube from the flow generator may be structured to provide less give to prevent the flow generator from titling backwards. FIG. 58 is a back view of the headgear 50.

Figure 59:
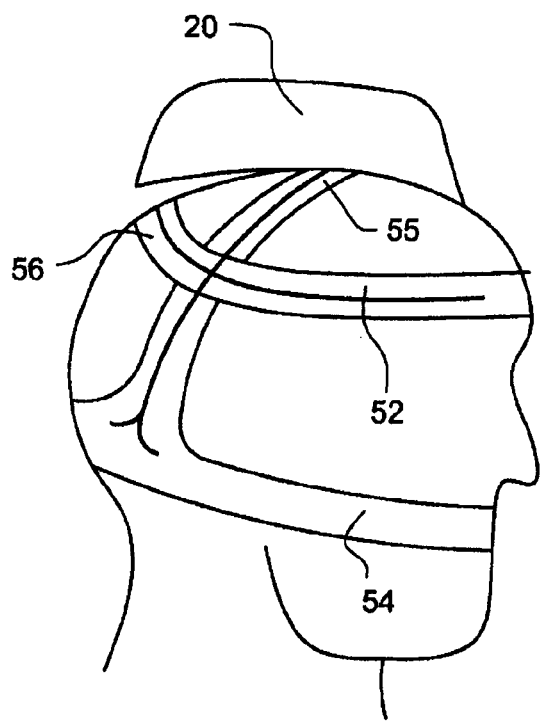
Figure 60:
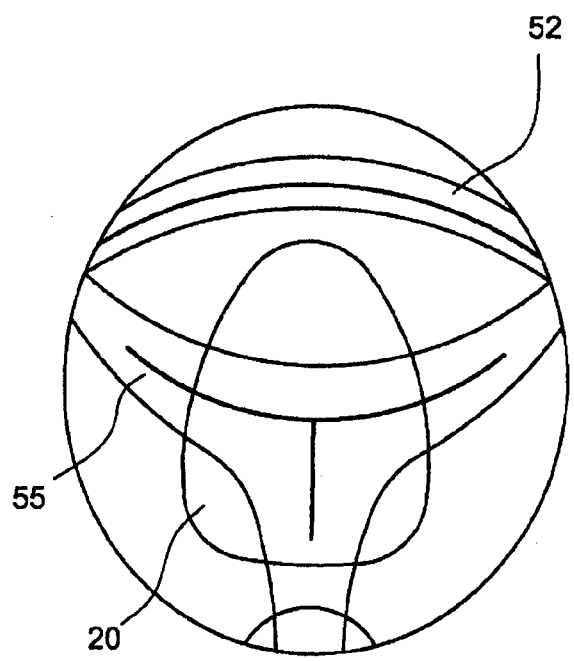

In FIGS. 59 and 60, the headgear includes upper forehead strap 52, lower straps 54, crown strap 56, and a Y-shaped cradle or mount 55 for the flow generator 20. A rigidizer may be provided to one or more of the straps, e.g., forehead strap, crown strap, and cradle. In an example, the headgear may be structured to maintain its shape.

Figure 61:
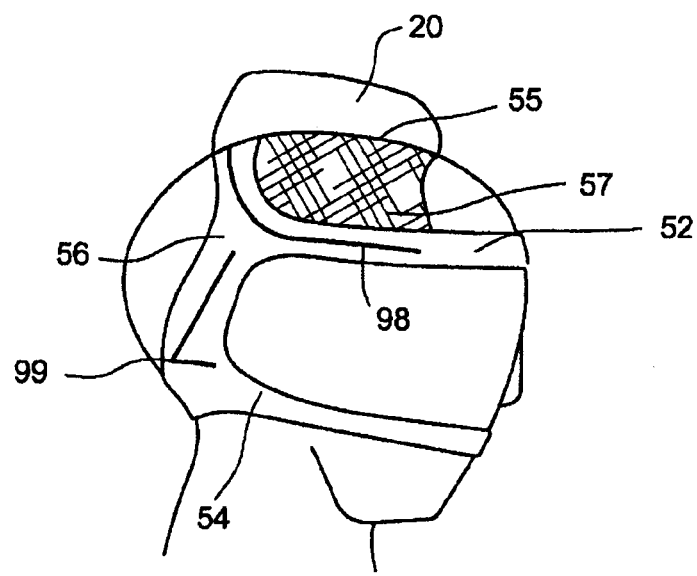
Figure 62:
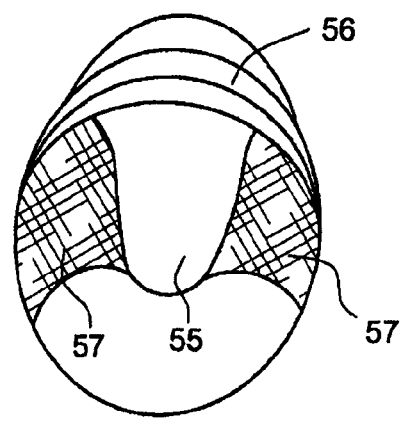
Figure 63:
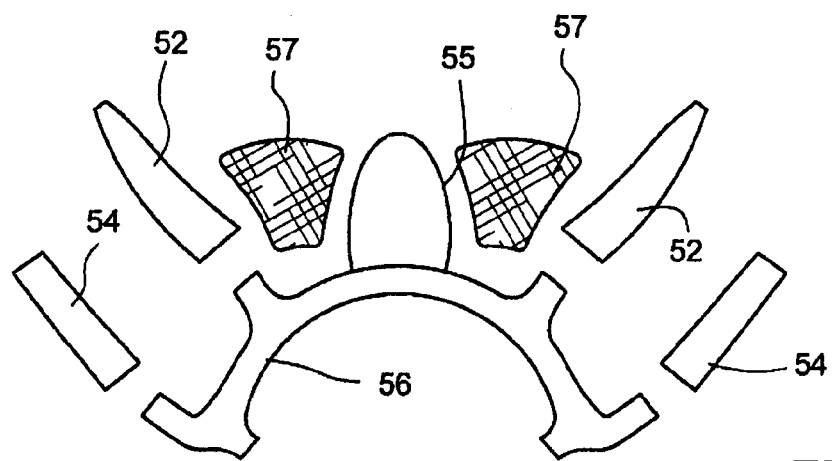

In FIGS. 61, 62, and 63, the headgear includes a seven piece construction with upper side straps 52, lower side straps 54, crown strap 56 with cradle 55, and mesh portions 57 between the cradle 55 and upper side straps 52 to hold the cradle 55 in place. The mesh portions 57 (e.g., stretch mesh) keep the flow generator steady in use. A rigidizer 98 may be provided along the upper side straps and extend into the crown strap. Also, a separate rigidizer 99 may be provided along a lower portion of the crown strap.

Figure 64:
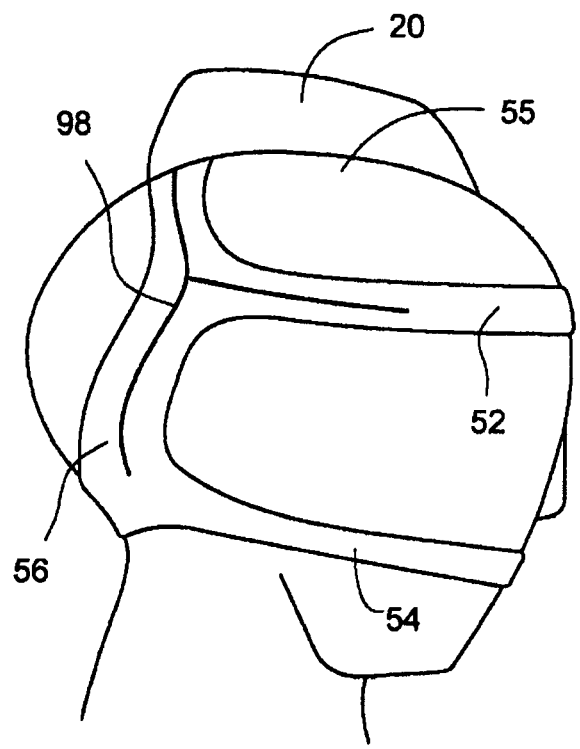
Figure 65:
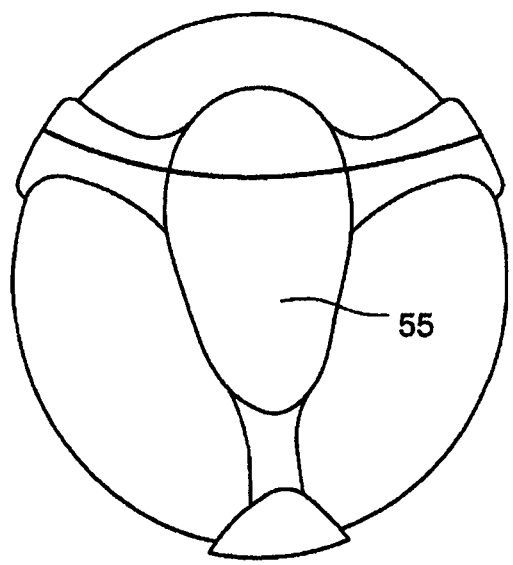
Figure 66:
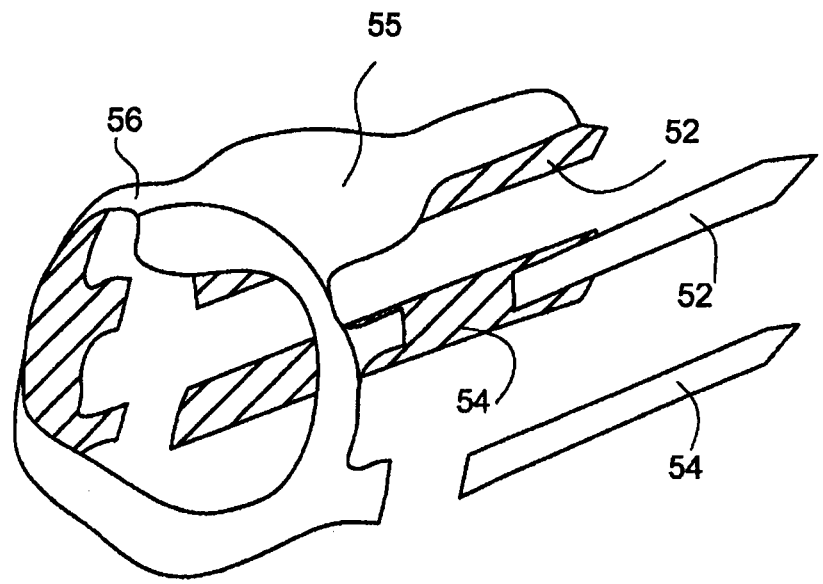

In FIGS. 64, 65, and 66, the headgear includes a five piece construction with upper side straps 52, lower side straps 54, and a crown strap 56 with integrated cradle 55. A rigidizer 98 may be provided along the upper side straps and extend along the crown strap. The upper side straps may be adjustable.

Figure 67:
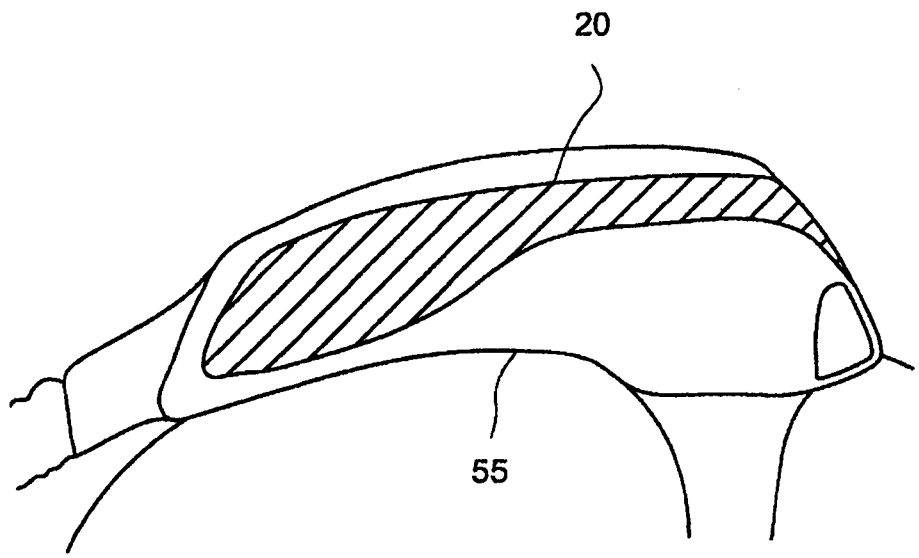
Figure 71:
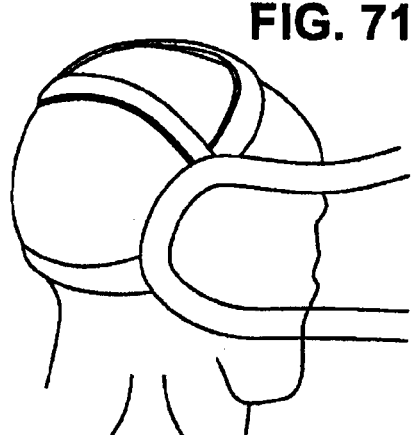
Figure 72:
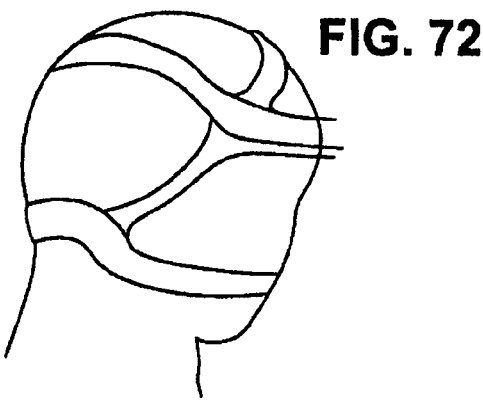
Figure 73:
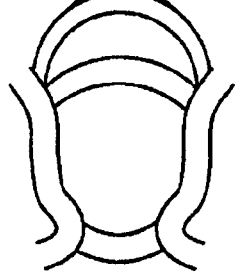
Figure 74:
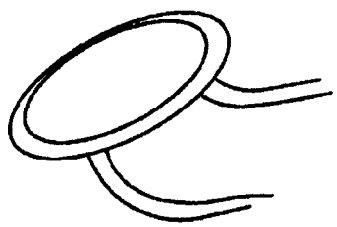
Figure 75:
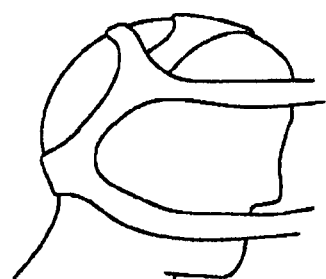
Figure 76:
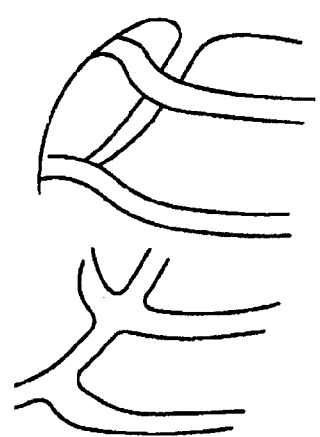

FIGS. 67 and 68 illustrate an example of a streamlined flow generator 20 and cradle 55 for supporting the flow generator.

FIGS. 69-76 illustrate alternative examples of headgear including alternative strap arrangements.

Figure 77:
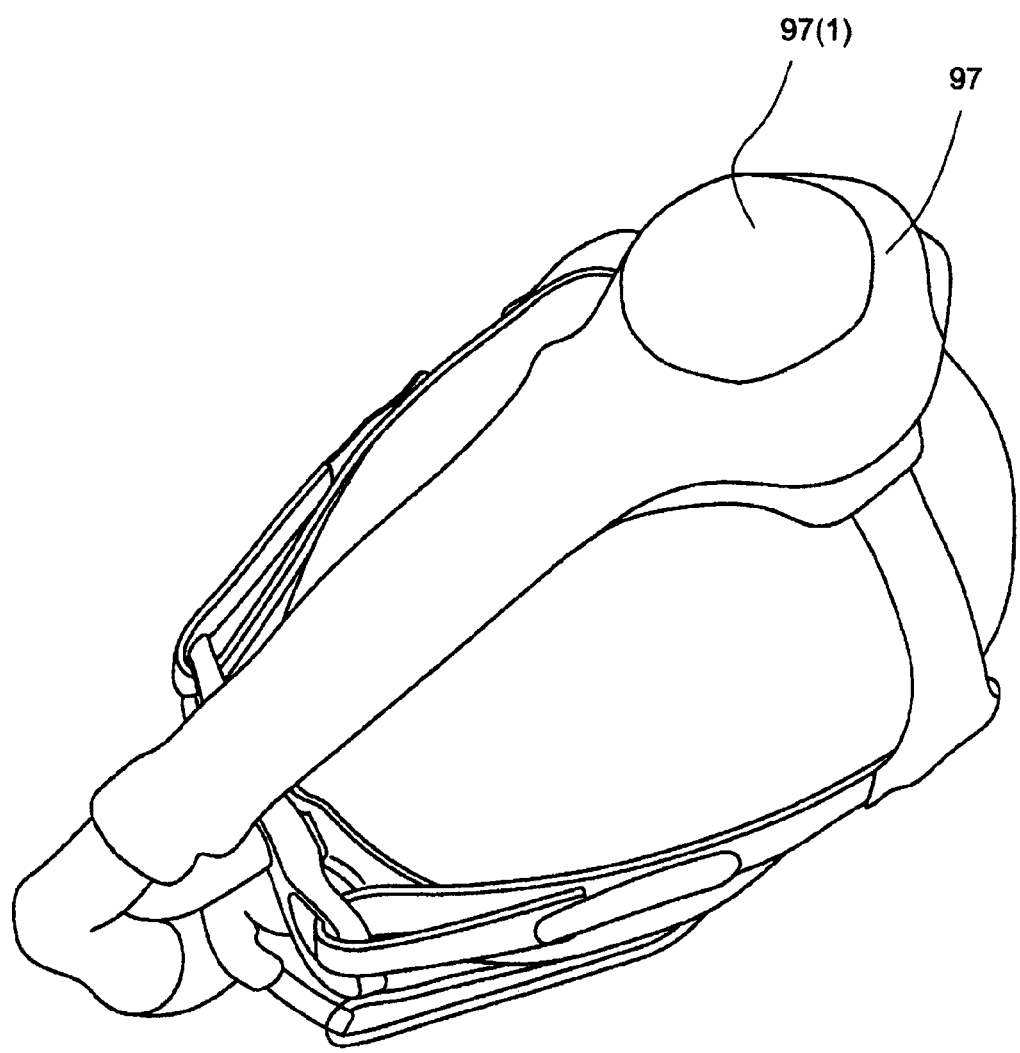

In FIG. 77, the headgear includes a sock 97 that extends over or covers the flow generator and outlet tubing. As illustrated, the sock includes foam padded outlets 97(1) for the flow generator.

Figure 78:
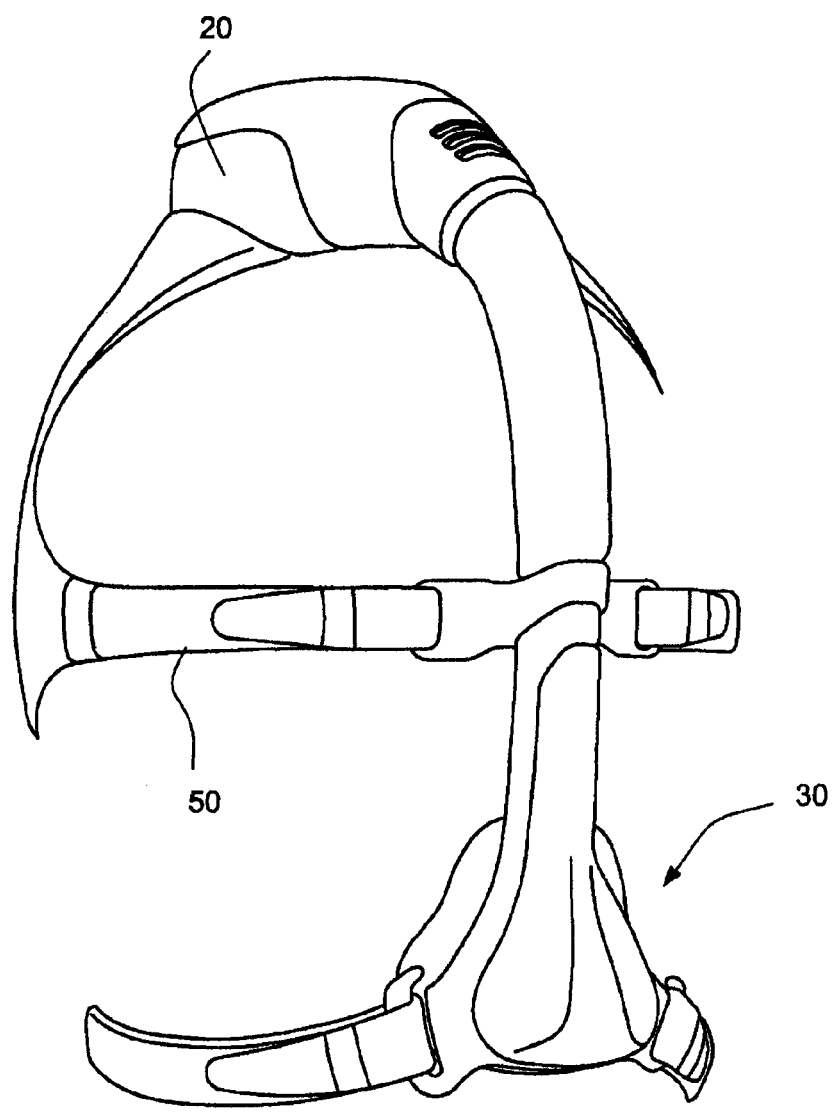
Figure 79:
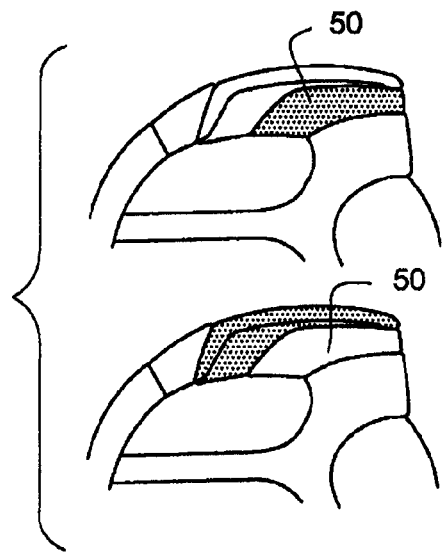
Figure 80:
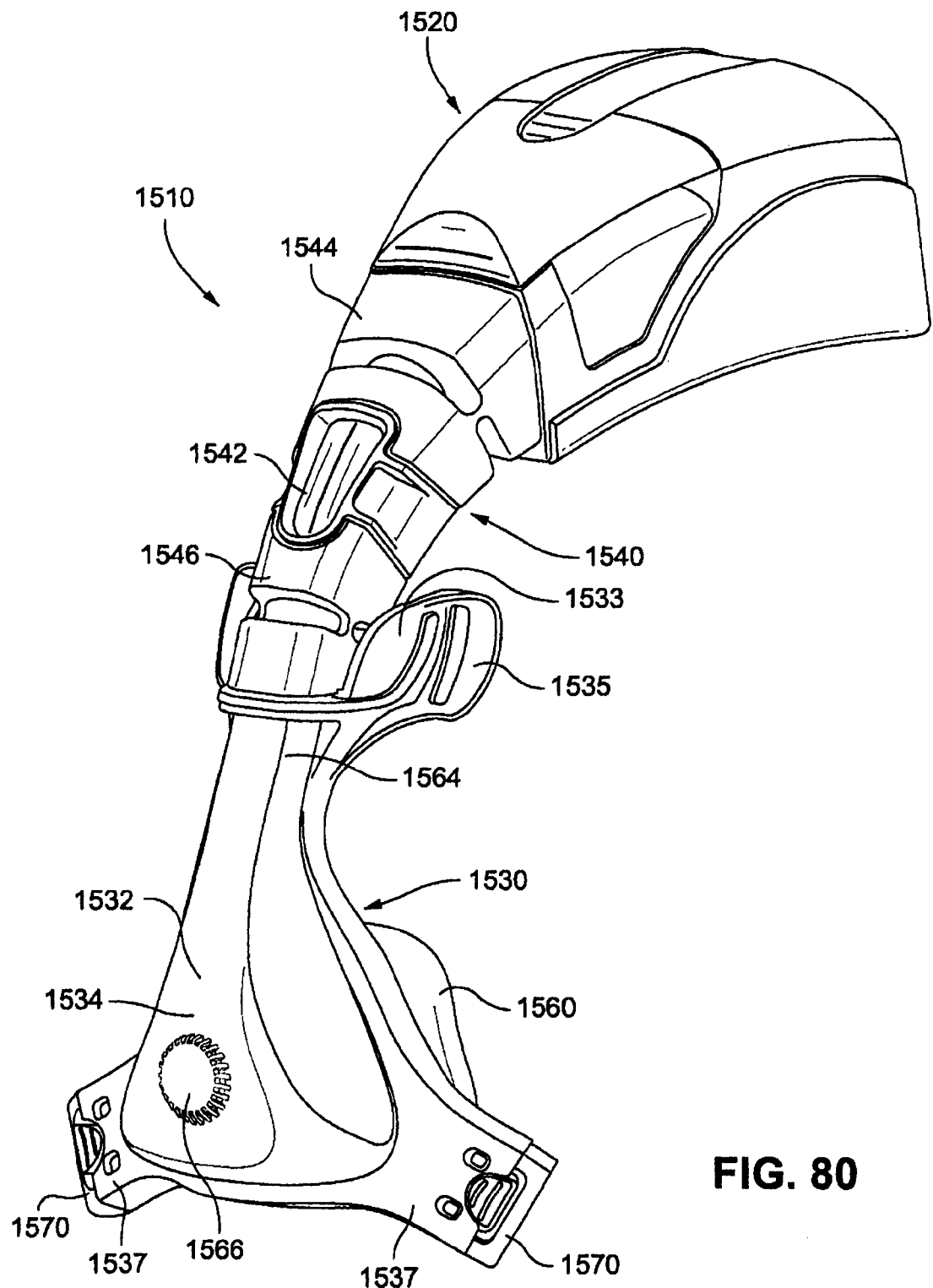
FIG. 80 is a perspective view of a headworn PAP system according to another example of the present technology.
Figure 81:
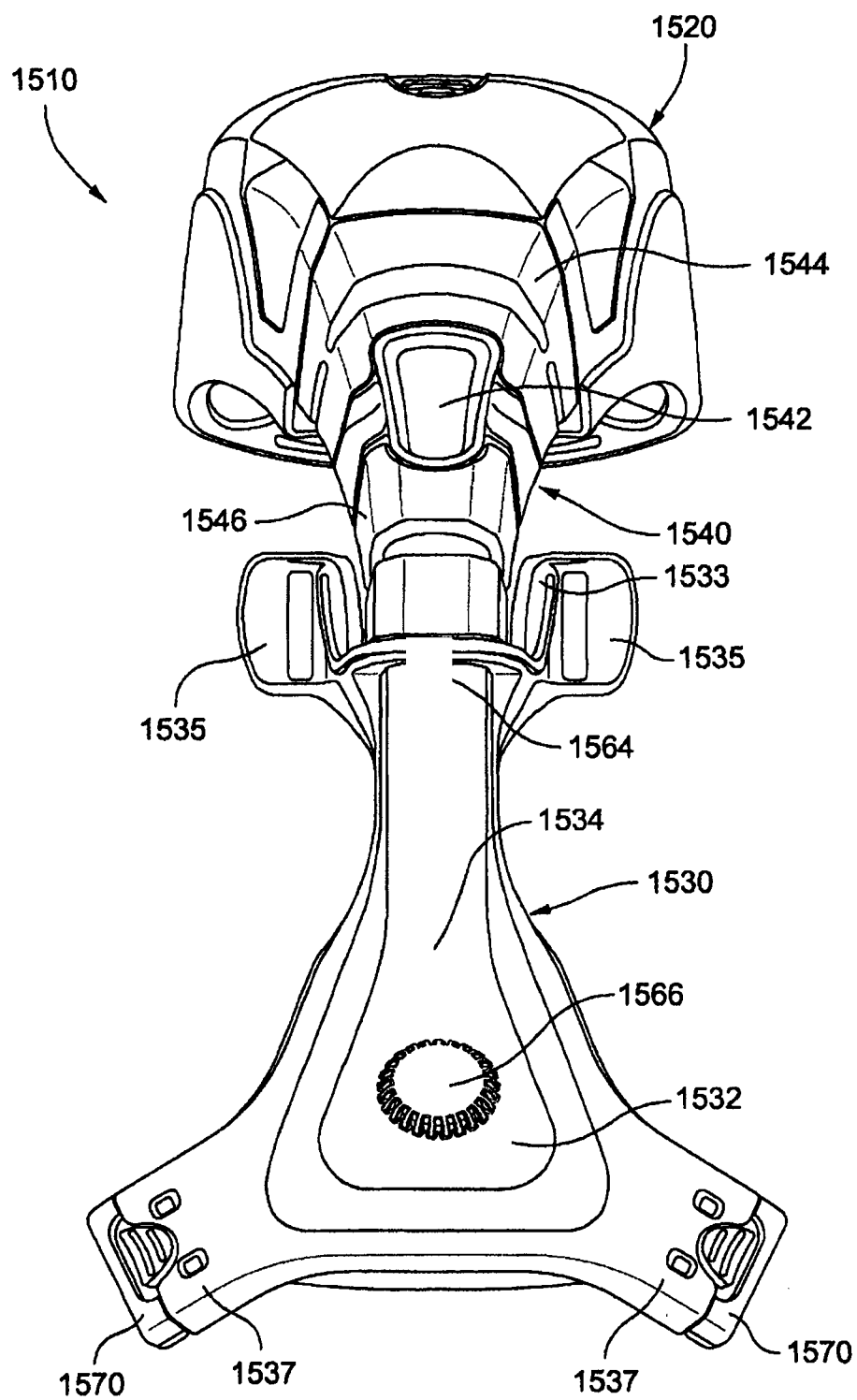
FIG. 81 is a front view of the headworn PAP system of FIG. 80.
Figure 82:
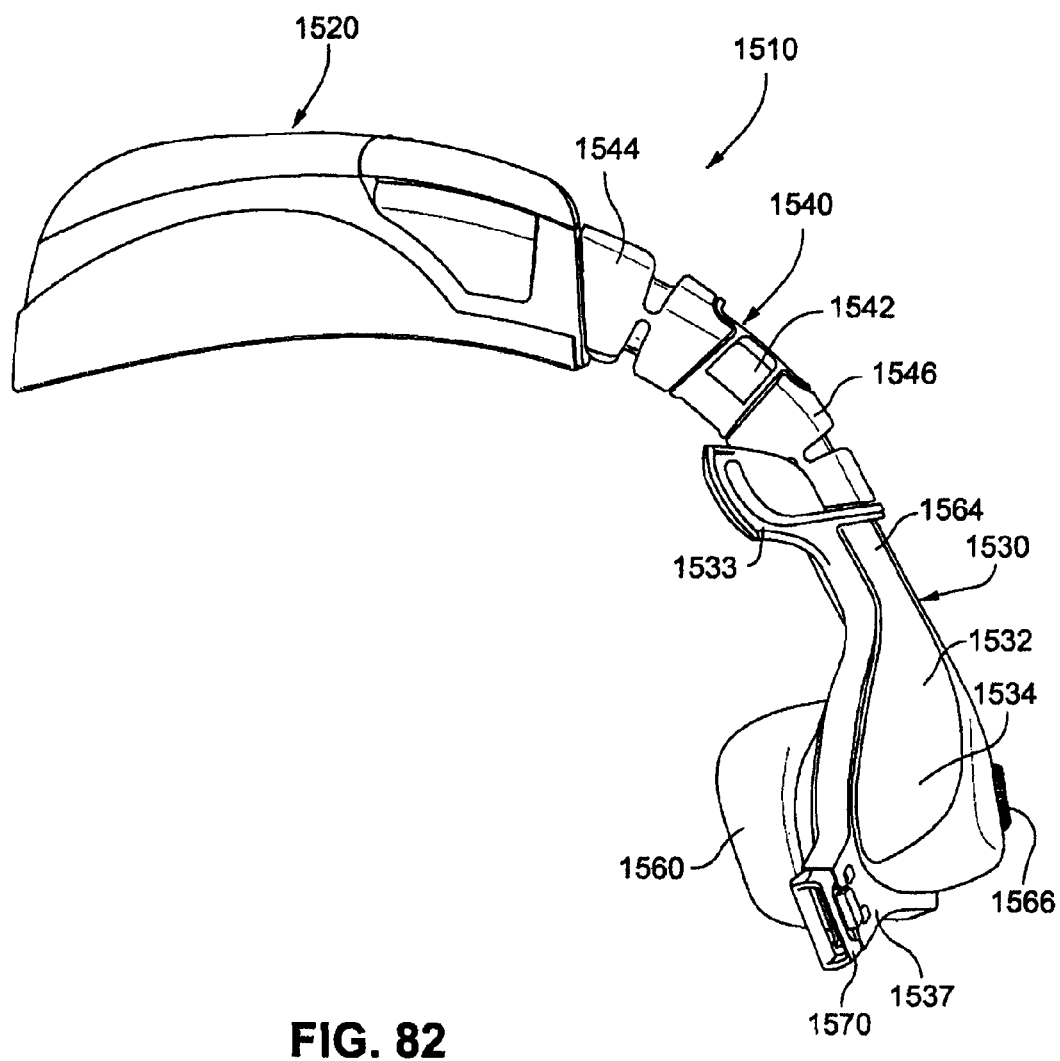
FIG. 82 is a side view of the headworn PAP system of FIG. 80.

FIGS. 78 and 79 show another example of a PAP system with headgear 50 structured to support the patient interface 30 and flow generator 20 in position on the patient's head in use. As illustrated, the headgear and cradle may be textured, colored, and/or streamlined to enhance aesthetics and comfort.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A PAP system adapted for providing a supply of pressurized respiratory gas to a patient for treatment of sleep disordered breathing, comprising:

headgear adapted to engage the patient's head;

a patient interface adapted to be secured to and sealed against a portion of the patient's face, in use, by the headgear;

a flow generator adapted to be connected to the patient interface and to generate the supply of pressurized gas, in use, wherein the flow generator is adapted to be secured by a portion of the headgear to the patient's head; and a tube assembly between the flow generator and the patient interface to deliver the pressurized gas generated by the flow generator to the patient interface;

wherein the tube assembly includes a relatively rigid outlet tube that provides a relatively smooth and fixed internal flow path to provide a relatively even and uninterrupted flow for the pressurized gas, wherein the tube assembly further includes a top articulated connector constructed of a relatively soft flexible material and configured to connect a top portion of the outlet tube with an outlet of the flow generator, and a bottom articulated connector constructed of a relatively soft flexible material and configured to connect a bottom portion of the outlet tube with an inlet tube of the patient interface, and wherein each of the top and bottom articulated connectors is structured to allow forward and backward movement with respect to the patient's face to accommodate a range of anthropometric variations between patients while substantially preventing lateral or side to side movement with respect to the patient's face for stability.

2. A PAP system according to claim 1, wherein the top and bottom articulated connectors provide first and second articulation points to provide flexibility to fit a range of patient head sizes and shapes.

3. A PAP system according to claim 1, wherein the top articulated connector includes an end inserted over an outer surface of the top portion of the outlet tube to provide a coupling between the outlet of the flow generator and the outlet tube that allows fore and aft flex and prevents contact between the outlet tube and the outlet of the flow generator.

4. A PAP system according to claim 1, wherein the bottom articulated connector includes an end inserted over an outer surface of the bottom portion of the outlet tube to provide a coupling between the outlet tube and the inlet tube of the patient interface that allows fore and aft flex and prevents contact between the outlet tube and the inlet tube of the patient interface.

5. A PAP system according to claim 1, wherein the patient interface includes a relatively rigid frame which supports a cushion.

6. A PAP system according to claim 5, wherein the frame includes a body portion defining a breathing chamber, the inlet tube, and a forehead support.

7. A PAP system according to claim 6, wherein the body portion includes a vent to allow the exhalation of gases.

8. A PAP system according to claim 7, wherein the vent is a relatively rigid vent.

9. A PAP system according to claim 1, wherein the headgear includes:
at least one headgear strap;
a chin strap; and
a clip arrangement structured to engage both the at least one headgear strap and the chin strap.

10. A PAP system according to claim 9, wherein the clip arrangement includes a clip receptacle and a headgear clip adapted to be releasably connected to the clip receptacle.

11. A PAP system according to claim 10, wherein the clip receptacle includes a chin strap loop adapted to attach the chin strap and the headgear clip includes a headgear strap loop adapted to attach the at least one headgear strap.

12. A PAP system according to claim 1, wherein the outlet of the flow generator includes structure to prevent connection of a standard air delivery tube.

13. A PAP system according to claim 1, wherein the outlet of the flow generator and the top articulated connector include a connection arrangement to provide mistake-free connection.

14. A PAP system according to claim 13, wherein one of the outlet of the flow generator and the top articulated connector includes one or more ribs and the other of the outlet of the flow generator and the top articulated connector includes corresponding recesses to provide the mistake-free connection.

15. A PAP system according to claim 1, wherein the outlet tube, the top articulated connector, and the bottom articulated connector include structure to ensure connection in a correct orientation and prevent the top and bottom articulated connectors from rotating relative to the outlet tube.

16. A PAP system according to claim 15, wherein the outlet tube includes protrusions or fingers adapted to be received in corresponding recesses provided to the top and bottom articulated connectors.

17. A PAP system according to claim 1, wherein the patient interface includes a forehead support adapted to engage a patient's forehead, the forehead support provided adjacent the inlet tube of the patient interface.

18. A PAP system according to claim 17, wherein the forehead support is structured to accommodate the bottom articulated connector and interface between the bottom articulated connector and the inlet tube of the patient interface.

19. A PAP system according to claim 17, wherein the inlet tube of the patient interface extends between arms of the forehead support.

20. A PAP system according to claim 1, wherein each of the top and bottom articulated connectors includes a set of side ribs to substantially prevent said lateral or side to side movement and allow said forward and backward movement.

21. A PAP system according to claim 1, wherein each of the top and bottom articulated connectors provides an articulation or flexing range of about 0-90° in each of forward and backward directions.

22. A PAP system according to claim 1, wherein each of the top and bottom articulated connectors provides a pivoted joint structured to only allow pivotal movement about a single axis in forward and backward directions with respect to the patient's face.

23. A PAP system according to claim 1, wherein each of the top and bottom articulated connectors includes a thinned wall section structured to allow said forward and backward movement.

24. A PAP system according to claim 1, wherein the patient interface includes a frame providing connectors for straps of the headgear.

25. A PAP system according to claim 1, wherein the top articulated connector includes a first annular recess along an interior surface thereof adapted to engage an annular barb or flange provided to the outlet of the flow generator.

26. A PAP system according to claim 1, wherein the top articulated connector includes a second annular recess along an interior surface thereof adapted to engage an annular barb or flange provided to the top portion of the outlet tube.

27. A PAP system according to claim 1, wherein the outlet of the flow generator includes one or more ribs adapted to engage corresponding recesses along an interior surface of the top articulated connector to provide mistake-free connection.

28. A PAP system according to claim 1, wherein the bottom articulated connector includes a first annular recess along an interior surface thereof adapted to engage an annular barb or flange provided to the bottom portion of the outlet tube.

29. A PAP system according to claim 1, wherein the bottom articulated connector includes one or more second recesses along an interior surface thereof adapted to engage respective barbs or flanges provided to the inlet tube of the patient interface.

30. A PAP system according to claim 1, wherein the outlet tube includes a fixed length.

31. A PAP system according to claim 1, wherein one or more of the top articulated connector and the bottom articulated connector includes a bellows section that provides an adjustable length.

32. A PAP system according to claim 1, wherein the outlet tube includes protrusions or fingers adapted to be received in corresponding recesses provided to the top and bottom articulated connectors.

33. A PAP system according to claim 32, wherein the protrusions or fingers are generally U-shaped.

34. A PAP system according to claim 1, further comprising a chin strap provided to the patient interface and adapted to extend under the patient's chin in use.

35. A PAP system according to claim 34, further comprising a clip arrangement provided to each side of the patient interface, the clip arrangement structured to engage both a lower side strap of the headgear and the chin strap.

36. A PAP system according to claim 35, wherein the clip arrangement includes a clip receptacle provided to the patient interface and a headgear clip adapted to be releasably connected to the clip receptacle.

37. A PAP system according to claim 36, wherein the clip receptacle is provided to a strap extending from a frame of the patient interface.

38. A PAP system according to claim 36, wherein the clip receptacle includes a chin strap loop adapted to attach the chin strap and the headgear clip includes a lower headgear strap loop adapted to attach the lower side strap of the headgear.

39. A PAP system adapted for providing a supply of pressurized respiratory gas to a patient for treatment of sleep disordered breathing, comprising:

headgear adapted to engage the patient's head;

a patient interface adapted to be secured to and sealed against a portion of the patient's face, in use, by the headgear;

a flow generator adapted to be connected to the patient interface and to generate the supply of pressurized gas, in use, wherein the flow generator is adapted to be secured by a portion of the headgear to the patient's head; and a tube assembly between the flow generator and the patient interface to deliver the pressurized gas generated by the flow generator to the patient interface;

wherein the tube assembly includes a relatively rigid outlet tube that provides a relatively smooth and fixed internal flow path to provide a relatively even and uninterrupted flow for the pressurized gas to assist in reducing noise during treatment, wherein the tube assembly further includes a top articulated connector constructed of a relatively soft flexible material and configured to connect a top portion of the outlet tube with an outlet of the flow generator, and a bottom articulated connector constructed of a relatively soft flexible material and configured to connect a bottom portion of the outlet tube with an inlet tube of the patient interface, and wherein the outlet tube tapers along its length from the top portion to the bottom portion such that a diameter of the outlet tube continuously decreases from the top portion to the bottom portion to assist in reducing noise during treatment.

* * * * *